(12) United States Patent
Kass et al.

(10) Patent No.: US 10,653,405 B2
(45) Date of Patent: May 19, 2020

(54) SKIN RETRACTOR AND PROP DEVICE AND METHODS OF USE

(71) Applicant: The Penn State Research Foundation, University Park, PA (US)

(72) Inventors: Rena Kass, Harrisburg, PA (US); Kristine Widders, Lancaster, PA (US); Barry M. Fell, Hummelstown, PA (US); Randy Haluck, Lititz, PA (US); Peter Dillon, Harrisburg, PA (US)

(73) Assignee: The Penn State Research Foundation, University Park, PA (US)

( * ) Notice: Subject to any disclaimer, the term of this patent is extended or adjusted under 35 U.S.C. 154(b) by 125 days.

(21) Appl. No.: 15/749,981

(22) PCT Filed: Aug. 3, 2016

(86) PCT No.: PCT/US2016/045240
§ 371 (c)(1),
(2) Date: Feb. 2, 2018

(87) PCT Pub. No.: WO2017/023967
PCT Pub. Date: Feb. 9, 2017

(65) Prior Publication Data
US 2018/0235592 A1 Aug. 23, 2018

Related U.S. Application Data

(60) Provisional application No. 62/200,851, filed on Aug. 4, 2015.

(51) Int. Cl.
*A61B 17/02* (2006.01)
*A61B 17/00* (2006.01)
(Continued)

(52) U.S. Cl.
CPC ...... *A61B 17/0206* (2013.01); *A61B 17/0218* (2013.01); *A61B 17/0293* (2013.01);
(Continued)

(58) Field of Classification Search
CPC . A61B 17/02; A61B 17/0206; A61B 17/0218; A61B 2017/00796; A61B 2017/0287
See application file for complete search history.

(56) References Cited

U.S. PATENT DOCUMENTS

| | | | | |
|---|---|---|---|---|
| 4,274,398 A | * | 6/1981 | Scott, Jr. ............ | A61B 17/0293 600/233 |
| 4,434,791 A | * | 3/1984 | Darnell .............. | A61B 17/0293 600/233 |

(Continued)

*Primary Examiner* — Ellen C Hammond
(74) *Attorney, Agent, or Firm* — Buchanan Ingersoll & Rooney PC

(57) ABSTRACT

The device can include a first member connected to a second member via junctions. The members can be statically or pivotally connected at the junctions via arms extending from cross-beams of the members. The junctions can be configured to provide a biasing force. Methods of using the device may include collapsing the device and inserting it through an incision, allowing the biasing force to cause continuous traction and counter-traction adjacent to a leading dissection edge so that retraction of the skin from the tissue can be facilitated during a surgical procedure.

6 Claims, 42 Drawing Sheets

(51) Int. Cl.
  *A61B 90/92* (2016.01)
  *A61B 90/94* (2016.01)
  *A61B 90/00* (2016.01)
  *A61B 17/34* (2006.01)
  *A61B 90/30* (2016.01)

(52) U.S. Cl.
  CPC .......... *A61B 17/3423* (2013.01); *A61B 90/30* (2016.02); *A61B 90/92* (2016.02); *A61B 90/94* (2016.02); *A61B 2017/00438* (2013.01); *A61B 2017/00477* (2013.01); *A61B 2017/00526* (2013.01); *A61B 2017/00561* (2013.01); *A61B 2017/00796* (2013.01); *A61B 2017/00951* (2013.01); *A61B 2090/0807* (2016.02)

(56) References Cited

U.S. PATENT DOCUMENTS

| | | | |
|---|---|---|---|
| 4,562,832 A * | 1/1986 | Wilder | A61B 1/32 138/DIG. 8 |
| 5,199,872 A * | 4/1993 | Leal | A61B 1/24 433/136 |
| 5,664,946 A | 9/1997 | Bedi | |
| 6,267,591 B1 | 7/2001 | Barstow | |
| 7,077,652 B2 * | 7/2006 | Kilcher | A61C 5/90 433/136 |
| 7,607,917 B2 | 10/2009 | Virnicchi et al. | |
| 8,083,746 B2 | 12/2011 | Novak | |
| 8,282,548 B2 | 10/2012 | Kelner | |
| 8,376,743 B1 * | 2/2013 | Bukhary | A61C 5/90 128/859 |
| 8,608,650 B2 | 12/2013 | Mangiardi | |
| D737,964 S * | 9/2015 | Jessop | D24/135 |
| D761,958 S * | 7/2016 | Jessop | D24/135 |
| D763,444 S * | 8/2016 | Jessop | D24/135 |
| D792,590 S * | 7/2017 | Jessop | D24/135 |
| 9,901,332 B2 * | 2/2018 | Jessop | A61B 1/32 |
| D820,445 S * | 6/2018 | Jessop | D24/135 |
| 10,016,258 B2 * | 7/2018 | Jessop | A61C 5/90 |
| 2013/0006240 A1 | 1/2013 | McNally et al. | |
| 2013/0230822 A1 * | 9/2013 | Hines | A61B 1/32 433/29 |

* cited by examiner

An incision can be made for the mastectomy using a scalpel. A skin retractor, such as a face lift retractor, can be used to start the dissection plane on the tissue plane directly posterior to the subcutaneous tissue of the mastectomy skin flap.

Once the dissection plane of the incision is started and carried out to a pre-selected length (e.g. 7 cm, 5 cm, 9 cm, etc.) and a pre-selected depth (e.g. 4-5 cm, 4-7 cm, 3-10 cm), the device may be inserted into the incision. The device can be inserted by moving the device to its closed position and subsequently placing the device in its closed position into the incision at a tissue pocket or other location of the incision. After the device is inserted, it can be allowed to move toward its open state. The device can be positioned adjacent the leading dissection edge in the incision. The device can be positioned so that the cross-beams or plates of the first and second members retract the mastectomy skin flap anteriorly while simultaneously retracting the breast posteriorly, which may allow for improved visualization of the dissection plane. Further dissection can subsequently be performed through the opening of the device and/or adjacent the device.

The device may continue to open as the further dissection is carried out until it reaches a point of maximal opening. The device can be reposition either to the more distal point of dissection or to a new location depending on area of tension.

After dissection is performed to the chest wall, the device can be removed. The breast may then be dissected from the pectoralis muscle.

The device can then be used the second breast if a bilateral mastectomy is performed by repeating the steps above.

FIG. 52

An incision can be made for the surgical procedure using a scalpel. A skin retractor, such as a face lift retractor, can be used to start the dissection plane on the first tissue plane directly posterior to the first tissue.

Once the dissection plane is started to form an initial incision of a pre-selected size, one or more of the devices may be inserted into the incision. If multiple devices are used, they can be spaced apart from each other within the incision. Each device can be inserted by manipulating the device to cause the device to move to its closed state. The device, in its closed state, can then be positioned into the incision (e.g. in a tissue pocket of the incision, etc.). The device can be positioned so that plates and/or or cross-beams of first and second members of the device retract the first tissue anteriorly while simultaneously retracting the second tissue posteriorly, which may allow for improved visualization of the dissection plane. Thereafter, application of light, suction, or other process may be performed via the opening of the device. For instance, a light can be held by a first or second member of the device for applying light to a portion of the incision or suction may be facilitated by a component of the device. Further dissection can be performed through the opening of the device.

The device may continue to open towards its open position as further dissection is carried out until it reaches a point of maximal opening. This further opening can occur automatically via the biasing force of the device that biases the device to the open position. During the further dissection, the device can be repositioned either to a more distal point of dissection or to a new location depending on area of tension. Alternatively, other devices may be positioned in the incision at these locations. The opening of the device can occur automatically without user actuation to permit continuous traction and counter-traction to be applied during the further dissection so that a surgeon or other support staff is free to use their hands to support other aspects of a procedure after the insertion of the device into the incision.

After the further dissection is performed to the body part, the device can be removed.

FIG. 53

SKIN RETRACTOR AND PROP DEVICE AND METHODS OF USE

CROSS-REFERENCE TO RELATED APPLICATIONS

The present application is the U.S. national stage application under 35 U.S.C. § 371 for International Patent Application No. PCT/US2016/045240, filed on Aug. 3, 2016, which claims priority to U.S. Provisional Patent Application No. 62/200,851, which was filed on Aug. 4, 2015.

BACKGROUND OF THE INVENTION

Field of the Invention

Embodiments disclosed herein generally relate to methods of using a skin retractor and prop device, and in particular methods using the device to provide hands-free traction and counter-traction at the leading edge of dissection.

Background of the Related Art

Due to advances in cosmesis, such as autologous reconstruction and implant-based reconstruction, surgeries are being performed with increasingly more complex and intricate procedures. For instance, mastectomies and similar surgeries may be conducted through incisions that are sized and positioned for optimizing cosmesis, which typically includes performing surgeries through small incisions. While performing mastectomies, the plane between the subcutaneous tissue and the glandular tissue of the breast is dissected by traction and counter-traction applied to the skin and breast tissue. Yet, the nature of mastectomy surgery generally results in a large skin flap under which the surgeon must operate if such surgery is to be performed through a small incision. This can significantly reduce the surgeon's visualization, thereby increasing risks associated with incomplete removal of breast tissue, bleeding, and/or injury to the skin flap.

Other surgeries may also include splaying and/or retracting skin and tissue away from an area of operation. These can include eye surgery, neck surgery, abdominal surgery, etc. Some of these do not result in a skin flap, but nonetheless involve manipulation of skin and other tissue so as to prevent it from interfering with the surgical procedure. The tendency of this skin and tissue to reform or rebound back to its natural position can also reduce the surgeon's visualization and increase risks associated such surgeries.

BRIEF SUMMARY OF THE INVENTION

The device can include a wedging unit that has a first member connected to a second member via a hinging unit. The hinging unit can be arms extending from the first and second members, where the arms may be connected to each other at a junction. The junction can be a pivot mechanism, a living hinge, and/or a resilient section of the arms at an interface between each first arm and second arm. For example, the hinging unit can be at least one first arm extending from the first member and at least one second arm extending from the second member, where each first arm meets with each second arm at a junction. The junction can be configured to provide a biasing force to generate a tendency of the wedging unit to maintain an open state or a propped state, but allows for displacement and/or deflection of the members and/or arms. At least one of the first member and the second member can include specific configurations and shapes that may facilitate splaying apart and/or propping skin and/or tissue. The device can have a natural tendency to be in an open state, in which the first member and the second member are separated and not in contact with each other. Displacement and/or deflection of the members and/or arms such as to cause the first and second members to move toward each other can form a closed state. Placement of the device against skin and/or tissue while in a closed state, and allowing the device to move toward the open state can assist in splaying the tissue open or apart. Further allowing the members and/or arms to maintain their position after advancing towards the open state can form a propped state, which can assist in propping the skin and/or tissue in a salutary position conducive for conducting surgical procedures within the area of operation.

As will be explained in detail, the wedging unit can exhibit various shapes and configurations, such as being U-shaped, V-shaped, having more or less arms, having various hinging units, etc. This may be done to facilitate performing various functions and to accommodate different types of surgeries and/or surgical procedures. The device can further be equipped with additional features, such as finger retainers, textured surfaces, non-slip surfaces, teeth, locking mechanisms, a tenting feature, tension adjustment mechanism for adjusting a biasing force applied by the arms, members, and/or hinging units to bias the device to its open state, etc. This can be done to further assist with performing desired functions. Some embodiments may include a kit with a plurality of wedging units, each having a different feature from the other within the kit. For example, a kit may include a plurality of wedging units, each exhibiting a different magnitude of biasing force, or each having a difference size, or each having different surfaces for the first and second members, or each having a specific spring-rate depending on specific need and user. The kit can further include a color coding system or other marking system to indicate the level of biasing force, the type of surface, the working range (i.e., range of motion of the first and second members), etc. for a given device. For example, one type of device may be colored red or have other type of indicia to indicate that it has a certain characteristic shared by all other so marked devices, such as a specific restoring force, working range, and/or tooth aggressiveness (e.g., size, number, configuration, of teeth) and other devices may have other indicia to indicate a different property or set of properties.

In some embodiments, the device may be provided and/or sold individually, or as a piece within several different types of kits. One type of kit might contain several essentially identical devices, to be used in conjunction with each other during an operation. A second type of kit may include a variety of differently structured devices that might be expected for use during the course of a particular surgery (i.e., for various functions throughout the surgery). For example, one type of device can be used to hold the incision site open, another type of device may be used to provide "tenting" (e.g., keep the path of the incision open), another type of device may be used near the leading edge of the incision, etc. Because patients/tissues/situations may differ from one operation to another, a third type of kit might contain several different types of devices that are color-coded and for which a surgeon could select from during an operation (e.g., if one type of device is too small then switch to a larger device, or if one type of device does not hold the tissue apart adequately then switch to a device that exerts more force, or if one type of device is slipping then switch to a device that has more aggressive teeth, etc.). It is further contemplated for the devices of a kit to be provided in an array, where each device of the array varies by a certain attribute (e.g., restoring force, tooth aggressiveness, etc.) so that during an operation the surgeon may quickly select a device that is suitable for the specific patient/tissues/situations.

A non-limiting example of using embodiments of the device may include creating an incision separating skin from other tissue to expose the underlying tissue and to form a subcutaneous pocket. The device may then be collapsed into a closed state. The device may then be inserted through the incision and into the subcutaneous pocket to position the device adjacent a leading dissection edge (e.g., an interface between skin and underlying tissue), allowing a biasing force of the device to prop the skin up and away from the underlying tissue and apply traction and counter-traction at a leading dissection edge so that retraction of the skin from the tissue can be facilitated during a surgical procedure. Further dissecting of the skin from the tissue at the leading dissection edge along a dissection path may be performed after the device is positioned into the subcutaneous pocket adjacent the leading dissection edge. While this further dissecting occurs, the device may further open by the first and second members moving away from each other to provide traction and counter traction during the further dissecting. Alternatively, the first member may be moved further away from the second member manually to further open the device to provide traction and counter-traction during further dissecting. Because the device can provide continuous traction and counter-traction, the skin can be continuously retracted as dissection separates the skin from the underlying tissue, thereby "propagating" the dissection edge along the desired dissection path.

Embodiments of the device can enable hands-free traction, counter-traction, and propping of the skin for a wide area of retraction, yet can be easily inserted through a small incision. Some devices can be made to have a light weight to enable handling and manipulation via one hand, freeing the other hand of a user for performing other functions. Use of embodiments of the device in accordance with the methods disclosed may provide a means for surgeons to perform complex surgeries through incisions that are sized and positioned to be more conducive for cosmesis without limiting the ability of the surgeon to perform the surgical procedure. For example, some devices can be configured as an intraoperative retracting device that may improve retraction and increase visualization of the dissection plane, which may decrease operating time, decrease thermal and mechanical injury, and improve ergonomics for the operating surgeon and the medical assistant.

While the device and methods may be described as being used to perform mastectomy surgeries, the various devices are certainly not limited to such procedures. Any procedure that may benefit from continued traction and counter-traction of two layers and/or body parts when separating the two layers and/or body parts may be an application for which the device and method could be used. These can include, but are not limited to, skin and soft tissue incisions (e.g., hernia incisions, appendectomies, etc.), transanal surgery, transluminal (e.g., polypectomies) surgery, intra-articular (e.g., joints, spine) surgery, head and neck surgery (e.g., thyroid, vascular), procedures on solid organs (e.g., liver), intraoral procedures, intra-abdominal retraction procedures, and/or vascular anastomosis procedures (e.g., to assist with intravascular retraction). The device may further be employed in existing spaces, or newly created spaces (e.g., may assist in creating space—via retraction and dissection). The device can be used to further optimize visualization of the incision and tissues. In some embodiments, leading edges of the device are splayed outward (corresponding to body shape), which may be done for intra-abdominal retraction. For example, the leading edges can be shaped as outwardly cupped retracting surfaces.

For the purposes of this disclosure the device will be described as having a proximal end and a distal end. The distal end of the device is the end that spearheads the insertion or the end that is most distal to the surgeon during placement and/or use of the device, whereas the proximal end of the device is the end that is closest to the surgeon during placement and/or use of the device. As will be explained in detail, some embodiments of the device may be used with the hinging unit or junction portion(s) as the distal end, and other embodiments of the device may be used with the first and second members as the distal end of the device. For clarity and uniformity, the device will be described by using the first and second members as the distal end unless explicitly described otherwise; however, it is understood that use of the device or any embodiment of the device can include the hinging unit or junction portion(s) as the distal end of the device. Further, it is contemplated that the device can use any portion as the distal end, as would be dictated by the surgical procedure, the desired function to be performed, and/or to merely expedite a surgical process.

In at least one embodiment, a method of retracting a first tissue from a second tissue can include creating an incision separating the first tissue from the second tissue to expose at least one of the first and second tissue and to form a tissue pocket. The method can further include collapsing a device into a closed state. The method can further include inserting at least a portion of the device through the incision and into the formed tissue pocket to position the device adjacent a leading dissection edge. The method can further include allowing a biasing force of the device to prop the first tissue up and away from the second tissue and apply traction and counter-traction after the device is inserted into the incision. The method can further include further dissecting the first tissue from the second tissue at the leading dissection edge along a dissection path after the device is positioned into the tissue pocket adjacent the leading dissection edge such that the device moves toward an open state via the biasing force during the further dissecting to apply traction and counter traction as the further dissecting is performed along the dissection path. The first tissue can include at least one of muscle tissue, nerve tissue, epithelial tissue, bone tissue, visceral tissue, organ tissue, glandular tissue, and connective tissue. The second tissue can include at least one of muscle tissue, nerve tissue, epithelial tissue, bone tissue, visceral tissue, organ tissue, glandular tissue, and connective tissue. The first tissue can be a different type of tissue than the second tissue.

In at least one embodiment, a method of retracting a first tissue from a second tissue can include creating an incision to expose a first/second tissue interface to create a tissue pocket within the first/second tissue interface, where at least a portion of the first/second tissue interface is a leading dissection edge. The method can further include grasping a device, where the device can include a first member having at least a first arm extending from the first member, a second member having at least a first arm extending from the second member. A distal end of the first arm of the first member may be connected to a first end member and a proximal end of the first arm of the first member may be connected to a proximal end of the first arm of the second member at a first junction. The distal end of the first arm of the second member can be connected to the second member. The first and second members may be at least one of statically, resiliently, and pivotally connected via the first junction such that the first member is moveable relative to the second member about the first junction. The first junction can be configured to provide a biasing force to move the first and second members away from each other to position the device in an open state. The first member can be movable relative to the second member about the first junction from the open state to a closed state. At least a portion of the first member can be abuttable with at least a portion of the second member when the device is in the closed state. The method can further include collapsing the device into the closed state. The method can further include inserting the device into the tissue pocket adjacent the leading dissection edge. The method can further include allowing the biasing force to move the device from the closed state toward an open state to prop the first tissue up and away from the second tissue and apply traction and counter-traction at the tissue pocket adjacent the leading dissection edge after the device is inserted into the tissue pocket. The method can further include further dissecting the first tissue from the second tissue adjacent the leading dissection edge while the device is in the tissue pocket to provide continuous traction and counter-traction as the leading dissection edge is propagated along a dissection path. Some embodiments can include allowing the device to move toward the open state via only the biasing force as the further dissecting is performed to provide the continuous traction and counter-traction as the leading dissection edge is propagated along the dissection path. Some embodiments can include the first tissue comprising epithelial tissue and the second tissue is one of muscle tissue, nerve tissue, and connective tissue. With some embodiments, positioning the device can further include placing at least one of the first cross-beam and the second cross-beam adjacent the leading dissection edge. With some embodiments, positioning the device can further include placing at least one of the first junction and the second junction adjacent the leading dissection edge.

With some embodiments, further dissecting of the skin from the tissue can include viewing the leading dissection edge through an opening of the device and performing the further dissecting through the opening. With some embodiments, the first arm of the first member extends from the first member adjacent a first side of the first member and the first member has a second arm extending from adjacent a second side of the first member that is opposite the first side of the first member. At least one of a first cross member and a first plate may span between the first and second sides of the first member. The first arm of the second member extending from the second member adjacent a first side of the second member and the second member may have a second arm extending from adjacent a second side of the second member that is opposite the first side of the second member. At least one of a second cross member and a second plate may span between the first and second sides of the second member. A distal end of the second arm of the first member can be attached to at least one of the plate and the cross member of the first member adjacent the second side of the first member. With some embodiments, a distal end of the second arm of the second member can be attached to at least one of the plate and the cross member of the second member adjacent the second side of the second member. Further, a proximal end of the second arm of the first member can be attached to a proximal end of the second arm of the second member at a second junction such that the first member is movable relative to the second member about the first junction and the second junction from the open state to the closed state.

Some embodiments can include an outer-facing surface of at least one of the first member, the second member, the first cross-beam, the second cross-beam, the first plate. The second plate may have a gripping structure. Some embodiments can include an inner-facing surface of at least one of the first member, the second member, the first cross-beam, the second cross-beam. The first plate and the second plate may have at least one finger retainer. Some embodiments can include at least one of the first member and the second member having a plurality of spaced apart flexible or resilient planks extending to a distal end of the device opposite a proximal end of the device. The first junction may define the proximal end of the device or be located adjacent the proximal end of the device.

Some embodiments can include the first arm of the first member extending from the first member adjacent a first side of the first member and the first member has a second arm extending from adjacent the first side of the first member and a third arm extending from adjacent the first side of the first member. The first member may also have fourth, fifth and sixth arms that extend from a second side of the first member that is opposite the first side of the first member. The second arm of the first member may be located between the first and third arms of the first member, and the fifth arm of the first member can be located between the fourth and sixth arms of the first member. The first arm of the first member may be aligned with the fourth arm of the first member. The second arm of the first member may be aligned with the fifth arm of the first member. The third arm of the first member may be aligned with the sixth arm of the first member. The first arm of the second member extending from the second member adjacent a first side of the second member and the second member can have a second arm extending from adjacent the first side of the second member and a third arm extending from adjacent the first side of the second member. The second member may also have fourth, fifth and sixth arms that extend from a second side of the second member that is opposite the first side of the second member. The second arm of the second member may be located between the first and third arms of the second member. The fifth arm of the second member may be located between the fourth and sixth arms of the second member. The first arm of the second member may be aligned with the fourth arm of the second member. The second arm of the second member may be aligned with the fifth arm of the second member. The third arm of the second member may be aligned with the sixth arm of the second member. Distal ends of the second arm, third arm, fourth arm, fifth arm, and sixth arm of the first member can be attached to at least one of a first plate and a first cross member of the first member. Distal ends of the second arm, third arm, fourth arm, fifth arm, and sixth arm of the second member can be attached to at least one of a second plate and a second cross member of the second member. A proximal end of the second arm of the first member may be attached to a proximal end of the second arm of the second member at a second junction. A proximal end of the third arm of the first member can be attached to a proximal end of the third arm of the second member at a third junction such that the second junction is between the first and third junctions. A proximal end of the fourth arm of the first member can be attached to a proximal end of the fourth arm of the second member at a fourth junction. A proximal end of the fifth arm of the first member can be attached to a proximal end of the fifth arm of the second member at a fifth junction. A proximal end of the sixth arm of the first member can be attached to a proximal end of the sixth arm of the second member at a sixth junction such that the fifth junction is between the fourth and sixth junctions. The first member can be movable relative to the second member between the open state and the closed state about the first junction, second junction, third junction, fourth junction, fifth junction and sixth junction.

Some embodiments can include a holding mechanism to selectively lock the device in the closed state. Some embodiments can include a tenting apparatus. Some embodiments can include a vacuum conduit.

In at least one embodiment, a retractor and prop device can include a first member having at least a first arm extending from the first member. Some embodiments can include a second member having at least a first arm extending from the second member. A distal end of the first arm of the first member may be connected to a first end member and a proximal end of the first arm of the first member may be connected to a proximal end of the first arm of the second member at a first junction. The distal end of the first arm of the second member can be connected to the second member. The first and second members may be at least one of statically, resiliently, and pivotally connected via the first junction such that the first member is moveable relative to the second member about the first junction. The first junction can be configured to provide a biasing force to move the first and second members away from each other to position the device in an open state. The first member can be movable relative to the second member about the first junction from the open state to a closed state. At least a portion of the first member may be abuttable with at least a portion of the second member when the device is in the closed state.

With some embodiments the first member can include a first side section and a second side section conjoined by at least one of a first cross member and a first plate. The second member may include a first side section and a second side section conjoined by at least one of a second cross member and a second plate.

Some embodiments can include the first arm of the first member extending from the first member adjacent a first side of the first member and the first member has a second arm extending from adjacent the first side of the first member and a third arm extending from adjacent the first side of the first member. The first member may also have fourth, fifth and sixth arms that extend from a second side of the first member that is opposite the first side of the first member. The second arm of the first member may be located between the first and third arms of the first member, and the fifth arm of the first member can be located between the fourth and sixth arms of the first member. The first arm of the first member may be aligned with the fourth arm of the first member. The second arm of the first member may be aligned with the fifth arm of the first member. The third arm of the first member may be aligned with the sixth arm of the first member. The first arm of the second member extending from the second member adjacent a first side of the second member and the second member can have a second arm extending from adjacent the first side of the second member and a third arm extending from adjacent the first side of the second member. The second member may also have fourth, fifth and sixth arms that extend from a second side of the second member that is opposite the first side of the second member. The second arm of the second member may be located between the first and third arms of the second member. The fifth arm of the second member may be located between the fourth and sixth arms of the second member. The first arm of the second member may be aligned with the fourth arm of the second member. The second arm of the second member may be aligned with the fifth arm of the second member. The third arm of the second member may be aligned with the sixth arm of the second member. Distal ends of the second arm, third arm, fourth arm, fifth arm, and sixth arm of the first member can be attached to at least one of a first plate and a first cross member of the first member. Distal ends of the second arm, third arm, fourth arm, fifth arm, and sixth arm of the second member can be attached to at least one of a second plate and a second cross member of the second member. A proximal end of the second arm of the first member may be attached to a proximal end of the second arm of the second member at a second junction. A proximal end of the third arm of the first member can be attached to a proximal end of the third arm of the second member at a third junction such that the second junction is between the first and third junctions. A proximal end of the fourth arm of the first member can be attached to a proximal end of the fourth arm of the second member at a fourth junction. A proximal end of the fifth arm of the first member can be attached to a proximal end of the fifth arm of the second member at a fifth junction. A proximal end of the sixth arm of the first member can be attached to a proximal end of the sixth arm of the second member at a sixth junction such that the fifth junction is between the fourth and sixth junctions. The first member can be movable relative to the second member between the open state and the closed state about the first junction, second junction, third junction, fourth junction, fifth junction and sixth junction With some embodiments, at least one of a first cross member and a first plate extend from between the first side of the first member to the second side of the first member. The second member can include at least one of a second cross member and a second plate that extend from between the first side of the second member to the second side of the second member.

In some embodiments, a retractor and prop device includes a first member and a second member. The first and second members can be moveable relative to each other about at least one junction. Each junction can be configured to at least one of statically, resiliently, and pivotally connect the first and second members together such that the first member is movable relative to the second member via motion about the at least one junction. Each junction can be configured to provide a biasing force to move the first and second members away from each other to position the device in an open state. The first member can be movable relative to the second member about the at least one junction from the open state to a closed state.

In some embodiments of the retractor and prop device, a first U-shaped member is positioned adjacent a first side of the first member and a first side of the second member. The first U-shaped member has a first end, a second end and a first apex between the first and second ends. The first end of the first U-shaped member extends from the proximal side of the first member and the second end of the first U-shaped member extends from the proximal side of the second member. A second U-shaped member is positioned adjacent the first side of the first member and the first side of the second member. The second U-shaped member has a first end, a second end, and an apex between the first and second ends. The first end of the second U-shaped member extends from the distal side of the first member and the second end of the second U-shaped member extends from the distal side of the second member. A third U-shaped member is positioned adjacent a second side of the first member and a second side of the second member. The second side of the second member is opposite the first side of the second member. The second side of the first member is opposite the first side of the first member. The third U-shaped member can have a first end, a second end and an apex between the first and second ends where the first end of the third U-shaped member extends from the proximal end of the first member and the second end of the third U-shaped member extends from the proximal end of the second member. A fourth U-shaped member positioned adjacent the second side of the first member and the second side of the second member. The fourth U-shaped member can have a first end, a second end, and an apex between the first and second ends. The first end of the fourth U-shaped member can extend from the distal end of the first member and the second end of the fourth U-shaped member can extend from the distal end of the second member. The apex of the first U-shaped member can be coupled to the apex of the second U-shaped member to define a first junction of the at least one junction and the apex of the third U-shaped member can be coupled to the apex of the fourth U-shaped member to define a second junction of the at least one junction. The first member and second member can be moveable toward each other to the closed state and moveable away from each other to the open state. The first, second, third, and fourth U-shaped members can be configured to bias the first and second members to move away from each toward the open state via motion about the first and second junctions.

Some embodiments of the retractor and prop device can include a first arm extending from a proximal end of the first member to a distal end of the first arm and a second arm extending from a proximal end of the second member to a distal end of the second arm. The distal end of the first arm can be connected to the distal end of the second arm at a first junction of the at least one junction. The first junction can be configured to provide a biasing force to move the first and second members away from each other to position the device in the open state. The first member can have at least one of a clamp and a finger retainer and the second member can also have at least one of a clamp and a finger retainer. Embodiments of the device can also include a third arm extending from the proximal end of the first member to a distal end of the third arm, a fourth arm extending from the proximal end of the first member to a distal end of the fourth arm, a fifth arm extending from the proximal end of the second member to a distal end of the fifth arm, and a sixth arm extending from the proximal end of the second member to a distal end of the sixth arm. The distal end of the third arm can be connected to the distal end of the fifth arm at a second junction of the at least one junction such that the second junction at least one of statically, resiliently, and pivotally connects the first and second members so that the first member is moveable relative to the second member about the second junction. The distal end of the fourth arm can be connected to the distal end of the sixth arm at a third junction of the at least one junction such that the third junction at least one of statically, resiliently, and pivotally connects the first and second members so that the first member is moveable relative to the second member about the third junction. The second junction can be between the first and third junctions and the second junction can be spaced apart from the first junction and is spaced apart from the third junction.

The closed state of the device can be any of a number of different configurations. For instance, the closed state can be configured such that at least a portion of the first member is abuttable with at least a portion of the second member when the device is in the closed state. As another example, the first and second members can be closer to each other when the device is in the closed state as compared to when the device is in the open state.

Some embodiments of the device can include a first arm, a second arm, and a third arm extending from adjacent a first side of the first member to adjacent a first side of the second member such that the second arm is located between the first and third arms and can also include a fourth arm, fifth arm and sixth arm extending from adjacent a second side of the first member to adjacent a second side of the second member (the second side of the first member can be opposite the first side of the first member and the second side of the second member can be opposite the first side of the second member). The fifth arm can be located between the fourth and sixth arms and the first arm can be aligned with the fourth arm, the second arm can be aligned with the fifth arm and the third arm can be aligned with the sixth arm. An intermediate portion of the first arm can define a first junction, an intermediate portion of the second arm can define a second junction, an intermediate portion of the third arm can define a third junction, an intermediate portion of the fourth arm can define a fourth junction, an intermediate portion of the fifth arm can define a fifth junction, and an intermediate portion of the sixth arm can define a sixth junction. The second junction can be located between the first and third junctions, the fifth junction may be located between the fourth and sixth junctions; the fifth junction can be aligned with the second junction, the first junction can be aligned with the fourth junction and the third junction can be aligned with the sixth junction. The first member can be movable relative to the second member between the open state and the closed state about the first junction, second junction, third junction, fourth junction, fifth junction and sixth junction. At least one of a first cross member and a first plate can extend from between the first side of the first member to the second side of the first member and at least one of a second cross member and a second plate can extend from between the first side of the second member to the second side of the second member.

In some embodiments, the first member can have a proximal end and a distal end and the first member can have a first arm extending from the proximal end of the first member. A second member can have a proximal end and a distal end, and a second arm extending from the proximal end of the second member. A distal end of the first member arm can be connected to a distal end of the second member arm at a junction. At least one of the first member and the second member can have teeth for contacting tissue. At least one of the first member and the second member can define at least one recess for receiving at least one finger. The first member, first arm, second member, second arm, and the junction can be portions of a unitary structure molded from a resilient material (e.g. injection molded from polymeric material or elastomeric material, molded from a resilient metal, three dimensional printing of the device, etc.). The device can have a generally U-shape or a generally C-shape in some embodiments.

Kits can also include multiple devices. Each device can be the same or the kit may include different embodiments of the device. Kits can include any combination of embodiments of the retractor and prop device disclosed herein. The devices can be colored differently or have a particular set of indicia in accordance with an indicia scheme to identify one or more properties that differ between those devices (e.g. biasing force for biasing each device to its open state, use in a different body part or for a different function of a surgical procedure, etc.).

In one embodiment, a method of retracting a first tissue from a second tissue can include creating an incision separating the first tissue from the second tissue to expose at least one of the first and second tissue and to form a tissue pocket, collapsing a first device into a closed state, inserting at least a portion of the first device when in the closed state of the first device through the incision to position the first device adjacent a leading dissection edge, allowing a biasing force of the first device to prop the first tissue and the second tissue away from each other and apply traction and counter-traction after the first device is inserted into the incision, and further dissecting the first tissue from the second tissue at the leading dissection edge along a dissection path after the first device is positioned into the tissue pocket adjacent the leading dissection edge such that the first device moves toward an open state via the biasing force during the further dissecting to apply traction and counter traction as the further dissecting is performed along the dissection path. The method may further include the first tissue comprising at least one of muscle tissue, nerve tissue, epithelial tissue, bone tissue, visceral tissue, organ tissue, glandular tissue, and connective tissue and the second tissue comprising at least one of muscle tissue, nerve tissue, epithelial tissue, bone tissue, visceral tissue, organ tissue, glandular tissue, and connective tissue.

The method may further include collapsing a second device into a closed state, inserting at least a portion of the second device when in the closed state of the second device into a tissue pocket formed adjacent the incision, and allowing a biasing force of the second device to prop the first tissue and the second tissue away from each other and apply traction and counter-traction after the second device is inserted into the tissue pocket. In some embodiments, the first device and the second device may be components of a kit, the first device having a first indicia and the second device having a second indicia, the first indicia being different than the second indicia. The first indicia can indicate at least one property of the first device. The second indicia can indicate at least one property of the second device. The at least one property of the first device may differ from the at least one property of the second device. The method may further include collapsing a third device into a closed state, inserting at least a portion of the third device into the incision when the third device is in the closed state of the third device, and allowing a biasing force of the third device to prop the first tissue up and away from the second tissue and apply traction and counter-traction after the third device is inserted into the incision. In some embodiments, the first device, second device, and third device may be components of a kit, where the first device may have a first indicia, the second device may have a second indicia, and the third device may have a third indicia. The first indicia can be different than the second indicia, and the third indicia can be different than the first indicia and also being different than the second indicia. The first indicia may indicate at least one property of the first device. The second indicia may indicate at least one property of the second device that differs from the at least one property of the second device. The third indicia may indicate at least one property of the third device that differs from the at least one property of the second device and also differs from the at least one property of the first device.

The method may further include collapsing a second device into a closed state, inserting at least a portion of the second device into the incision at a location that is spaced apart from the first device when the second device is in the closed state of the second device, and allowing a biasing force of the second device to prop the first tissue and the second tissue away from each other and apply traction and counter-traction after the second device is inserted into the incision.

In some embodiments, the first device may include a first member having at least a first arm extending from the first member, a second member having at least a first arm extending from the second member, wherein a distal end of the first arm of the first member can be connected to a first end member and a proximal end of the first arm of the first member can be connected to a proximal end of the first arm of the second member at a first junction. The distal end of the first arm of the second member can be connected to the second member. The first and second members can be at least one of statically, resiliently, and pivotally connected via the first junction such that the first member is moveable relative to the second member about the first junction. The first junction may be configured to provide a biasing force to move the first and second members away from each other to position the device in an open state. The first member may be movable relative to the second member about the first junction from the open state to a closed state.

The method may further include allowing the first device to move toward the open state via only the biasing force as the further dissecting is performed to provide the continuous traction and counter-traction as the leading dissection edge is propagated along the dissection path. At least one of: at least a portion of the first member can be abuttable with at least a portion of the second member when the device is in the closed state; and the distal end of the first arm of the first member can be a first distance away from the distal end of the first arm of the second member when the first device is in the closed stated and the distal end of the first arm of the first member being a second distance away from the distal end of the first arm of the second member when the first device is in the open state, where the first distance can be less than the second distance. In some embodiments, the first tissue can include epithelial tissue and the second tissue is one of muscle tissue, nerve tissue, bone tissue, visceral tissue, organ tissue, glandular tissue, and connective tissue. The first device may be configured to perform at least one of: holding the incision open, keeping the dissection path open via tenting, and applying retraction at or adjacent the incision. In some embodiments, positioning the device can further include placing at least one of the first cross-beam and the second cross-beam adjacent the leading dissection edge. In some embodiments, positioning the first device may further include placing the first junction adjacent the leading dissection edge. In some embodiments, the further dissecting of the skin from the tissue can include viewing the leading dissection edge through an opening of the first device and performing the further dissecting through the opening.

In some embodiments, the first arm of the first member can extend from the first member adjacent a first side of the first member and the first member has a second arm extending from adjacent a second side of the first member that is opposite the first side of the first member, wherein at least one of a first cross member and a first plate span between the first and second sides of the first member. The first arm of the second member can extend from the second member adjacent a first side of the second member and the second member has a second arm extending from adjacent a second side of the second member that is opposite the first side of the second member, wherein at least one of a second cross member and a second plate span between the first and second sides of the second member. A distal end of the second arm of the first member can be attached to at least one of the plate and the cross member of the first member adjacent the second side of the first member. A distal end of the second arm of the second member can be attached to at least one of the plate and the cross member of the second member adjacent the second side of the second member. A proximal end of the second arm of the first member may be attached to a proximal end of the second arm of the second member at a second junction such that the first member is movable relative to the second member about the first junction and the second junction from the open state to the closed state.

In some embodiments, an outer-facing surface of at least one of the first member, the second member, the first cross-beam, the second cross-beam, the first plate and the second plate can have a gripping structure. In some embodiments, an inner-facing surface of at least one of the first member, the second member, the first cross-beam, the second cross-beam, and the first plate and the second plate can have at least one finger retainer. In some embodiments, at least one of the first member and the second member has a plurality of spaced apart flexible planks extending to a distal end of the device opposite a proximal end of the device. The first junction may define the proximal end of the device or being located adjacent the proximal end of the device.

In some embodiments, the first arm of the first member can extend from the first member adjacent a first side of the first member and the first member has a second arm extending from adjacent the first side of the first member and a third arm extending from adjacent the first side of the first member, the first member also having fourth, fifth and sixth arms that extend from a second side of the first member that is opposite the first side of the first member, the second arm of the first member being located between the first and third arms of the first member and the fifth arm of the first member being located between the fourth and sixth arms of the first member, the first arm of the first member being aligned with the fourth arm of the first member, the second arm of the first member being aligned with the fifth arm of the first member and the third arm of the first member being aligned with the sixth arm of the first member. The first arm of the second member can extend from the second member adjacent a first side of the second member and the second member has a second arm extending from adjacent the first side of the second member and a third arm extending from adjacent the first side of the second member, the second member also having fourth, fifth and sixth arms that extend from a second side of the second member that is opposite the first side of the second member, the second arm of the second member being located between the first and third arms of the second member and the fifth arm of the second member being located between the fourth and sixth arms of the second member, the first arm of the second member being aligned with the fourth arm of the second member, the second arm of the second member being aligned with the fifth arm of the second member and the third arm of the second member being aligned with the sixth arm of the second member. Distal ends of the second arm, third arm, fourth arm, fifth arm, and sixth arm of the first member can be attached to at least one of a first plate and a first cross member of the first member. Distal ends of the second arm, third arm, fourth arm, fifth arm, and sixth arm of the second member can be attached to at least one of a second plate and a second cross member of the second member. A proximal end of the second arm of the first member can be attached to a proximal end of the second arm of the second member at a second junction. A proximal end of the third arm of the first member can be attached to a proximal end of the third arm of the second member at a third junction such that the second junction is between the first and third junctions. A proximal end of the fourth arm of the first member can be attached to a proximal end of the fourth arm of the second member at a fourth junction. A proximal end of the fifth arm of the first member can be attached to a proximal end of the fifth arm of the second member at a fifth junction. A proximal end of the sixth arm of the first member can be attached to a proximal end of the sixth arm of the second member at a sixth junction such that the fifth junction is between the fourth and sixth junctions. The first member may be movable relative to the second member between the open state and the closed state about the first junction, second junction, third junction, fourth junction, fifth junction and sixth junction.

In some embodiments, the first device can further include a holding mechanism to selectively lock the device in the closed state. In some embodiments, the first device can further include a tenting apparatus. In some embodiments, the first device can further include a vacuum conduit.

In some embodiments, the first device can include a first member having a distal side and a proximal side and a second member having a distal side and a proximal side. The first device can further include a first U-shaped member position adjacent a first side of the first member and a first side of the second member, the first U-shaped member having a first end, a second end and an first apex between the first and second ends, the first end of the first U-shaped member extending from the proximal side of the first member and the second end of the first U-shaped member extending from the proximal side of the second member. The first device can further include a second U-shaped member positioned adjacent the first side of the first member and the first side of the second member, the second U-shaped member having a first end, a second end, and an apex between the first and second ends, the first end of the second U-shaped member extending from the distal side of the first member and the second end of the second U-shaped member extending from the distal side of the second member. The first device can further include a third U-shaped member positioned adjacent a second side of the first member and a second side of the second member, the second side of the second member being opposite the first side of the second member, the second side of the first member being opposite the first side of the first member, the third U-shaped member having a first end, a second end and an apex between the first and second ends, the first end of the third U-shaped member extending from the proximal end of the first member and the second end of the third U-shaped member extending from the proximal end of the second member. The first device can further include a fourth U-shaped member positioned adjacent the second side of the first member and the second side of the second member, the fourth U-shaped member having a first end, a second end, and an apex between the first and second ends, the first end of the fourth U-shaped member extending from the distal end of the first member and the second end of the fourth U-shaped member extending from the distal end of the second member. The apex of the first U-shaped member may be coupled to the apex of the second U-shaped member and the apex of the third U-shaped member being coupled to the apex of the fourth U-shaped member. The first member and the second member can be moveable toward each other to the closed state and moveable away from each other to the open state, the first, second, third, and fourth U-shaped members being configured to bias the first and second members to move away from each toward the open state.

In some embodiments, the first device can include a first member having a proximal end and a distal end, the first member having a first arm extending from the proximal end of the first member. The first device can further include a second member having a proximal end and a distal end, the second member having a second arm extending from the proximal end of the second member. A distal end of the first member arm can be connected to a distal end of the second member arm at a junction. At least one of the first member and the second member can have teeth for contacting tissue. At least one of the first member and the second member may define at least one recess for receiving at least one finger. The first member, first arm, second member, second arm, and the junction may be portions of a unitary structure molded from a resilient material.

In some embodiments, the first device can include a first member, a first arm extending from a proximal end of the first member to a distal end of the first arm, a second member, and a second arm extending from a proximal end of the second member to a distal end of the second arm. The distal end of the first arm may be connected to the distal end of the second arm at a first junction, the first junction at least one of statically, resiliently, and pivotally connecting the first and second members so that the first member is moveable relative to the second member about the first junction. The first junction can be configured to provide a biasing force to move the first and second members away from each other to position the device in the open state. The first member may have one of a clamp and a finger retainer and the second member has one of a clamp and a finger retainer.

In some embodiments, the method may further include a device where a third arm extending from the proximal end of the first member to a distal end of the third arm, a fourth arm extending from the proximal end of the first member to a distal end of the fourth arm, a fifth arm extending from the proximal end of the second member to a distal end of the fifth arm, and a sixth arm extending from the proximal end of the second member to a distal end of the sixth arm. The distal end of the third arm may be connected to the distal end of the fifth arm at a second junction, the second junction at least one of statically, resiliently, and pivotally connecting the first and second members so that the first member is moveable relative to the second member about the second junction. The distal end of the fourth arm can be connected to the distal end of the sixth arm at a third junction, the third junction at least one of statically, resiliently, and pivotally connecting the first and second members so that the first member is moveable relative to the second member about the third junction. The second junction may be between the first and third junctions and the second junction can be spaced apart from the first junction and is also spaced apart from the third junction.

In one embodiment, retractor and prop device can include a first member and a second member. The first and second members can be moveable relative to each other about at least one junction. Each junction may be configured to at least one of statically, resiliently, and pivotally connect the first and second members together such that the first member is movable relative to the second member via motion about the at least one junction. Each junction may be further configured to provide a biasing force to move the first and second members away from each other to position the device in an open state. The first member can be movable relative to the second member about the at least one junction from the open state to a closed state.

The device may further include a first U-shaped member position adjacent a first side of the first member and a first side of the second member. The first U-shaped member may have a first end, a second end and an first apex between the first and second ends, the first end of the first U-shaped member extending from the proximal side of the first member and the second end of the first U-shaped member extending from the proximal side of the second member. The device may further include a second U-shaped member positioned adjacent the first side of the first member and the first side of the second member. The second U-shaped member may have a first end, a second end, and an apex between the first and second ends, the first end of the second U-shaped member extending from the distal side of the first member and the second end of the second U-shaped member extending from the distal side of the second member. The device may further include a third U-shaped member positioned adjacent a second side of the first member and a second side of the second member. The second side of the second member can be opposite the first side of the second member. The second side of the first member can be opposite the first side of the first member. The third U-shaped member may have a first end, a second end and an apex between the first and second ends. The first end of the third U-shaped member can extend from the proximal end of the first member and the second end of the third U-shaped member extending from the proximal end of the second member. The device may further include a fourth U-shaped member positioned adjacent the second side of the first member and the second side of the second member. The fourth U-shaped member can have a first end, a second end, and an apex between the first and second ends. The first end of the fourth U-shaped member can extend from the distal end of the first member and the second end of the fourth U-shaped member can extend from the distal end of the second member. The apex of the first U-shaped member can be coupled to the apex of the second U-shaped member to define a first junction of the at least one junction and the apex of the third U-shaped member can be coupled to the apex of the fourth U-shaped member to define a second junction of the at least one junction. The first member and the second member may be moveable toward each other to the closed state and moveable away from each other to the open state. The first, second, third, and fourth U-shaped members can be configured to bias the first and second members to move away from each toward the open state via motion about the first and second junctions.

In some embodiments, a first arm can extend from a proximal end of the first member to a distal end of the first arm. A second arm can extend from a proximal end of the second member to a distal end of the second arm. The distal end of the first arm may be connected to the distal end of the second arm at a first junction of the at least one junction. The first junction may be configured to provide a biasing force to move the first and second members away from each other to position the device in the open state. In some embodiments, the first member may have one of a clamp and a finger retainer and the second member has one of a clamp and a finger retainer.

In some embodiments, the device can include a third arm extending from the proximal end of the first member to a distal end of the third arm, a fourth arm extending from the proximal end of the first member to a distal end of the fourth arm, a fifth arm extending from the proximal end of the second member to a distal end of the fifth arm, and a sixth arm extending from the proximal end of the second member to a distal end of the sixth arm. The distal end of the third arm may be connected to the distal end of the fifth arm at a second junction of the at least one junction, the second junction at least one of statically, resiliently, and pivotally connecting the first and second members so that the first member is moveable relative to the second member about the second junction. The distal end of the fourth arm may be connected to the distal end of the sixth arm at a third junction of the at least one junction, the third junction at least one of statically, resiliently, and pivotally connecting the first and second members so that the first member is moveable relative to the second member about the third junction. The second junction may be between the first and third junctions and the second junction can be spaced apart from the first junction and is spaced apart from the third junction.

In some embodiments, at least one of: at least a portion of the first member can be abuttable with at least a portion of the second member when the device is in the closed state, and the first and second members may be closer to each other when the device is in the closed state as compared to when the device is in the open state.

In some embodiments, the first member can include a first side and a second side conjoined by at least one of a first cross member and a first plate. The second member may include a first side and a second side conjoined by at least one of a second cross member and a second plate.

In some embodiments, the device can include a first arm, a second arm, and a third arm extending from adjacent a first side of the first member to adjacent a first side of the second member; the second arm being located between the first and third arms. The device can further include a fourth arm, fifth arm and sixth arm extending from adjacent a second side of the first member to adjacent a second side of the second member, the second side of the first member being opposite the first side of the first member, the second side of the second member being opposite the first side of the second member. The fifth arm can be located between the fourth and sixth arms. The first arm can be aligned with the fourth arm. The second arm can be aligned with the fifth arm and the third arm being aligned with the sixth arm. An intermediate portion of the first arm can define a first junction, an intermediate portion of the second arm can define a second junction, an intermediate portion of the third arm can define a third junction, an intermediate portion of the fourth arm can define a fourth junction, an intermediate portion of the fifth arm can define a fifth junction, and an intermediate portion of the sixth arm can define a sixth junction. The second junction may be located between the first and third junctions. The fifth junction can be located between the fourth and sixth junctions. The fifth junction can be aligned with the second junction. The first junction can aligned with the fourth junction. The third junction can be aligned with the sixth junction. The first member may be movable relative to the second member between the open state and the closed state about the first junction, second junction, third junction, fourth junction, fifth junction and sixth junction.

In some embodiments, at least one of a first cross member and a first plate extend from between the first side of the first member to the second side of the first member. Further, the second member can include at least one of a second cross member and a second plate that extend from between the first side of the second member to the second side of the second member.

In some embodiments, the first member may have a proximal end and a distal end, the first member having a first arm extending from the proximal end of the first member.

The second member may have a proximal end and a distal end, the second member having a second arm extending from the proximal end of the second member. A distal end of the first member arm may be connected to a distal end of the second member arm at a junction. At least one of the first member and the second member can have teeth for contacting tissue. At least one of the first member and the second member can define at least one recess for receiving at least one finger. The first member, first arm, second member, second arm, and the junction can be portions of a unitary structure molded from a resilient material.

In some embodiments, the device may have a generally U-shape or a generally C-shape.

In some embodiments, the first member can have a first end and a second end and a clamp disposed between the first end and the second end. The second member can have a first end and a second end with a clamp disposed between the first end and the second end. The device may further include a seal attached to the clamp of the first member and the clamp of the second member such that the seal is positionable for contacting tissue of a patient along an outer perimeter of the seal or an inner perimeter of the seal. The seal may be an annular shaped member.

The device may further include a membrane attached to the seal, the membrane configured to bridge an incision opening to create a seal between a surgical space inside of a patient and the seal.

In some embodiments, a kit of a plurality of retractor and prop devices for use in at least one surgical procedure may include a first device and a second device, where the first device and the second device may be any of the retractor and prop devices described herein. In some embodiments, the first device can have a first indicia and the second device can have a second indicia that differs from the first indicia to indicate at least one property of the second device differs from at least one property of the first device. The first indicia may be a first color and the second indicia may be a second color. The kit can further include a third device having a third indicia indicating at least one property of the third device that differs from the at least one property of the second device and also differs from the at least one property of the first device. The third device can be any of the retractor and prop devices of described herein.

In some embodiments, a kit can include a first device having a first indicia indicating a first characteristic of the first device, and said second device having a second indicia indicating a second characteristic of the second device. The first indicia and the second indicia may be either essentially the same, or different. The first characteristic can be different than the second characteristics and the first and second indicia may be different. The first characteristic may be related to facilitating a step of a surgical procedure. The second characteristic may be related to facilitating a step of the surgical procedure. The first characteristic may be one of holding an incision open, holding a dissection path open, and applying retraction at the incision and the second characteristic is one of holding an incision open, holding a dissection path open, and applying retraction at the incision. A first device may be configured for holding an incision open. A second device may be configured for holding a dissection path open. A third device may be configured for applying retraction at the incision.

In some embodiments, a method of performing surgery can include creating an incision separating first tissue from second tissue to form an incision, collapsing a first device into a closed state, inserting at least a portion of the first device into the incision when the first device is in the closed state, and allowing a biasing force of the first device to perform at least one of: holding the incision open, keeping a dissection path open via tenting, and applying retraction at or adjacent the incision.

In some embodiments, the allowing of the biasing force of the first device can hold the incision open, and the method can further include attaching a seal to the first device such that the seal in contacts at least one of the first tissue and the second tissue to facilitate laparoscopic surgery. The seal may be an annular shaped structure that contacts the first tissue and second tissue to seal the incision to define an opening of the incision.

In some embodiments, the method can include positioning a member adjacent the seal. Further, the allowing of the biasing force of the first device may keep the dissection path open via tenting. Further, the allowing of the biasing force of the first device can also apply retraction at or adjacent the incision. Further, the allowing of the biasing force of the first device can apply retraction at or adjacent the incision. The first device can be any of the retractor and prop devices of described herein.

In some embodiments, the allowing of the biasing force of the first device can hold the incision open, and method can also include collapsing a second device into a closed state, inserting at least a portion of the second device into the incision when the second device is in the closed state, and allowing a biasing force of the second device to perform at least one of: keeping a dissection path open via tenting and applying retraction at or adjacent the incision.

In some embodiments, the method can include collapsing a third device into a closed state, inserting at least a portion of the third device into the incision when the third device is in the closed state, allowing a biasing force of the third device to perform at least one of: keeping a dissection path open via tenting and applying retraction at or adjacent the incision.

While these potential advantages are made possible by technical solutions offered herein, they are not required to be achieved. The presently disclosed device and method can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE FIGURES

The above and other objects, aspects, features, advantages and possible applications of the present invention will be more apparent from the following more particular description thereof, presented in conjunction with the following drawings. Like reference numbers used in the drawings may identify like components.

FIG. 52 is a flow chart describing an exemplary method of using at least one embodiment of the device in a surgical procedure.

FIG. 53 is a flow chart illustrating an exemplary method of using at least one embodiment of the device in a surgical procedure.

DETAILED DESCRIPTION OF THE INVENTION

Figure 1:
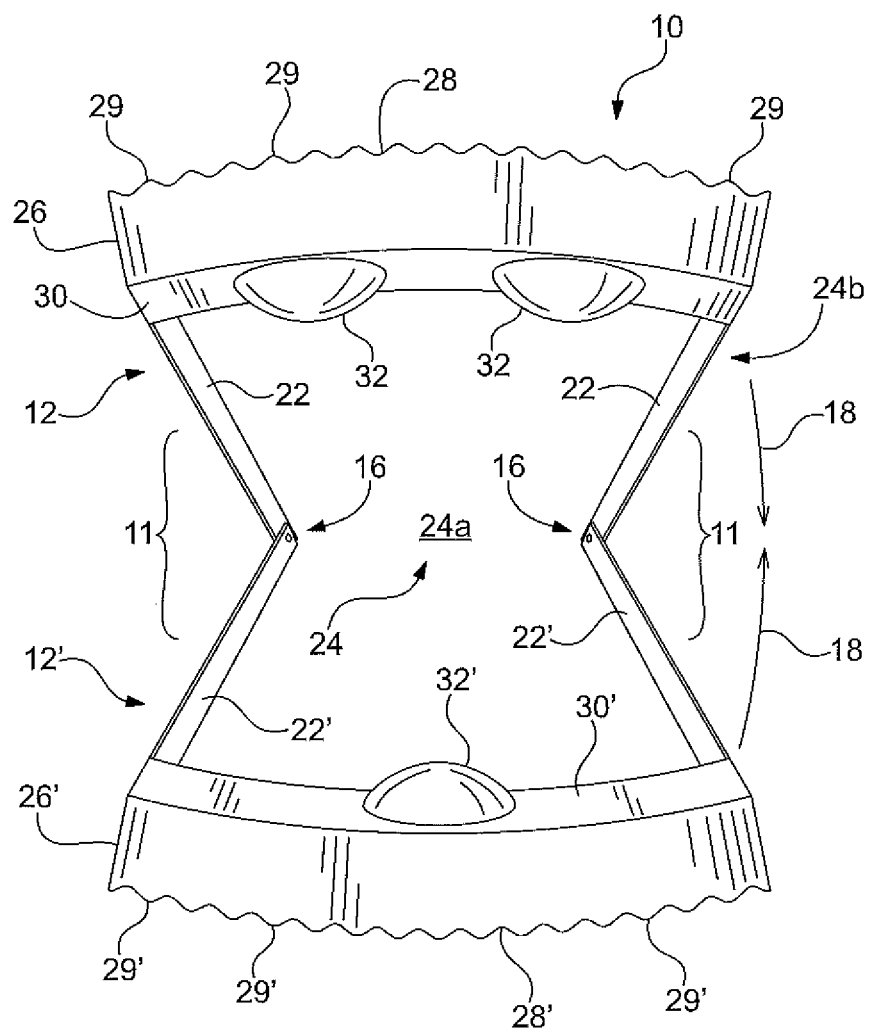
FIG. 1 is a perspective of an exemplary embodiment of the device with a first U-shaped member statically connected to a second U-shaped member to facilitate a resilient connection that provides a biasing force for biasing the first U-shaped member away from the second U-shaped member.

The device 10 can include a wedging unit that has at least one first member 12 connected to at least one second member 12' via at least one hinging unit 11. A first member 12 can exhibit various shapes and configurations. A second member 12' can exhibit various shapes and configurations. A second member 12' can have a same or similar shape and configuration as that of any first member 12 or a different shape and configuration of that of any first member 12. With some embodiments, a first member 12 may have a same length, width, and/or thickness as that of a second member 12'. In other embodiments, at least one of the length, width, and/or thickness differs between a first member 12 and a second member 12'. For example, a first member 12 can have a length that is greater than a length of a second member 12'. This may be done to generate an offset (or length disparity) in the members 12, 12' of the device to accommodate a particular type of surgery or perform a certain type of function (see FIG. 6 where the first member 12 is illustrated as having a longer length than that of the second member 12'). A first member 12 and/or a second member 12' can be a U-shaped, rectangular, square, triangular, hexagonal, V-shaped, C-shaped, D-shaped, Y-shaped, L-shaped, or exhibit other shapes. Furthermore, an aspect ratio (the ratio of width to height) of any member 12, 12' may vary from linear to spherical. It is contemplated for the aspect ratio to accommodate an intended use and to further accommodate the surfaces (e.g., tissue) that the device 10 may come into contact with.

A hinging unit 11 can include at least one first arm 22 extending from a first member 12 and at least one first arm 22' extending from a second member 12', where each first arm 22 of the first member 12 is connected to a respective first arm 22' of a second member 12' at a junction 16 to define a hinging unit 11, which may be a pivot point or region at which the first arm 22 of the first member 12 may flex or bend related to the first arm 22' of the second member 12' about the pivot point or region. In some embodiments, the first arms 22, 22' can be segments of a unitary structure and junction(s) 16 can be an intermediate section or portion of the elongated member that flexes or bends so that the distal ends are rotatable about the junction(s) 16. The junction(s) 16 can be a pivot mechanism, a living hinge, a resilient section of arm 22 and/or arm 22', and/or a resilient section of an interface between arm 22 and arm 22'. The junction(s) 16 can be configured to provide a biasing force to generate a tendency of the device 10 to maintain an open state or a propped state, but allows for displacement and/or deflection of at least one first member 12 relative to at least one second member 12'. In some embodiments, the junction(s) 16 are configured to allow for displacement and/or deflection of at least one arm 22 relative to at least one arm 22', which may in turn allow displacement and/or deflection of at least one first member 12 relative to at least one second member 12'.

Displacement and/or deflection of the members 12, 12' and/or arms 22, 22' can cause a first member 12 to move toward a second member 12' to form a closed state. In some embodiments, a user, such as a surgeon, can use parts of her hand to provide a force for causing such displacement. A closed state can be generated by moving a first member 12 towards a second member 12', creating a low profile by fully collapsing, or partially collapsing, the device 10. This may include abutting a first member 12 against a second member 12'. For example, a closed state may be when the members 12, 12' and/or arms 22, 22' lie in a same geometric plane and or abut each other. However the members 12, 12' and/or arms 22, 22' need not abut each other to form the closed state. The closed state can be formed by generating a low profile by causing the members 12, 12' and/or arms 22, 22' to move towards each so that a distance between the first member 12 and second member 12' or a distance between a first arm 22 and second arm 22' is less than a distance between the first member 12 and second member 12' or a distance between a first arm 22 and second arm 22'when the device 10 is in an open state. In some embodiments, a closed state may occur when the members 12, 12' and/or arms 22, 22' are deflected/displaced toward each other so as to permit the device 10 to be inserted into an incision to generate a biasing force acting upon them to restore them to a non-deflected/non-displaced position. The non-deflected/non-displaced position can be referred to as the open state. The open state can be a relative position of the members 12, 12' and/or arms 22, 22' within a range from an angle greater than 0° degrees to approximately 180° degrees (e.g., the cross-beams 26, 26' of the first and second members 12, 12' are positioned away from each other and are not in contact with each other). The first and second members 12, 12' may rotate about junction(s) 16 as the device 10 moves from its closed state to its open state. A propped state can occur when the device 10 is used to cause the skin and/or tissue to be splayed open by maintaining the members 12, 12' and/or arms 22, 22' at an angle of separation despite the weight if the skin and/or tissue or other force acting on the device 10 that would otherwise cause a transition to a closed state but for the biasing force. Thus, the propped state may occur when the members 12, 12' and/or arms 22, 22' have a relative position that is between the closed state and the open state as the device 10 is adjusted from the closed state to the open state. The resilient biasing of the device 10 to the open state can help provide the propping of the skin. The propped state, or propping of the tissues away from each other can help keep an incision open, keep a dissection path open via tenting, and apply retraction at an incision site.

For example, placement of the device 10 against skin and/or tissue while in a closed state, and allowing the arms 22, 22' to move toward the open state to form a propped state can assist in splaying the tissue open or apart. Further allowing the members 12, 12' and/or arms 22, 22' to maintain their position after advancing towards the open state via the biasing force can define the propped state, which can assist in propping the skin and/or tissue in a salutary position conducive for conducting surgical procedures within the area of operation.

At least a portion of the device 10 may be fabricated from a lightweight, rigid, material, exhibiting little to no thermal conductivity, little to no electrical conductivity, and/or little to on magnetism. Any portion of the device 10 can be semi-rigid or flexible. The material of construction may include, but is not limited to, polymeric material, plastic, rubber, ceramic, surgical steel, nylon, polycarbonate, composite material, metal, etc. Manufacturing methods can include, but are not limited to, additive manufacturing, 3D printing, molding, injection molding, casting, drawing, etc. The device 10 may be fabricated in various sizes so as to accommodate various types of surgeries. The device 10 may be small enough to manipulate with a single hand or large enough to require use of two hands. For example, some embodiments may require use of two hands to cause the device 10 to move towards the closed state, whereas other embodiments may require the use of only one hand. In other embodiments, a tool may be used to provide a force for moving those members toward each other to a closed state for use in a surgical procedure (e.g., inserting into a formed incision). Additionally, at least one surface of the device 10 can be hemostatic, anti-thrombogenic (e.g., coating or incorporation of hemostatic material into the material of the device 10, etc.), hydrophilic so as to better adhere to tissue, sticky or include a non-slip coating or outer surface, etc. At least some portions of the device 10 can be radiopaque so as to be identifiable or observable via X-ray detection methods. Any portion of the device 10 can be opaque, transparent, and/or translucent to visible light. Further, any portion of the device 10 can be configured to provide internal reflection, be configured to be self-luminescent, and/or be non-reflective. In some embodiments, the device 10 can be fabricated with one type of material and coated with another type.

In some embodiments, the device may be shaped to facilitate use of a specific anatomic location. For example, the shape of the device 10 may be configured to specifically sit in a stable fashion on a patient's neck during thyroid surgery. As another example, the device 10 can be shaped in planes that are independent of a plane of primary retraction and independent of a distracting mechanism (e.g., spring mechanism, mechanism used to bias the device to the open position of the device for propping up tissue to draw away or divert tissue, etc.). Any of the contours and/or surfaces of any portion of an embodiment of the device 10 that is intended to contact tissue can be configured to be atraumatic or be as atraumatic as possible given certain design and fabrication constraints for the device to meet a set of design criteria. For example, a portion of the device 10 that is intended to make contact with a tissue can have a specifically configured ergonomic shape (e.g. composition, contour, shape, and/or surface shaping) so as to maximize exposure and visualization for a surgeon working within an incision site during a procedure while minimizing trauma to the region of the body that the portion of the device 10 contacts. In some embodiments, the device may be configured to include one or more curved lips. Each lip can be configured to conform to an incision or tissue. Examples of such lips may be seen from FIGS. 39-47. For instance, clamp members 70 and 70' can be configured to provide such curved lips. Additionally (or as an alternative) cross members, plates, or other elements of a member may have such contours on an external surface of the device or an internal surface of the device configured to contact tissue.

A method of retracting a first tissue from a second tissue can include creating an incision to expose a first/second tissue interface, creating a tissue pocket with the first/second tissue interface and the incision defining the tissue pocket, wherein at least a portion of the first/second tissue interface is a leading dissection edge. The device 10 can then be grasped or otherwise manipulated for collapsing into a closed state. While the various figures may show a specific embodiment, it is understood that the features disclosed by any one figure can be applicable to any other embodiment.

Figure 2:
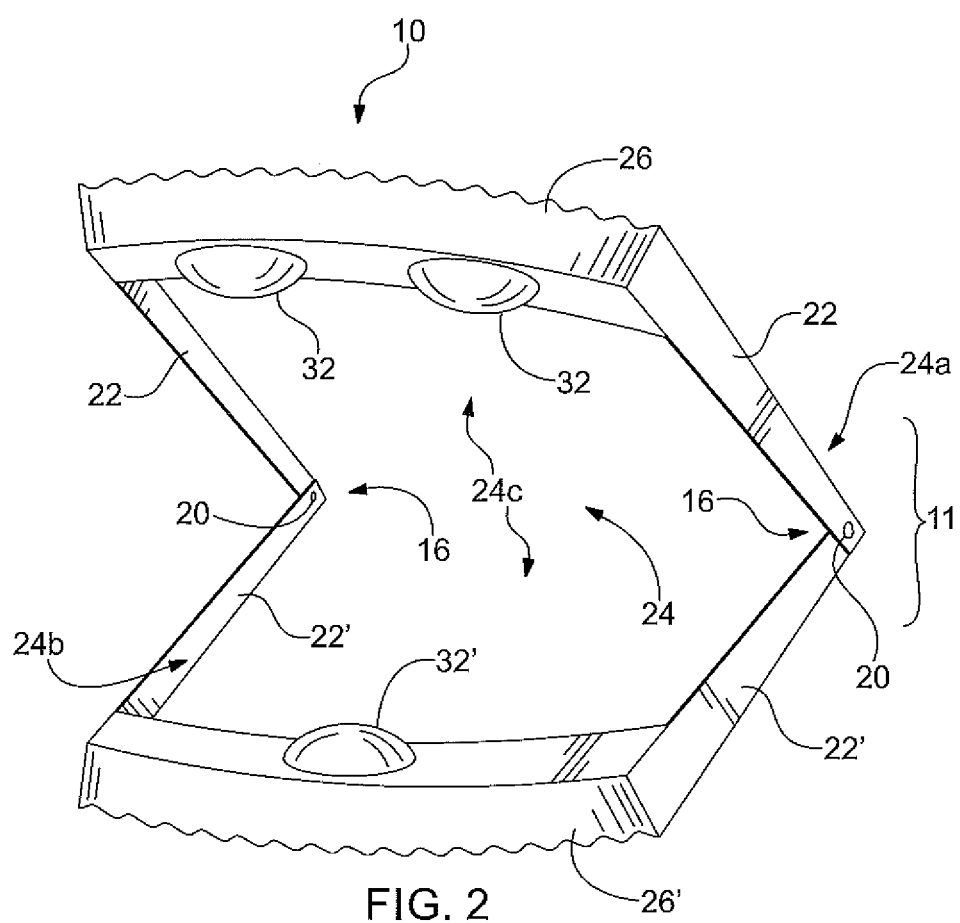
FIG. 2 is a perspective view of an exemplary embodiment of the device with the first U-shaped member pivotally connected to the second U-shaped member.

Referring to FIGS. 1-2, in a non-limiting exemplary embodiment, the device 10 can include a first member 12 having first and second arms 22 extending from a first cross-beam 26. A second member 12' can be provided having first and second arms 22' extending from a second cross-beam 26'. A distal end of the first arm 22 of the first member 12 can be connected to a first end of the first cross-beam 26 and a proximal end of the first arm 22 of the first member 12 can be connected to a proximal end of the first arm 22' of the second member 12' at a first junction 16. A second end of the first cross-beam 26 may be connected to a distal end of the second arm 22' of the first member 12. A proximal end of the second arm 22 of the first member 12 may be connected to a proximal end of the second arm 22' of the second member 14 at a second junction 16. The distal end of the first arm 22' of the second member 12' can be connected to a first end of the second cross-beam 26' and the proximal end of the first arm 22' of the second member 14 can be connected to the proximal end of the first arm 22 of the first member 12 at the first junction 16. A second end of the second cross-beam 26' can be connected to a distal end of the second arm 22' of the second member 12', and the proximal end of the second arm 22' of the second member 12' can be connected to the proximal end of the second arm 22 of the first member 12' at the second junction 16.

The first and second members 12, 12' may be statically, resiliently, or pivotally connected at the first and second junctions 16. A static connection may be an affixation in which the first member and second member are joined together by a junction, where the junction may exhibit little to no resiliency. Such a static connection may be made by the members being portions of a device that is molded or 3D printed as a single unitary structure, for example. The static connection can facilitate a resilient ending of the members 12, 12' about a junction 16. A resilient connection may be an affixation in which the junction 16 exhibits resiliency. The resilient connection can facilitate a resilient bending of the junctions 16 to allow for relative movement of the members 12, 12'. A pivotal connection may be an affixation in which the junction 16 includes a rotational engagement so as to allow rotational movement of one member 12 relative to another member 12'. In some embodiments, a combination of connections may be used to facilitate pivoting, flexing, or bending about one or more junctions 16 based on the structure and arrangement of the junctions such that the members are moveable toward each other and away from each other via a one or more hinges defined by such junctions 16. In some embodiments, the junction(s) 16 may be intermediate or central segments of an elongated member 12, 12' and the first and second arms 22, 22' joined at junction 16 can be distal segments of the member extending away from the junction, where the arms 22, 22' may extend away from each other.

The first and second junctions 16 can be configured to provide a biasing force to force the first cross-beam 26 of the first member 12 to move away from the second cross-beam 26' of the second member 12'. The first member 12 can be movable so the first cross-beam 26 abuts the second cross-beam 26' to form a closed state of the device 10 and the first cross-beam 26 can be movable away from the second cross-beam 26' to form an open state or propped state of the device 10.

The device 10 can be in a closed state in other positions in which it is moveable from that closed state to an open state. For instance, instead of there being an abutment between the first and second members 12 and 12', there may be a gap or space that defines a small mouth 24b between the distal sides or ends of the first and second members 12 and 12' when the device is in the closed state and the mouth 24b may be defined to be a larger opening when the device 10 is in its open state. The device 10 can also be configured so that in its closed state the first member 12 (e.g. a distal end of side of the first member) is a first distance away from the second member 12' (e.g. a distal end or side of the second member) and in its open state the first member 12 (e.g. a distal end or side of the first member) is a second distance away from the second member 12' (e.g. a distal end or side of the second member) where the second distance is greater than the first distance. The distal ends of the arms 22 affixed at the first member can be spaced apart a first distance from distal ends of arms 22' affixed at the second member 12' when the device 10 is in its closed state and the distal ends of arms 22 of the first member can be spaced apart a second distance from the distal ends of the arms 22' of the second member 12' when the device is in its open state. The closed state can also (or alternatively) be defined such that a mouth is defined when the device is in the open state and the mouth has a smaller size (e.g. smaller diameter, smaller perimeter, smaller area, and/or smaller volume etc.) when the mouth 24b is defined or is non-existent (e.g. with the first and second members 12, 12' abutting or recessed within each other) when the device is compressed into its closed state.

Figure 54:
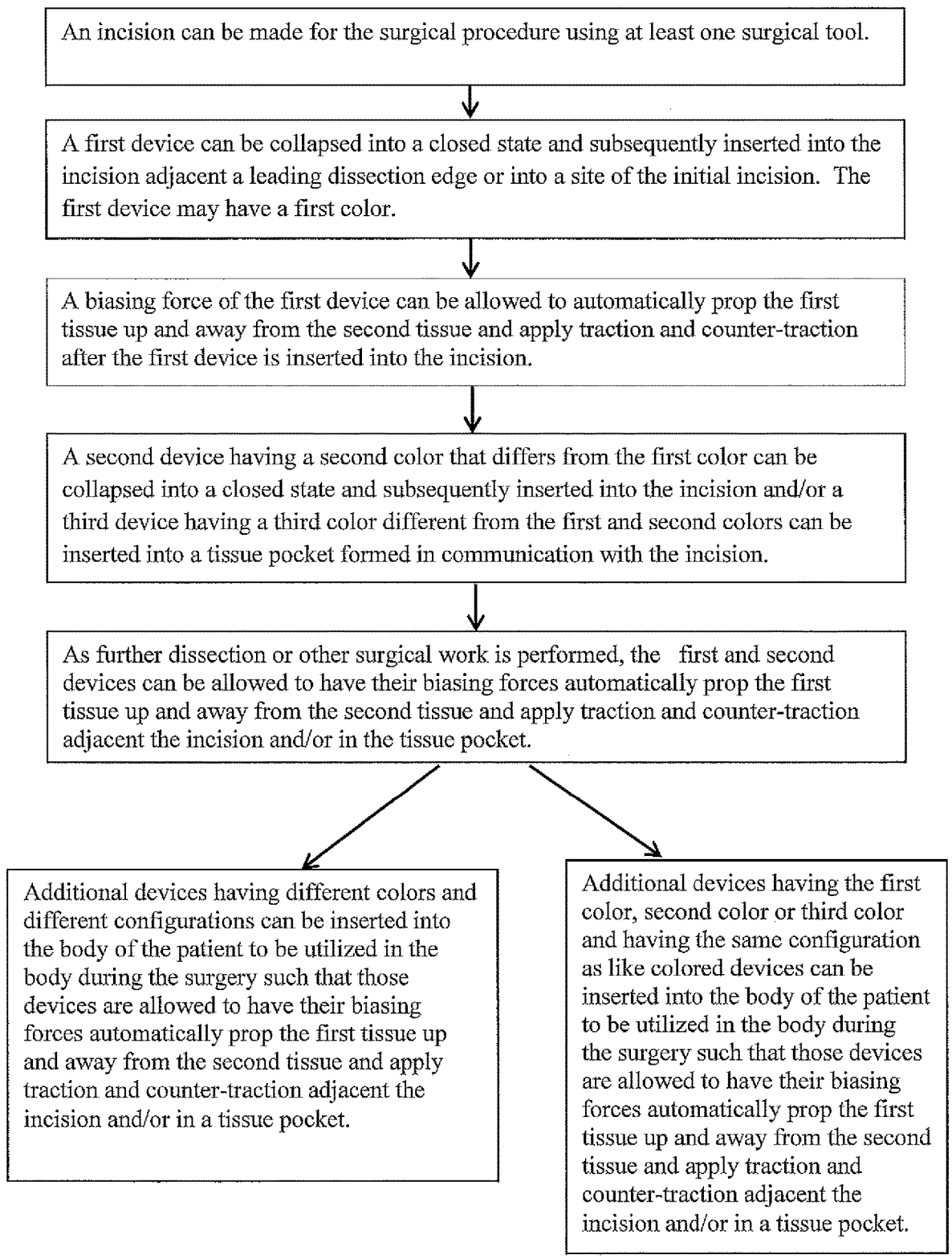
FIG. 54 is a flow chart illustrating an exemplary method of using at least one embodiment of the device in a surgical procedure.

As may be appreciated from FIGS. 52-54, the device 10 can be transitioned to a closed state (e.g. by use of fingers in one hand or use of a device to compress the first and second members 12, 12' toward each other sufficiently to overcome the biasing force acting to bias the members away from each other to bias the device to its open position), and can then be inserted through the incision and into the incision and/or a tissue pocket defined within or in communication with the incision. For instance, a first device 10 can be positioned adjacent the leading dissection edge and the biasing force of the first device can be allowed to automatically move the first device toward the open position to prop the first tissue up and away from the second tissue and apply traction and counter-traction at the incision adjacent the leading dissection edge. Further dissection of the first tissue from the second tissue at the leading dissection edge can be performed while the first device 10 is in the incision to provide continuous traction and counter-traction at the leading dissection edge as the leading dissection edge is propagated along a dissection path. As the further dissection occurs after the first device 10 is inserted into the incision, the first device 10 may move to the fully open state via the biasing force such that motion of the device during the further dissection occurs automatically without any actuation or manipulation from a surgeon or surgical assistant.

A second device 10 can be compressed to its closed position and subsequently positioned in the incision as the further dissection occurs at a spaced apart location from the first device 10. The second device 10 may function similarly to the first device after being so positioned in the incision. For instance, the second device 10 can be positioned within the incision after further dissection away from the leading edge has occurred and the biasing force of the second device 10 can be allowed to automatically move the second device 10 toward the open position to prop the first tissue up and away from the second tissue and apply traction and counter-traction at the incision as further dissection continues along an incision path away from the first device and/or away from the second device. Further dissection of the first tissue from the second tissue can be performed while the second device 10 is in the incision to provide continuous traction and counter-traction as the incision is further propagated along a dissection path. As the further dissection occurs after the second device 10 has been inserted into the incision, the second device 10 may move to the fully open state via the biasing force such that motion of the device 10 during the further dissection occurs automatically without any actuation or manipulation from a surgeon or surgical assistant.

Additionally, or as an alternative, a third device can be compressed to its closed position and subsequently placed inside a tissue pocket adjacent to the incision or in communication with the incision during the surgical procedure. The third device 10 may function similarly to the first device and/or second after being so positioned in the tissue pocket. For instance, the third device 10 can be positioned within the tissue pocket and the biasing force of the third device 10 can subsequently be allowed to automatically move the third device 10 toward the open position to prop the first tissue up and away from the second tissue and apply traction and counter-traction in the tissue pocket as further dissection within the tissue pocket or as further dissection of the incision along a dissection path occurs. Further dissection of the first tissue from the second tissue can be performed while the third device 10 is in the tissue pocket to provide continuous traction and counter-traction as the incision is further propagated along a dissection path and/or as further surgical work is done within the tissue pocket. As the further dissection and/or surgical work within the tissue pocket occurs after the third device 10 has been inserted into the tissue pocket, the third device 10 may move to the fully open state via the biasing force such that motion of the device 10 during the further dissection and/or surgical work occurs automatically without any actuation or manipulation from a surgeon or surgical assistant.

In some embodiments, the device 10 may include two members 12, 12', each having first and second arms 22, 22' that are substantially parallel to each other extending from a cross-beam 26, 26' of a member 12, 12'. The arms 22, 22' may be members (e.g., rails, beams, etc.) that are linearly extended, extended at an angle, curvilinear, or have other shapes. The device 10 may be structured so that the first and second arms 22 of a first member 12 are connected to the first and second arms 22' of a second member 12', and the points at which the arms 22, 22' connect form junctions 16. In some embodiments, the device 10 may be formed or molded as a unitary structure and the arms 22, 22' may be segments extending between the first and second members 12, 12'.

The device 10 may be structured to form a general wedge-shaped device 10 configured to retract skin from underlying tissue along a dissection plane and/or at an incision edge by being dynamically movable into a wedge-like configuration during a surgical procedure. The device 10 can be configured to automatically splay open during a procedure after insertion into the incision to provide continuous traction and counter traction without a user having to rotate the device after insertion.

Spanning between the first and second arms 22 of the first member 12 can be at least one cross-beam 26, which may be disposed between the distal ends of the first and second arms 22. The cross-beam 26 can be a portion of the first member 12. Spanning between the first and second arms 22' of the second member 12' can be at least one cross-beam 26', which may be disposed between the distal ends of the first and second arms 22'. The cross-beam 26' can be a portion of the second member 12'. Any portion of the device 10 (e.g., cross-beam, arm, etc.), or the device 10 as a whole, may exhibit a shape that is more conforming to the body part on which surgery is being performed. For instance, each cross-beam 26 26' may have an arcuate shape, C-shape, spade-shape, V-shape, etc. The various shapes can be used to better coincide with the anatomical shape associated with a body part (e.g., breast) and/or assist with spearheading insertion of the device 10 into a subcutaneous pocket. In some embodiments, the cross-beam 26 of the first member 12 may differ in shape than the cross-beam 26' of the second member 12'. In other embodiments, the shapes of the cross-beams 26, 26' may be the same, or may be substantially the same to each other.

The device 10 may be formed or structured as a unitary piece, wherein the first member 12 may be statically connected to the second member 12' at the junctions 16. In this embodiment, the first member 12 can be displaceable about the junctions 16 without pivoting about a junction axle due to the resilient nature of the arms 22, 22' and/or portion of the arms 22, 22' at an/or near the junction(s) 16. In other words, the configuration and resilient nature of the arms 22, 22' form a resilient hinging unit 11. Thus, each member 12, 12' may be deflected in the direction of the arrows 18 to exhibit a biasing force in the opposing direction to open jaws defined by the members 12, 12'.

Alternatively, each junction 16 may include or have a pivot mechanism 20 enabling rotatable motion of the first member 12 relative to the second member 12', as shown in FIG. 2. The pivot mechanism 20 may include a pin and hub assembly, hinge-pin and hinge-plate assembly, or similar rotating means. Thus, the hinging unit 11 may be formed by the pivot mechanisms 20 connecting arms 22, 22' together. At least one spring mechanism may be positioned at each junction 16 for biasing the U-shaped members 12, 12' away from each other. The at least one spring mechanism may be coupled to the members 12, 12' at the junctions 16 for providing the bias force for biasing the device 10 to its open state or propped state. This may be done so that the device 10 is biased to move distal ends of the members 12, 12' away from each other to open the jaws of the device 10 and form a generally wedge-shape. The spring mechanism may include, but is not limited to, a coil spring, leaf spring, torsion spring, elastic spring element, or other spring mechanism. Rotating the members 12, 12' together may compress the spring mechanism, resulting in a biasing force generated by the spring to bias the members' distal ends further away from each other. In some embodiments, each pivot mechanism 20 can include an integral spring system, which could reduce costs of manufacturing and further enable tailoring an amount of force required to compress (transition to the closed state) the device 10.

The pivot mechanism 20 or other portion of the device 10 may also be provided with a mechanical stop or strut (not shown) to prevent rotation of the members 12, 12' after passing a certain point of relative rotation. Thus, the mechanical stop may be used to limit the range of motion of the two members 12, 12' relative to each other. The mechanical stop may be used with or without a spring mechanism. Embodiments of the device 10 without the spring mechanism may use the mechanical stop to prevent rotation passed a certain point, wherein further attempted-rotation may cause the members 12, 12' to resiliently displace and generate the biasing force described above. In further embodiments, the pivot mechanism 20 may be covered with a shroud (not shown) to prevent catching or entrainment of skin/tissue. In some embodiments, the shroud may be a cover or sheath that extends over the proximal ends of the members 12, 12' at the junctions 16 and/or the pivot mechanism 20.

Each cross-beam 26, 26' may include an outer-facing surface 28, 28' and an inner-facing surface 30, 30'. At least one outer-facing surface 28, 28' may include a gripping structure 29, 29'. The gripping structure 29, 29' can be a textured surface, an undulated surface, toothed surface, grooved surface, treated surface, a coating, etc. This may be done to reduce slippage between the device 10 and the skin/tissue. In addition, or in the alternative, the material of the cross-beam 26, 26', at least at the outer-facing surface 28, 28', may comprise a material that increases the coefficient of friction between the device 10 and the skin or tissue. In some embodiments, a coating may be positioned over at least a portion outer-facing surface 28, 28' to further increase the coefficient of friction between the outer-facing surface 28, 28' and the skin/tissue. In addition to or in the alternative to the gripping structure 29, 29', an adhesive can be applied to any portion of the device 10 to facilitate temporary adherence of the device 10 to the skin or other tissue. This adhesive may be applied by a surgeon during a procedure or the adhesive can be defined or included on or in the device 10. If the adhesive is defined on or in the device 10, the adhesive may be covered by a removable cover prior to use. Just before use (e.g., after insertion into an incision or before insertion into the incision), the cover can be removed, exposing the adhesive and allowing a surgeon to attach the portion of the device 10 with the exposed adhesive to tissue within an incision or adjacent the incision.

At least one inner-facing surface 30, 30' and/or outer-facing surface 28, 28' of the first member 12 and/or second member 12' may include a finger retainer 32, 32' (e.g., knob, protrusion, recess, and/or indentation, etc.) to assist with gripping and manipulation of the device 10. In some embodiments, the finger retainers 32, 32' may be sized to accommodate different fingers (e.g., fore-finger, thumb, pinky, middle finger, pointer finger, etc.)

For instance, a finger retainer 32, 32' may be located on in inner-facing surface 30, 30' so the device 10 may be transitioned from an open state and/or propped state to the closed state. The device 10 may be positioned and repositioned with the simple act of moving the thumb and at least one other finger of one hand towards each other or away from each other while the fingers are in the finger retainers 32, 32' to facilitate manipulation of the device 10. With a finger retainer 32, 32' located on an outer-facing surface 28, 28', the device may be transitioned towards a closed state, and may further be positioned and repositioned with the simple act of compressing the device 10 with the thumb and at least one other finger while the fingers are in the finger retainers 32, 32' to assist with retaining the thumb and fingers in place during manipulation of the device 10. At least one inner-facing surface 30, 30' and/or outer surface 28, 28' may also include a textured surface and/or coating for increasing the coefficient of friction between the inner-facing surface(s) 30 and fingers of a user. The finger retainers 32, 32' can be formed to be accommodating to users who intend to use their left hand or their right hand (i.e., a device 10 can be designed to be right-handed, left-handed, or ambidextrous). For example, the finger retainer 32, 32' for the thumb or finger may be positioned closer to one side of the device 10 for right-handed users or closer to an opposite side for left-handed users to facilitate use or manipulation via only one hand.

FIG. 2 shows multiple finger retainers 32 disposed at a lateral end of the inner-facing surface 30 of the first member 12 cross-beam 26, and a single finger retainer 32' disposed at a central location of the inner-facing surface 30' of the second member 12' cross-beam 26' between the lateral end positioned finger retainers 32'. This configuration can further enhance the ability to handle and manipulate the device 10 by splaying the thumb, forefinger, and middle finger of a single hand, wherein the finger retainers 32, 32' can be ergonomically positioned to make contact with the thumb and fingers. It should be appreciated that any combination of two or more fingers of a user's hand may be utilized for manipulating the device 10 via the finger retainers 32, 32'. For instance, a user may employ her forefinger and middle finger to handle the device 10. It is noted that FIG. 2 only shows one of many configurations for placement and use of the finger retainers 32, 32'.

The device 10 may be further structured such that an opening 24 is defined by the space between the arms 22, 22' and the junctions 16 within the device 10. The opening 24 can include an inlet 24a and a mouth 24b that is definable between the cross-beams 26, 26'. The opening 24 can extend between the inlet 24a and the mouth 24b with an intermediate region 24c between the cross-beams 26, 26'

Figure 3:
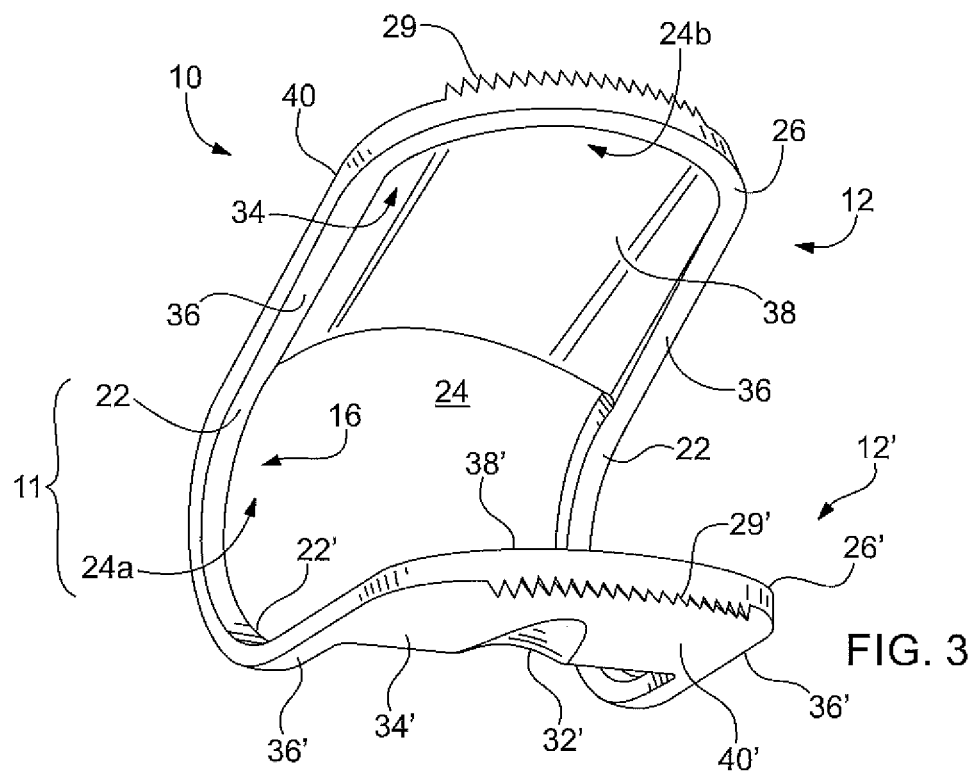
FIGS. 3-4 show perspective views of an exemplary embodiment of the device with a first member connected to the second member via a hinging unit, where each first member and second member includes a plate.
Figure 4:
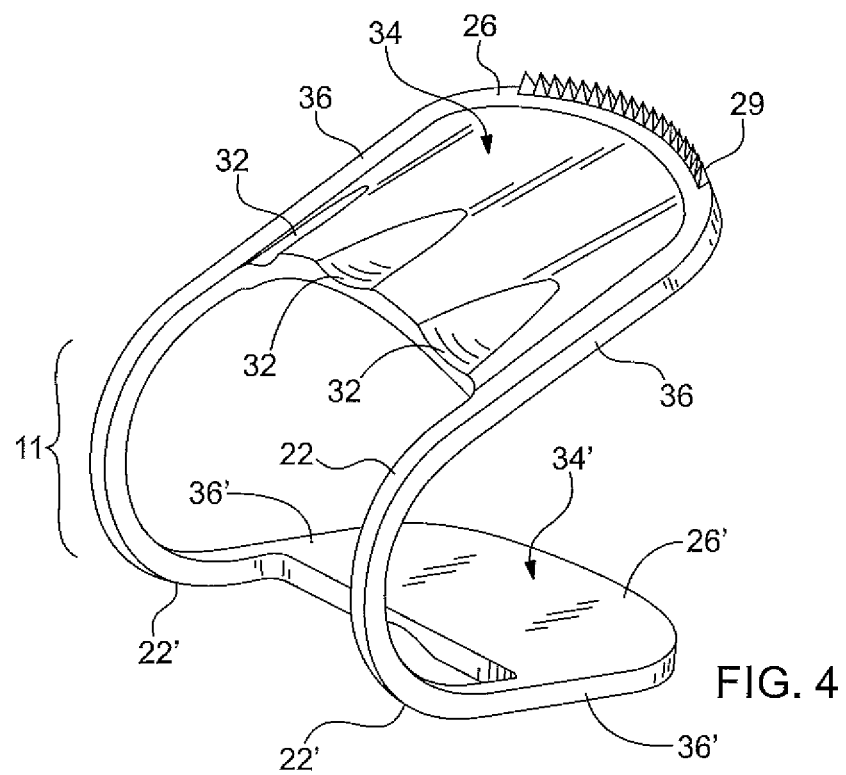

Referring to FIGS. 3-4, in some embodiments, at least one member 12, 12' may have a plate 34, 34' or other element positioned between the arms 22, 22' and the cross-beams 26, 26'. For example, the first member 12 may include a first plate 34. Similarly, the second member 12' may include a second plate 34'. The plate(s) 34, 34' may be molded from the same material as the members 12, 12' or may be segments of a unitary structure. Where both members 12, 12' include a plate 34, the device 10 may be structured so that opening 24 is between the two plates 34, 34' and extends from inlet 24a to mouth 24b. In some embodiments, any surface of the plate(s) 34, 34' can include a finger retainer 32, 32' or other feature.

In some embodiments, the first arm 22 of the first member 12 may have its distal end connected to a first end of the cross-beam 26 and have its proximal end (which is opposite its distal end) connected to the proximal end of the first arm 22'of the second member 12' at a first junction 16. The second end of the cross-beam 26 of the first member 12 that is opposite its first end may be connected to the distal end of the second arm 22 of the first member 12. The proximal end of the second arm 22 of the first member 12 can be connected to the proximal end of the second arm 22'of the second member 12' at a second junction 16. The first and second junctions 16 may be defined as spaced apart junctions 16 or may be junctions 16 defined within an elongated member (e.g., a rod, a bar, a beam, etc.) that extends between the junction 16 formed at the proximal ends of the first arms 22, 22' of the first and second members 12, 12' and the junction 16 formed at the proximal ends of the second arms 22, 22' of the first and second members 12, 12'. In other embodiments, it is contemplated that the configuration of the cross-beams 26, 26' and arms 22, 22' of the members 12, 12' may be arranged to define a wedge-shape, C-shape, V-shape, or other shape. The first and second members 12, 12' may be rotatable about junctions 16 such that the cross-beams 26, 26' of the first and second members 12, 12' may be moved to and from a closed position and an opened state or a propped state for propping of the skin or other tissue underlying the skin. The junctions 16 can be configured so that the members 12, 12' are biased to move away from each other toward the opened state to effect such propping.

The first and second members 12, 12' may each be structured to define an opening 24 or other type of aperture between the arms 22, 22' and cross-beam 26, 26'. The opening 24 may also be defined between junctions 16 so that an inlet 24a is defined between the junctions 16. The inlet 24a of opening 24 can be defined between the junctions 16 at the proximate end of the device 10 to help facilitate further incision by use of a cutting mechanism positioned inside the device 10 via the inlet 24a when the device 10 is in an opened state or propped state. In other embodiments, it is contemplated that no such inlet 24a may be defined between junctions 16. Instead, opening 24 may be defined by a portion of the first or second member 12, 12' when the first member 12 is moved away from the second member 12' to expose a mouth 24b at a distal end of the device 10 between the first and second members 12, 12' and/or cross-beams 26, 26' and/or plates 34, 34'.

In yet other embodiments, it is contemplated that a first plate 34 may be attached between the first and second arms 22, 22' and the cross beams 26, 26' to define a contacting surface for only one of the first and second members 12, 12'. For instance, the first member 12 of the device 10 may have such a plate 34, or the second member 12' of the device 10 may have such a plate 34. As will be described in detail, a surface of any plate 34, 34' may have a profile (e.g., at least one tread, groove, bump, projection, furrow, etc.) defined therein to facilitate better frictional contact between that plate and tissue or skin to which that plate 34, 34' may contact when the device 10 is positioned in a body of a patient during a surgical procedure. The plates 34, 34' may be configured to provide a larger surface area at which skin or tissue may be contacted when the device 10 is in use to provide further support for providing traction and counter traction during a surgical procedure.

In some embodiments, at least one cross-beam 26, 26' and/or plate 34, 34' can include a gripping structure 29, 29', as described above. In at least one embodiment, the teeth of the gripping structure 29, 29' can flex outward when the device 10 is transitioned to a closed state and flex inward when the device 10 is transitioned to the open state and/or propped state. For example, with a device 10 where the cross-beams 26, 26' are the distal end of the device 10, the teeth of the gripping structure 29, 29' can deflect towards the distal end when the device 10 is transitioned to the closed state and retract back to their non-deflected position when the device 10 is transitioned to the open state or propped state. This can be achieved by fabricating portions of the cross-beams 26, 26' and/or plates 34, 34' with a multi-layered material, where each layer of material exhibits a different resiliency. Thus, when the device 10 is transitioned into the closed state, the differential in resiliency may cause the teeth to flex in a desired direction and flex back when the device 10 is transitioned to the open state or propped state. This can allow the teeth to "bite" into the tissue. Further, the teeth may exist in various shapes and sizes to provide a desired level of gripping. In some embodiments, the teeth can be adjustable and/or replaceable. For example, a row of teeth can snap on to and off from the device 10, thereby allowing a user to vary the level of gripping. As another example, the teeth may be releasably interlocked with a member 12, 12' or cross-beam 26, 26' for reusable attachment As shown in FIGS. 3-4, some embodiments may include a device 10 having a first member 12 connected to a second member 12' via a hinging unit 11. The first member 12 can include a first side section 36a and a second side section 36b conjoined by a cross beam 26 to exhibit a U-shape. The second member 12' can include a first side 36a' section and a second side section 36b' conjoined by a cross beam 26' to exhibit a U-shape. The first member 12 can further include a plate 34 spanning a space between its first side section 36a, its second side section 36b, and its cross beam 26. The second member 12' can further include a plate 34' spanning a space between its first side section 36a', its second side section 36b', and its cross beam 26'. At least one of the first member plate 34 and the second member plate 34' can have a surface that is flat, curvilinear, arcuate, concave, convex, etc. Further, each of the first member plate 34 and the second member plate 34' can include an inner-facing surface 38, 38' and an outer-facing surface 40, 40'. Any portion of the first member 12 and/or any portion of the second member 12' can include at least one finger retainer 32, 32', as described earlier. A user can use the finger retainers 32, 32' to assist with griping the device 10 when transitioning the device 10 to and from the closed state and open state. For example, at least one finger retainer 32 may be placed on an outer-facing surface 40 of the first member plate 34. Similarly, at least one finger retainer 32' may be placed on an outer-facing surface 40' of the second member plate 34'. A user may then grasp the device 10 with different fingers of the same hand by inserting them onto and/or into the finger retainers 32 to transition the device 10 from the open state to the closed state and to further move and manipulate the device 10.

In some embodiments, at least one finger retainer 32, 32' can be a recess formed into a plate 34, 34', where the recess may further have a conical profile to better conform to a particular finger (e.g., forefinger, thumb, pinky, etc.). As shown in FIGS. 3-4, the device 10 can include a single finger retainer 32' formed into an outer-facing surface 40' of the second member plate 34' and three finger retainers 32 formed into an outer-facing surface 40 of the first member plate 34. It is contemplated that a user may place a thumb on the finger retainer 32' of the second member plate 34' and three fingers on the finger retainers 32 of the first member plate 34 to assist a user in grasping and manipulating the device 10.

The hinging unit 11 can include first and second arms 22, 22' connecting the first member first side section 36a with the second member first side section 36a' via a first junction 16. The hinging unit 11 can further include first and second arms 22, 22' connecting the first member second side section 36b with the second member second side section 36b' via a second junction 16. The first and second arms 22, 22' can be fabricated from a resilient material, such as rubber, plastic, polymeric, elastic material, steel, metal, etc. so as to generate the biasing force to bias the first and second members 12, 12' to the open state. In some embodiments, the first and second arms 22, 22' can be fabricated from a rigid material defining the junctions 16. The resilient arms 22, 22' and/or resilient junction(s) 16 may enable flexing about an axis of rotation, which can facilitate deflection of the first member 12 relative to the second member 12'. In some embodiments, the hinging unit 11 may have an arcuate shape so that the device 10, from a side view, may exhibit a C-shape when in an open state and a tear-drop shape when transitioned to a closed state. In some embodiments, the device 10 can be structured to have an opening 24 defined by the space between the arms 22, 22' and the junctions 16 having an intermediate region 24c between and in communication with an inlet 24a and mouth 24b. The device 10 can include a gripping structure 29, 29' on a portion of the cross-beam 26, 26' and/or plate 34, 34'. The gripping structure 29, 29' can be structured as a row of teeth disposed along an edge of any cross-beam 26, 26' for example.

As shown in FIGS. 3-4, the first member plate 34 may exhibit a convex shape on its outer-facing surface 40 and a concave shape on its inner-facing surface 38. The second member plate 34' may exhibit a flat shape on its outer-facing surface 40' and a flat shape on its inner-facing surface 38'. The concave/convex shapes of the first member plate 34 may be used to better conform to the skin of the body part while the flat shapes of the second member plate 34' may be used to provide a stable support for the device 10 while it is inserted in a subcutaneous pocket. However, it is contemplated that the second member plate 34' may also exhibit similar concave/convex shapes as that of the first member plate 34 to provide the stable support by conforming to the shape of the underlying tissue. It is further contemplated for any of the first member plate 34 and the second member plate 34' to exhibit other shapes to provide a desired function.

Figure 5:
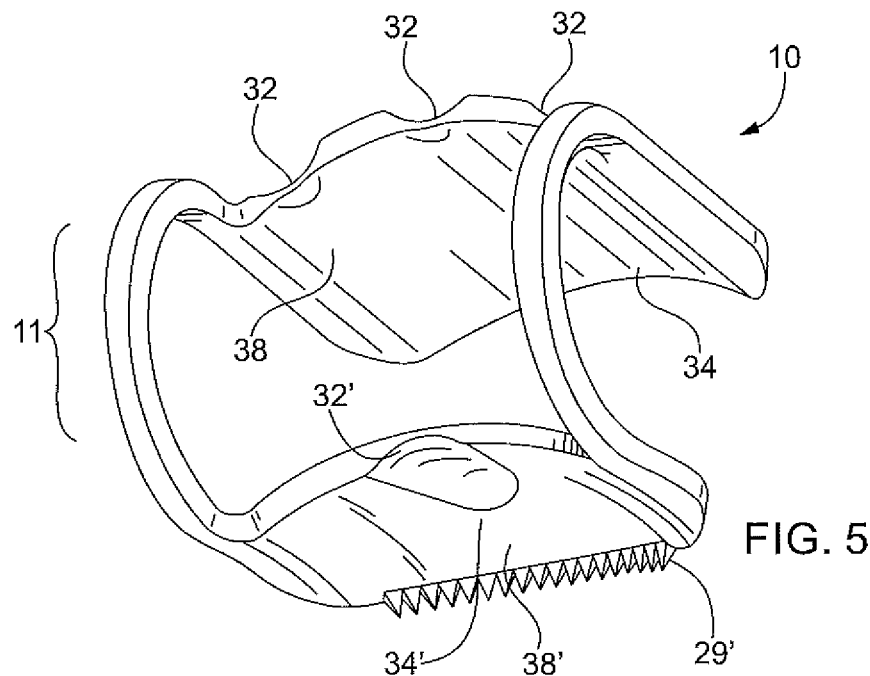
FIGS. 5-6 show perspective views of an exemplary embodiment of the device with the plates exhibiting concave shapes on their inner-facing surfaces and convex shapes on their outer-facing surfaces.
Figure 6:
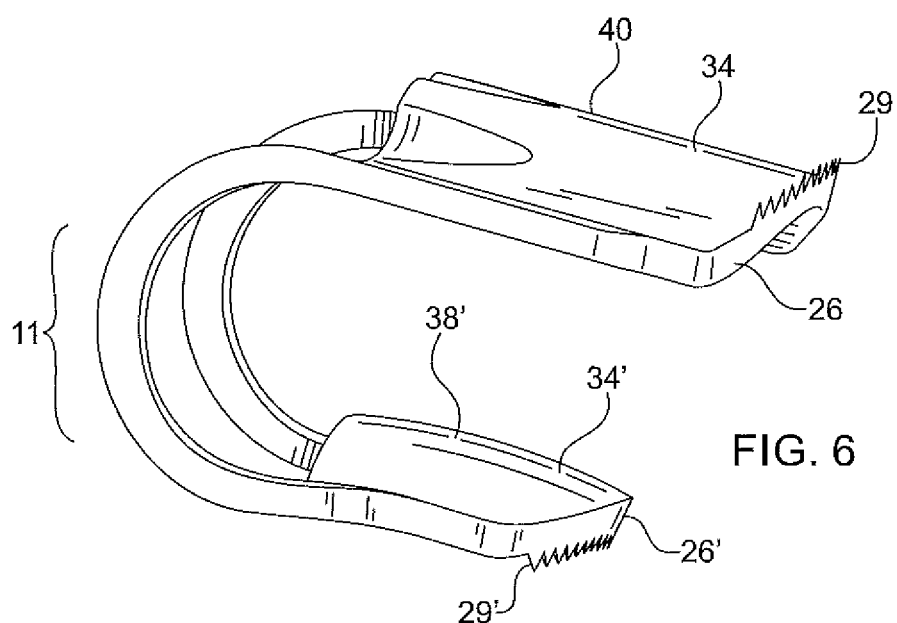

Referring to FIGS. 5-6, the device 10 can include a gripping structure 29, 29' structured as a row of teeth disposed along an edge of any or cross-beam 26, 26'. As shown in FIGS. 5-6, both of the first member plate 34 and the second member plate 34' may exhibit a convex shape on their outer-facing surfaces 40, 40' and a concave shape on their inner-facing surfaces 38, 38'.

Figure 7:
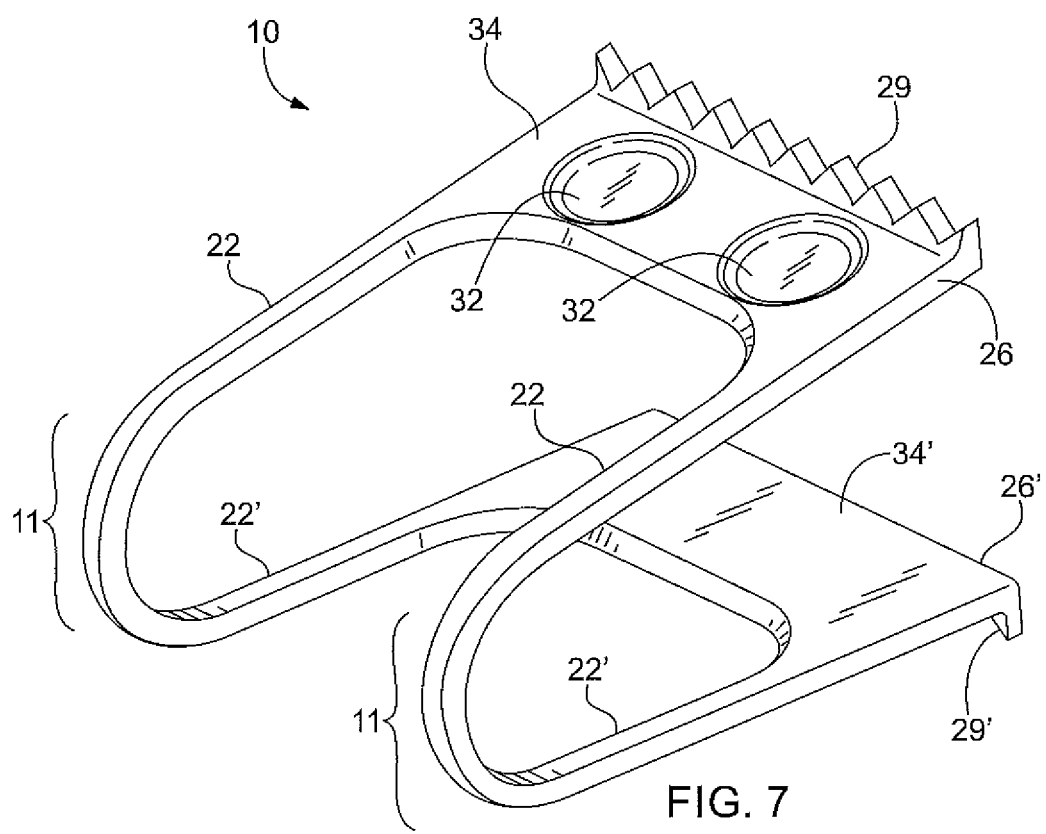
FIG. 7 shows a perspective view of an exemplary embodiment of the device with finger retainers as circular depressions within at least one plate.

Referring to FIG. 7, the device 10 can include a gripping structure 29, 29' structured as a row of teeth disposed along an edge of any cross-beams 26, 26'. Further, any one of the first member plate 34 and the second member plate 34' may exhibit a flat shape on their outer-facing surfaces 40, 40'. Further, any one of the first member plate 34 and the second member plate 34' may exhibit a flat shape on their inner-facing surfaces 38, 38'. At least one of the first member plate 34 and the second member plate 34' can include a finger retainer 32, 32' on its outer-facing surface 40, 40'. Any finger retainer 32, 32' can be a circular depression. For example, the first member plate 34 can include two circular depression finger retainers 32 on its outer-facing surface 40. Further, the second member plate 34' can include at least one circular depression finger retainer 32' on its outer-facing surface 40'.

Figure 8:
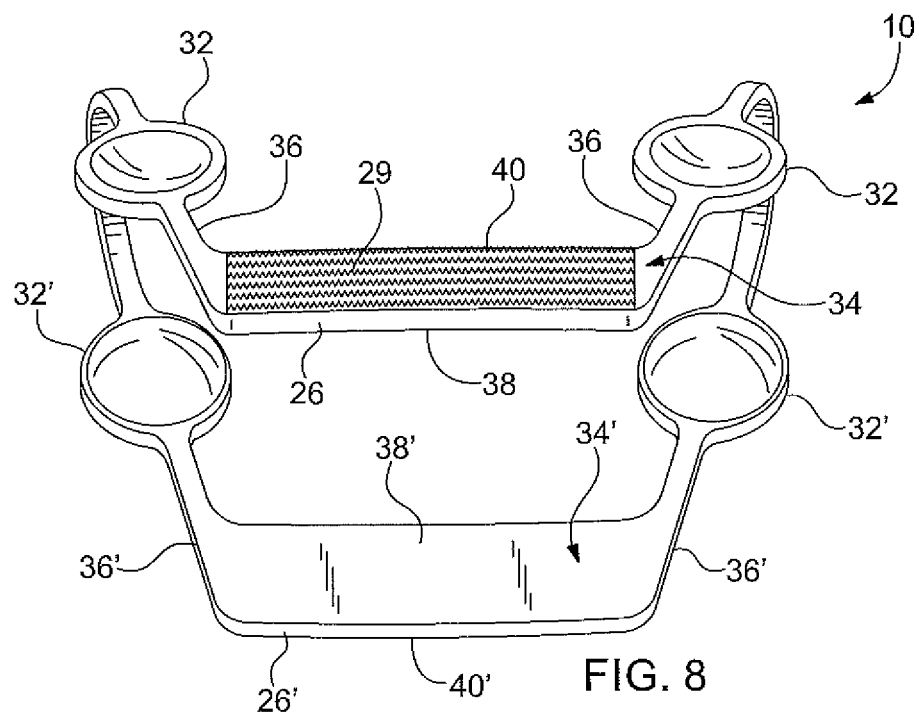
FIGS. 8-9 show perspective views of an exemplary embodiment of the device with a gripping structure in a form of a textured surface or a dimpled surface disposed on at least one of the outer-facing surface of the first member plate and the outer-facing surface of the second member plate.
Figure 9:
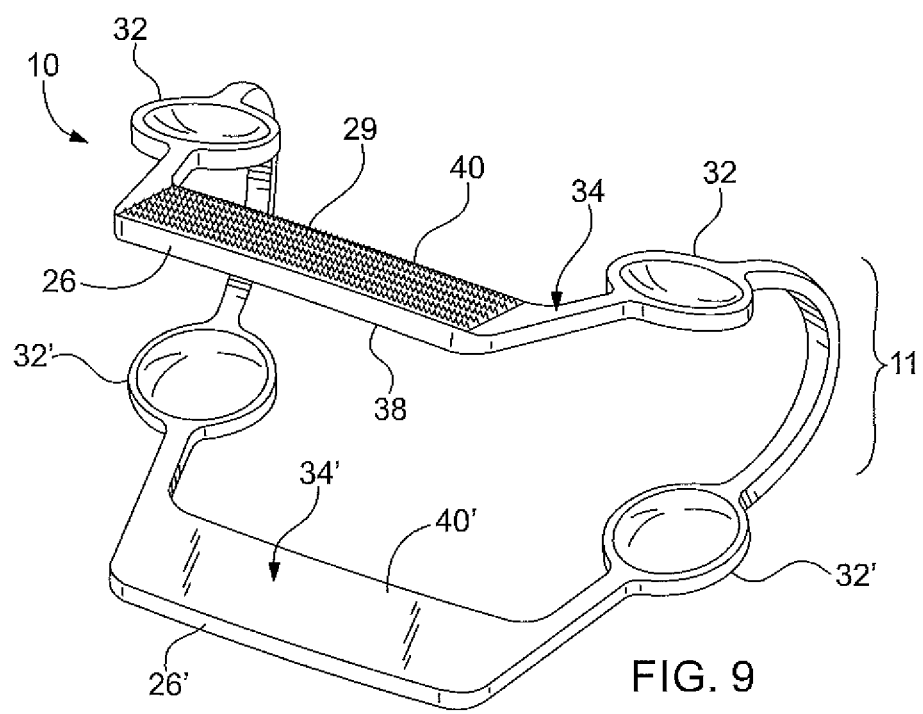

Referring to FIGS. 8-9, the device 10 can include a gripping structure 29, 29' structured as a textured surface or a dimpled surface disposed on at least one of the outer-facing surface 40 of the first member plate 34 and the outer-facing surface 40' of the second member plate 34'. Any or both of the first member plate 34 and the second member plate 34' may exhibit a flat shape on their outer-facing surfaces 40, 40'. Any or both of the first member plate 34 and the second member plate 34' may exhibit a flat shape on their inner-facing surfaces 38, 38'. Further, at least one arm 22, 22' can include a finger retainer 32, 32'. Any one or multiple of finger retainers 32, 32' can be can be a circular disc having a circular depression or another shaped depression or groove.

Figure 10:
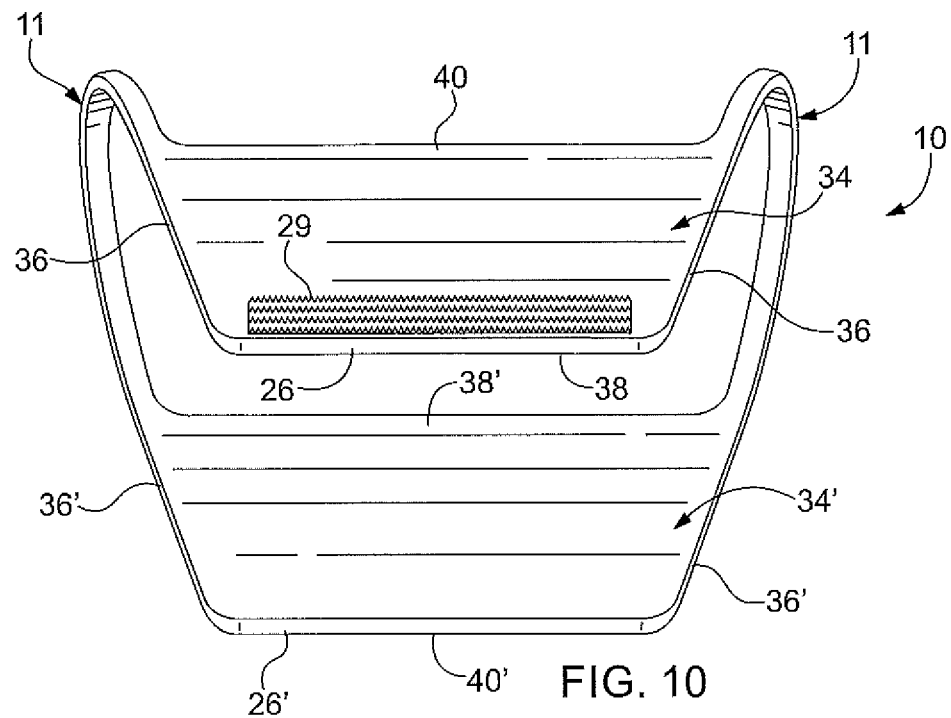
FIGS. 10-11 show perspective views of an exemplary embodiment of the device with the gripping structure as a strip of the textured surface or dimpled surface adjacent a cross-beam edge.
Figure 11:
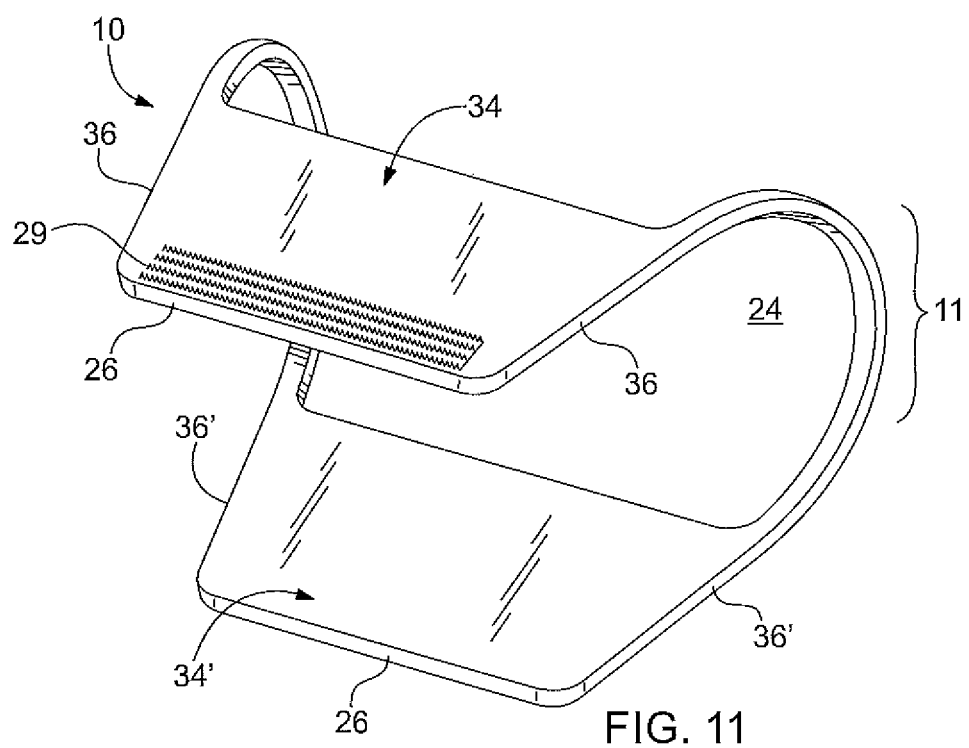

Referring to FIGS. 10-11, the device 10 can include a gripping structure 29, 29' structured as a textured surface or a dimpled surface disposed on at least one of the outer-facing surface 40 of the first member plate 34 and the outer-facing surface 40' of the second member plate 34'. Any one or both of the first member plate 34 and the second member plate 34' may exhibit a flat shape on their outer-facing surfaces 40, 40'. Any one or both of the first member plate 34 and the second member plate 34' may exhibit a flat shape on their inner-facing surfaces 38, 38'. The gripping structure 29, 29' can be a strip of the textured surface or dimpled surface adjacent the cross-beam 26, 26' edge, where the remaining outer-facing surface 40, 40' of the plate 34, 34' may smooth or otherwise not textured.

Figure 12:
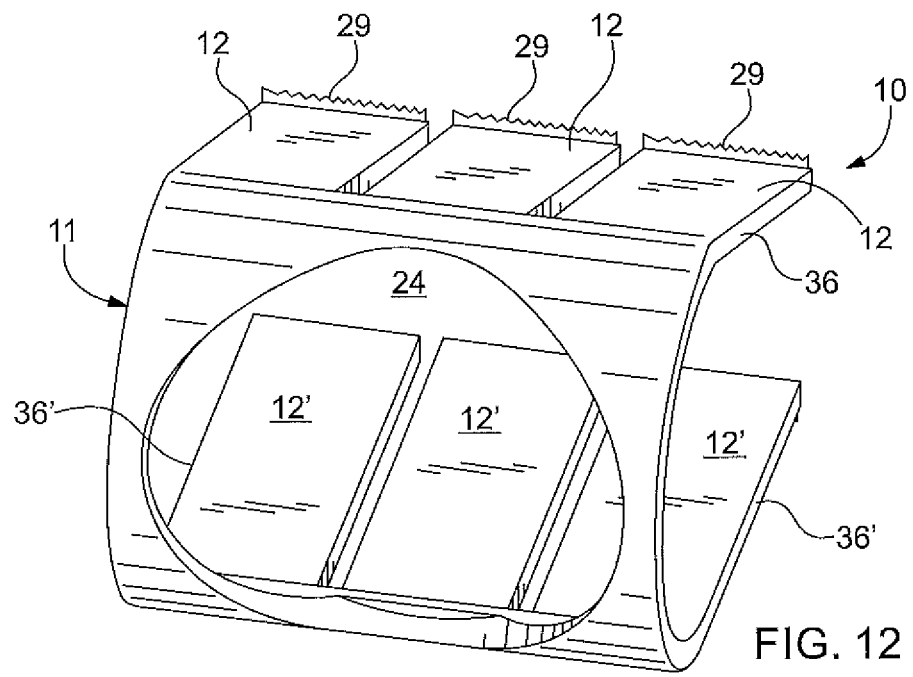
FIGS. 12-13 show perspective views of an exemplary embodiment of the device with a unitary hinging unit connecting a plurality of first members with a plurality of second members.
Figure 13:
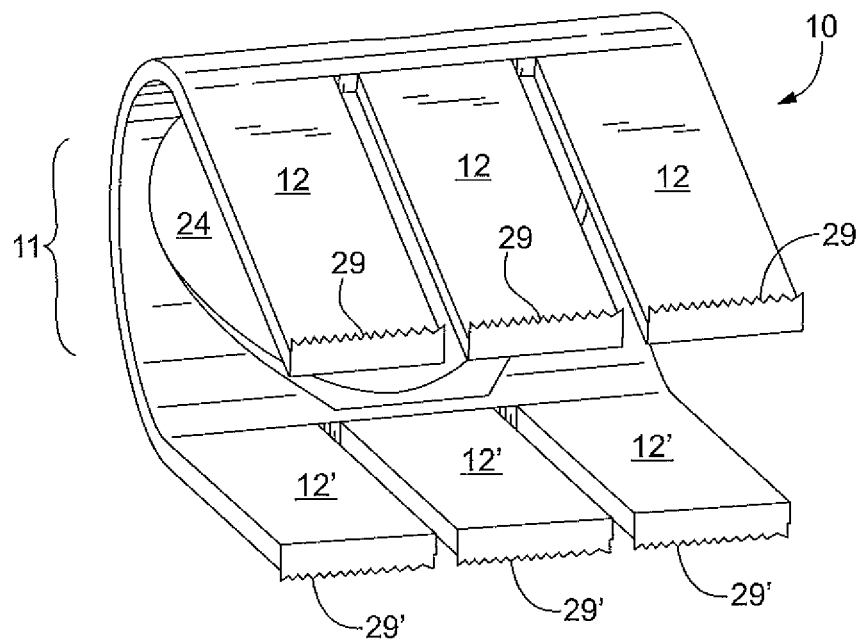

Referring to FIGS. 12-13, the device can include a unitary hinging unit 11 connecting a first member 12 with a second member 12'. The first member 12 can be structured to have a plurality of rectangular shaped spaced apart planks that can bend or resilient flex. At least a portion of any plank can be flexible while less distal portions of the plank may be semi-rigid or rigid. A gripping structure 29 can be disposed on an outer-facing surface 28 of each plank. In the embodiment illustrated in FIGS. 12-13, the device 10 can include multiple planks defined by the first member 12 to be arranged side-by-side. The second member 12' can be structured to have a plurality of rectangular shaped spaced apart planks. A gripping structure 29' can be disposed on an outer-facing surface 28' of each plank at a distal end of each plank. In the embodiment illustrated in FIGS. 12-13, the device 10 can include multiple planks defined by the second member 12' to be arranged side-by-side. Any of the gripping structures 29, 29' may be a row of teeth disposed along a distal edge of each plank opposite the junction(s) 16 or hinging unit 11. The hinging unit 11 can be a resilient material spanning a volume of space between the plurality of first members 12 and the plurality of second members 12' at a proximal end of the device 10. At least one plank of the first member 12 and at least one plank of the second member 12' can exhibit a flat outer-facing surface 40, 40'. At least one plank of the first member 12 and at least one plank of the second member 12' can exhibit a flat inner-facing surface 38, 38'. In one embodiment, the hinging unit 11 can be C-shaped. Further, the hinging unit 11 can include an opening 24, as described above. The opening 24 can be a circular shaped cut-out formed into the hinging unit 11 and be in communication with slits defined between adjacent planks of the first and second members 12, 12' and an inlet 24a defined at a proximal end of junction(s)16 and a mouth 24b defined at a distal end of the device 10 when the device 10 is in an open state.

Figure 14:
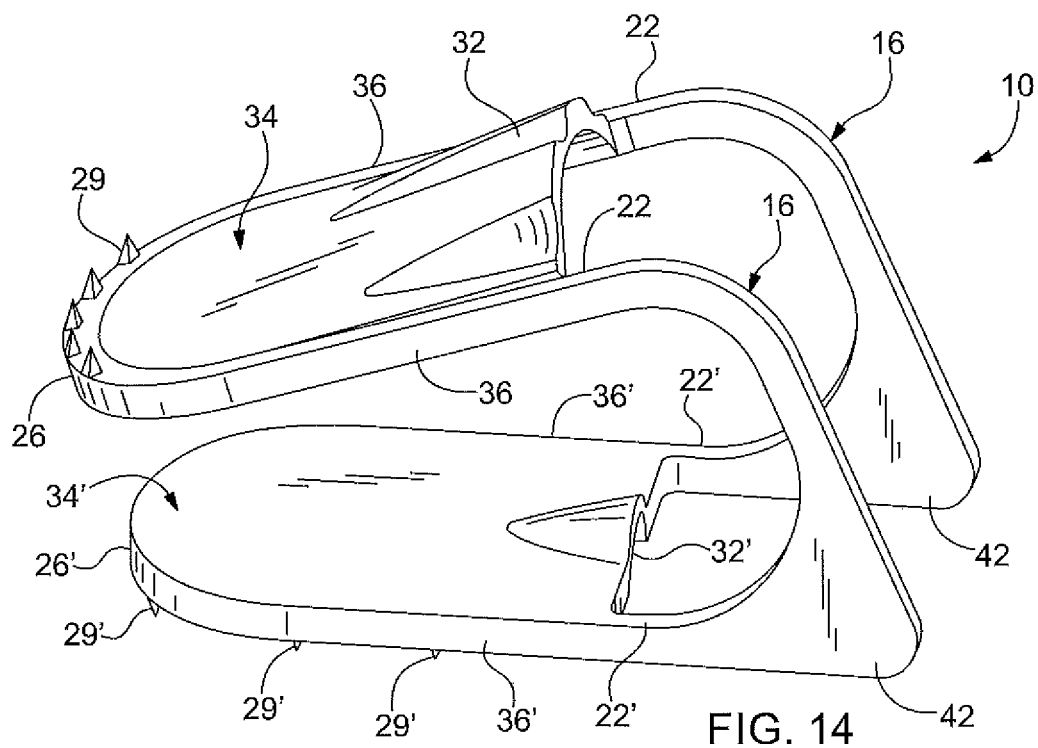
FIGS. 14-15 show perspective views of an exemplary embodiment of the device with second arms having an L-shaped rigid structure forming a gusset.
Figure 15:
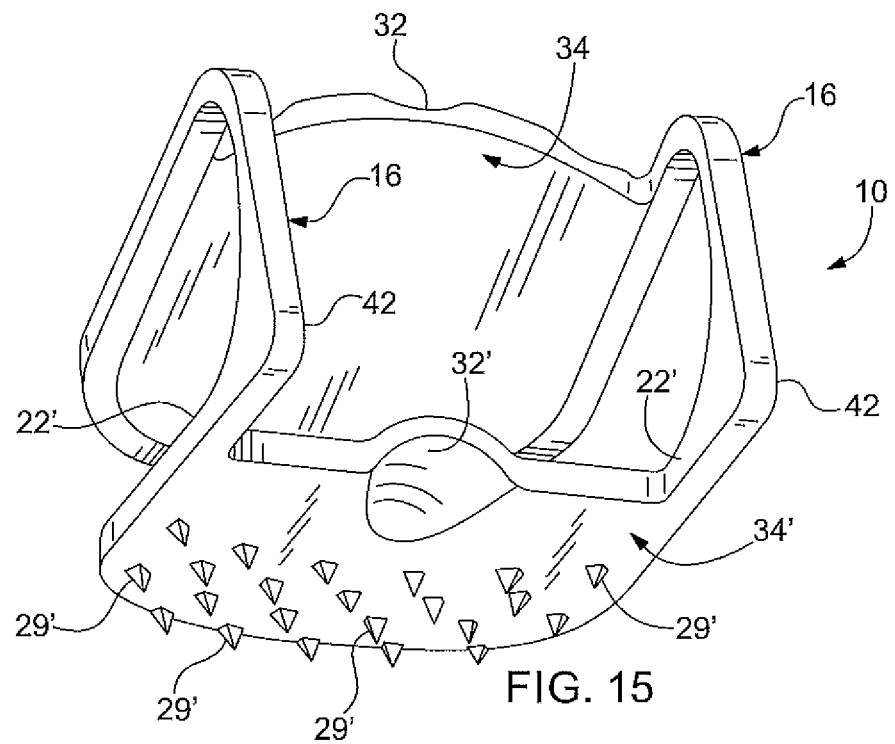
Figure 16:
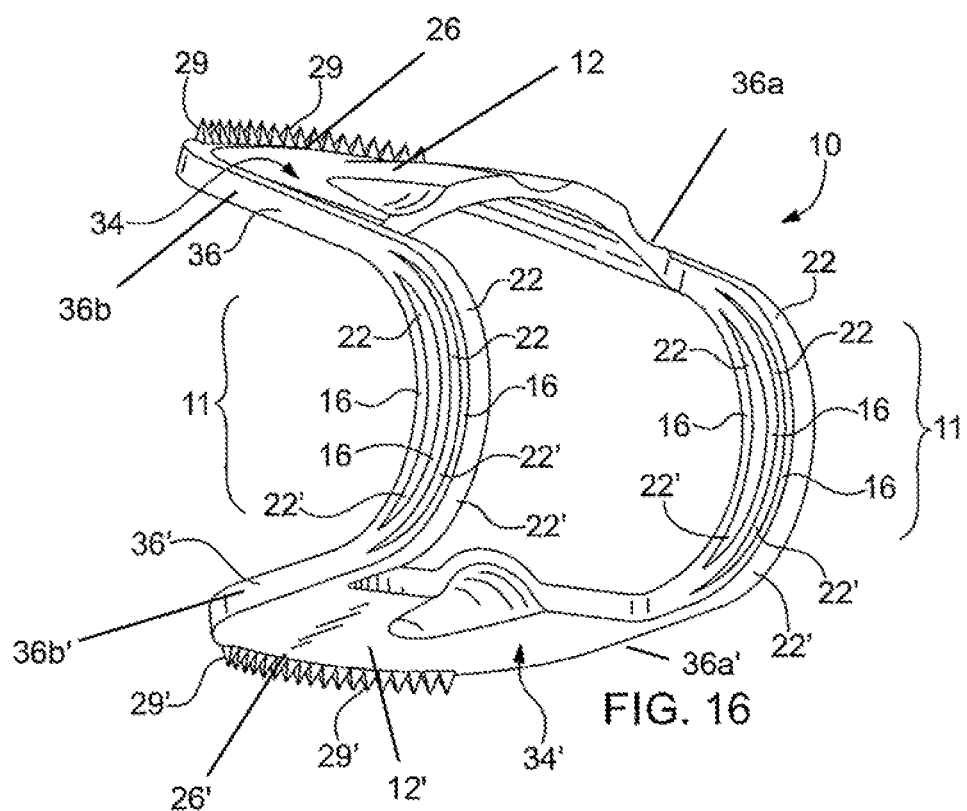
FIGS. 16-19 show perspective views of an exemplary embodiment of the device with a hinging unit having multiple sets of first and second arms.
Figure 17:
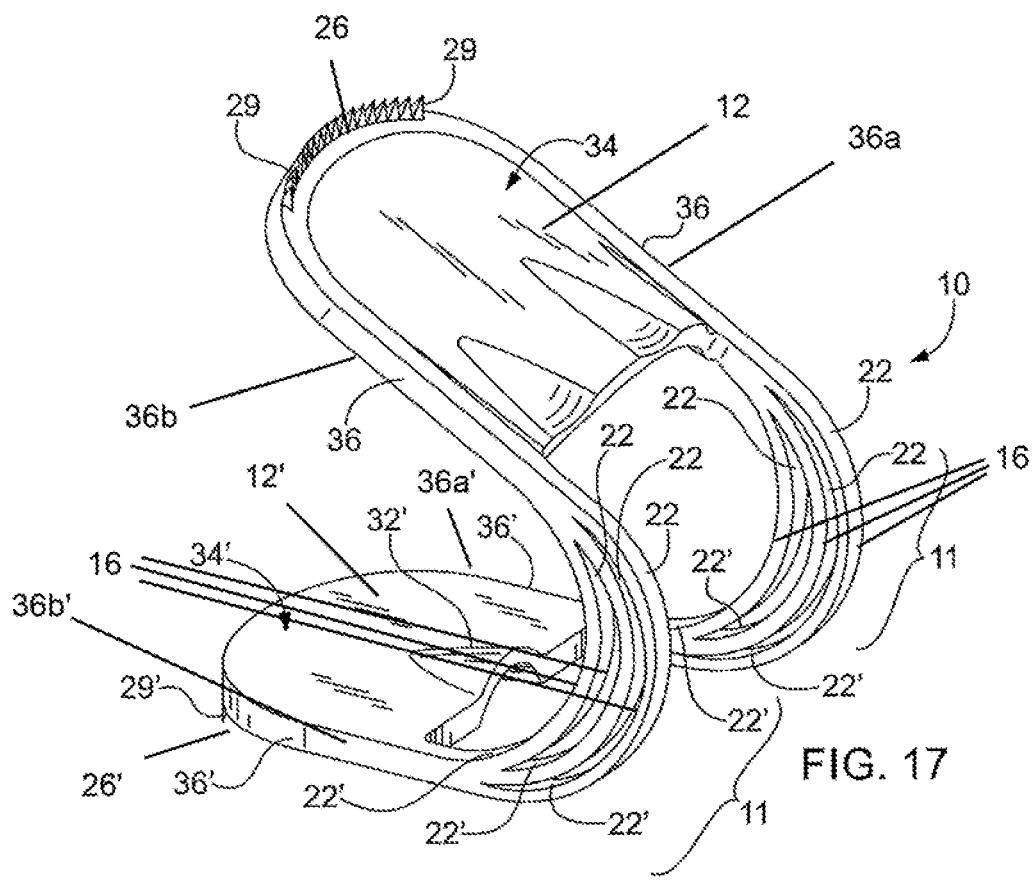
Figure 18:
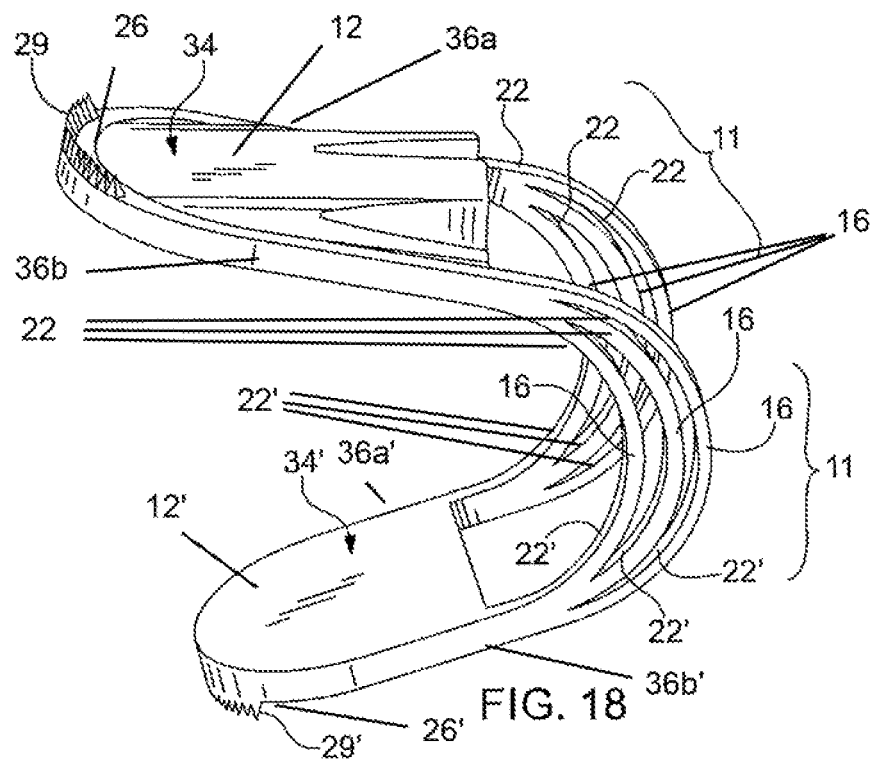
Figure 19:
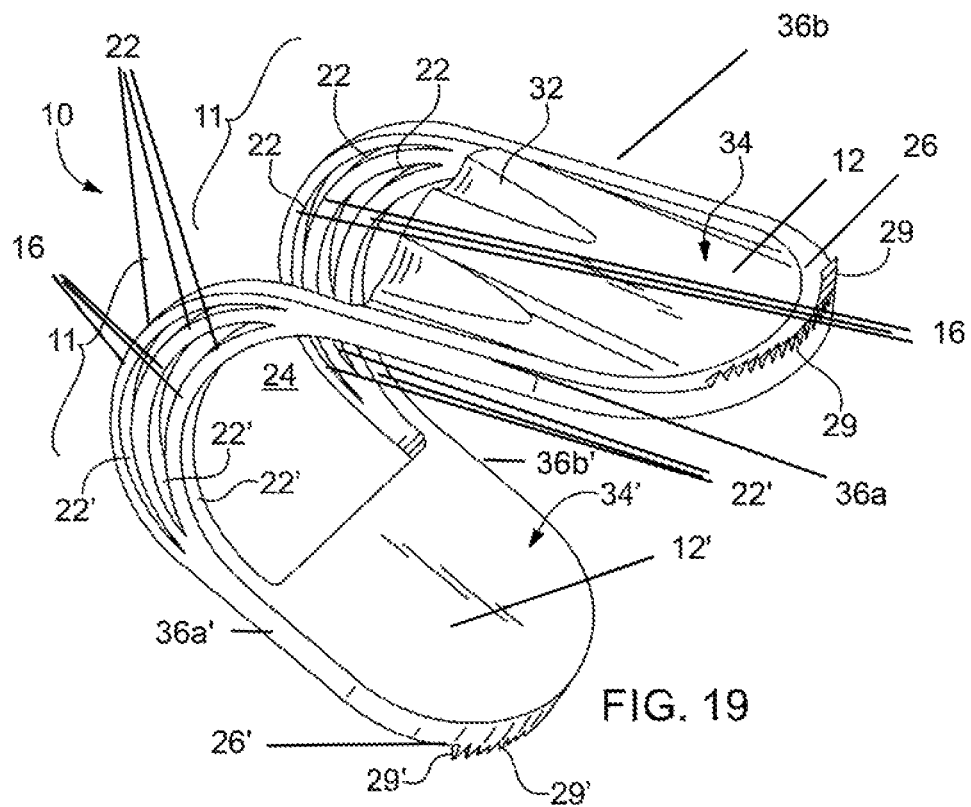

Referring to FIGS. 14-15, the hinging unit 11 can further include first arms 22 extending from the first and second side sections 36a, 36b of the first member 12, each first arm 22 leading to a separate junction 16. Each junction 16 can be resilient so as to allow deflection of the first member 12 relative to the second member 12', as described above. The hinging unit 11 can further include second arms 22' extending from the first and second side sections 36' of the second member 12'. At least one second arm 22' can be structured as an L-shaped rigid structure forming a gusset 42. Further, the device 10 can include a gripping structure 29, 29' structured as a row of teeth disposed along an edge of any one or both cross-beams 26, 26' and at least a portion of an edge of any one or each first and second side sections 36a-b, 36a'-b'. The gripping structure 29, 29' can further include teeth arranged along at least a portion of the outer-facing surface 40, 40' of at least one of the first member plate 34 and the second member plate 34'.

Referring to FIGS. 16-32, the device 10 can include a first member 12 having at least a first arm 22 extending from the first member 12. The device 10 can include a second member 12' having at least a first arm 22' extending from the second member 12'. A distal end of the first arm 22 of the first member 12 may be connected to a first end member and a proximal end of the first arm 22 of the first member 12 may be connected to a proximal end of the first arm 22' of the second member 12' at a first junction 16. A distal end of the first arm 22 of the second member 12' can be connected to the second member 12'. The first and second members 12, 12' can be at least one of statically, resiliently, and pivotally connected via a first junction 16 such that the first member 12 may be moveable relative to the second member 12' about the first junction 16. The first junction 16 can be configured to provide a biasing force to move the first and second members 12, 12' away from each other to position the device 10 in an open state. The first member 12 may be movable relative to the second member 12' about the first junction 16 from the open state to a closed state. At least a portion of the first member 12 may be abuttable with at least a portion of the second member 12' when the device 10 is in the closed state. A junction 16 can have its components varied to adjust the compression/expansion spring force of the device 10. An in-plane width of the individual elements, combined with a gap between the individual elements can allow the user to select a defined range of motion, specific closure, as well as a specific retraction spring force and range of that force, as dictated by the needs of a particular surgery. The individual elements that may be combined to make a specific device 10's performance, can have differing in-plane widths and differing gaps from one element to another, even side to side. Further, additional function and controls of spring rates can occur if the individual elements are also formed to be out of plane, to provide additional access for the surgeon, or to be able to apply asymmetrical spring expansion for a particular surgical situation, for example a combination of side tissue distraction combined with a horizontal distraction.

For example, the first arm 22 of the first member 12 may extend from the first member 12 adjacent a first side 36a of the first member 12. The first member 12 can further have a second arm 22 and a third arm 22 extending from adjacent the first side 36a of the first member 12. The second arm 22 can be positioned between the first and third arms and be spaced apart from those arms at least throughout an intermediate portion of the arms. The first member 12 can also have a fourth arm 22, fifth arm 22, and sixth arm 22 that each extends from adjacent the second side 36*b* of the first member 12. The second side 36*b* may be opposite the first side 36*a*. The fifth arm 22 of the first member 12 may be located between the fourth and sixth arms 22 of the first member 12 and be spaced apart from those arms at least throughout an intermediate portion of the arms. The first arm 22 of the first member 12 may be aligned with the fourth arm 22 of the first member 12. The second arm 22 of the first member 12 may be aligned with the fifth arm 22 of the first member 12. The third arm 22 of the first member 12 may be aligned with the sixth arm 22 of the first member 12.

The first arm 22' of the second member 12' may extend from the second member 12' adjacent a first side 36*a*' of the second member 12'. The second member 12' can further have a second arm 22' and a third arm 22' that each extends from adjacent the first side 36*a*' of the second member 12' such that the second arm is between the first and third arms and is spaced apart from those arms at least throughout an intermediate portion of the arms. The second member 12' can further have a fourth arm 22', fifth arm 22' and sixth arm 22' that each extend from adjacent the second side 36*b*' of the second member 12' that is opposite the second member's first side 36*a*'. The fifth arm of the second member can be between the fourth and sixth arms of the second member 12' and can be spaced apart from those arms at least throughout an intermediate portion of the arms. The first arm 22' of the second member 12' may be aligned with the fourth arm 22' of the second member 12'. The second arm 22' of the second member 12' may be aligned with the fifth arm 22' of the second member 12'. The third arm 22' of the second member 12' may be aligned with the sixth arm 22' of the second member 12'.

In some embodiments, distal ends of the second arm 22, third arm 22, fourth arm 22, fifth arm 22, and sixth arm 22 of the first member 12 may be attached to at least one of a first plate 34 and a first cross-beam 26 of the first member 12. Distal ends of the second arm 22', third arm 22', fourth arm 22', fifth arm 22', and sixth arm 22' of the second member 12' may be attached to at least one of a second plate 34' and a second cross-beam 26' of the second member 12'. A proximal end of the second arm 22 of the first member 12 can be attached to a proximal end of the second arm 22' of the second member 12' at a second junction 16. A proximal end of the third arm 22 of the first member 12 can be attached to a proximal end of the third arm 22' of the second member 12' at a third junction 16 such that the second junction 16 is between the first and third junctions 16. A proximal end of the fourth arm 22 of the first member 12 can be attached to a proximal end of the fourth arm 22' of the second member 12' at a fourth junction 16. A proximal end of the fifth arm 22 of the first member 12 can be attached to a proximal end of the fifth arm 22' of the second member 12' at a fifth junction 16. A proximal end of the sixth arm 22 of the first member 12 can be attached to a proximal end of the sixth arm 22' of the second member 12' at a sixth junction 16 such that the fifth junction 16 is between the fourth and sixth junctions 16. The first member 12 may be movable relative to the second member 12' between the open state and the closed state about the first junction 16, second junction 16, third junction 16, fourth junction 16, fifth junction 16, and sixth junction 16. These junctions can be configured so that the first member 12 is biased to be moveable relative to the second member 12' about the junctions to move the device into the open state of the device 10.

Referring to FIGS. 16-19, the device 10 can further include a plurality of first and second arms 22, 22' for each side section 36*a-b*, 36*a'-b'*. For example, the hinging unit 11 can include a plurality of first and second arms 22, 22' connecting the first member first side section 36 with the second member first side section 36*a*' via a plurality of junctions 16. Similarly, the hinging unit 11 can further include a plurality of first and second arms 22, 22' connecting the first member second side 36*b* section with the second member second side section 36*b*' via a plurality of junctions 16. In other words, the hinging unit 11 can include a multiple sets of first and second arms 22, 22'. In some embodiments, a set may exhibit more or less rigidity (more or less restoring force; more or less biasing force) than that of another set. For example, the first set may comprise of a material with a certain level of rigidity, whereas the second set, third set, and/or other sets may be composed of a material with a lesser or greater level of rigidity that that of the first set. In other embodiments, each set may exhibit the same or similar restoring force than that of another set.

Figure 20:
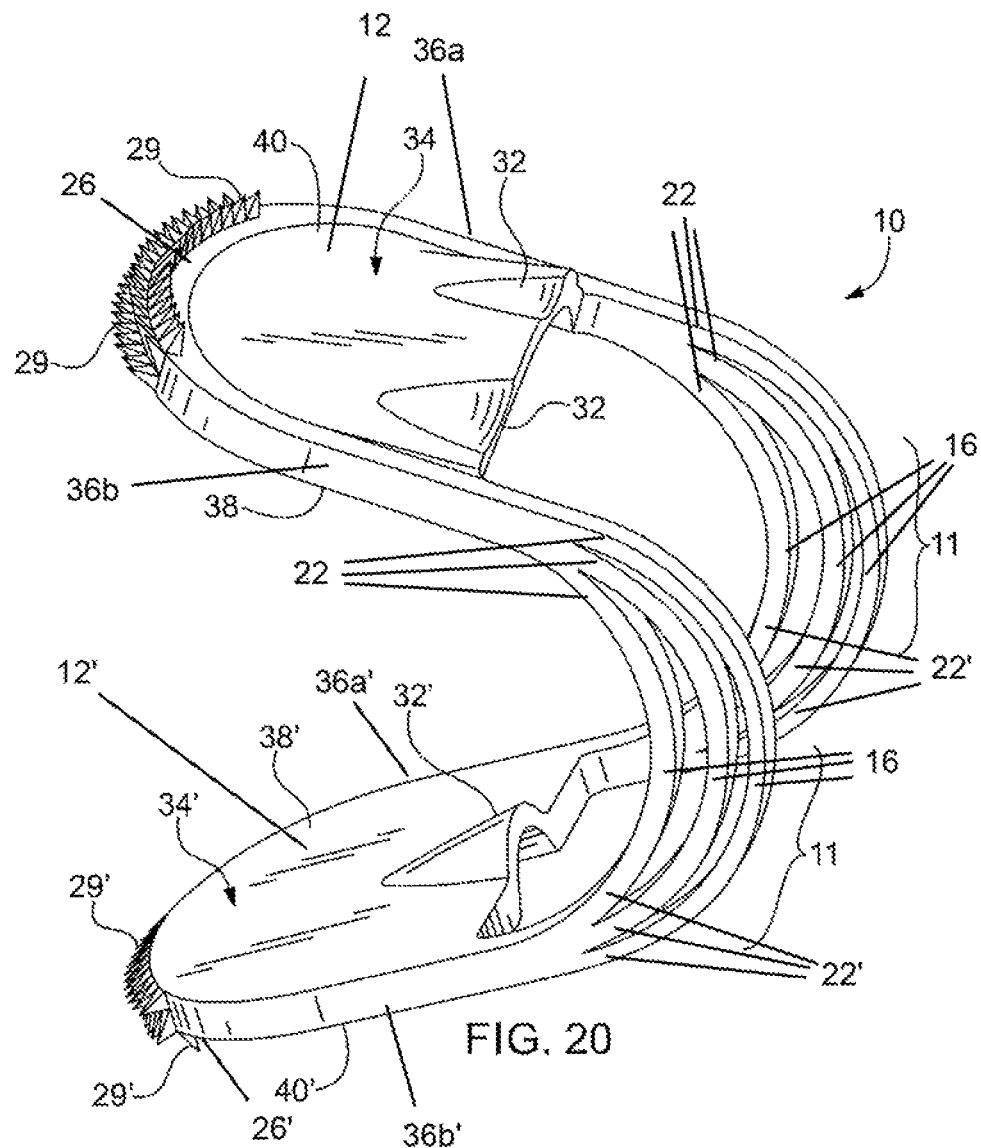
FIG. 20 shows perspective view of an exemplary embodiment of the device with a gripping structure formed as a plurality of rows of teeth disposed along an edge of each cross-beam.

Referring to FIG. 20, the device 10 can further include a gripping structure 29, 29' structured as a plurality of rows of teeth disposed along an edge of at least one or both cross-beams 26, 26' and/or on at least one plate 34, 34'. For example, a first row of teeth can be disposed on an outer-facing surface 40, 40' of any one of the first member plate 34 and the second member plate 34', wherein the first row can be adjacent the edge of the cross-beam 26, 26' and facing at an angle normal to the outer-facing surface 40, 40'. A second row of teeth can be disposed on any one cross beam 26, 26', wherein the second row can be adjacent the first row and facing at an that is between normal to and perpendicular to the outer-facing surface 40, 40'. A third row of teeth can be disposed on any one cross beam 26, 26', wherein the third row can be adjacent the second row and facing at an angle perpendicular to the outer-facing surface 40, 40'.

Figure 21:
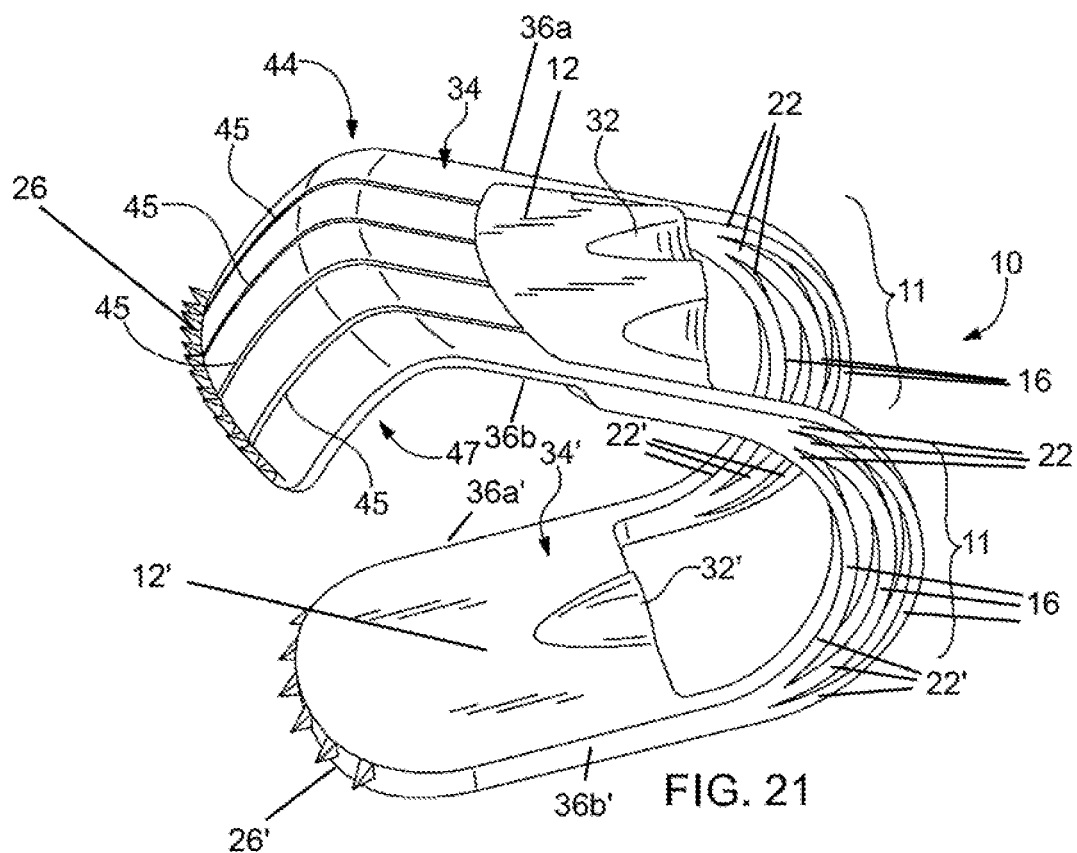
FIGS. 21-22 show perspective views of an exemplary embodiment of the device with a first member plate comprising an angled structure.
Figure 22:
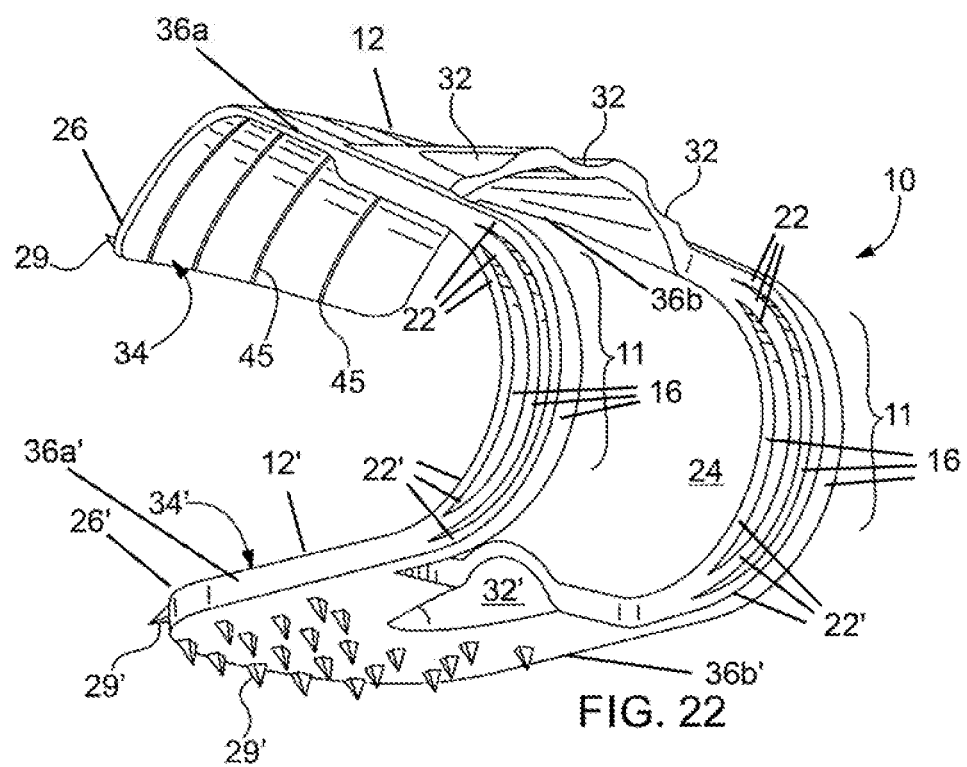

Referring to FIGS. 21-22, the device 10 can further include at least one of the first member plate 34 and the second member plate 34' comprising an angled structure 44. For example, the first member plate 34 can be structured to have an angle awning section 47. Further, the device 10 can include flutes 45 formed into a surface of at least one of the first member plate 34 and the second member plate 34'. This can be done to provide added structural rigidity to the plate 34, 34'. The device 10 can further include a gripping structure 29, 29' structured as a plurality of rows of teeth disposed along an edge of both cross-beams 26, 26', as described above. In some embodiments, the device 10 can include a gripping structure 29, 29' structured as a plurality of teeth disposed on at least a portion of an outer-facing surface 40, 40' of at least one of the first member plate 34 and the second member plate 34', as described above.

Figure 23:
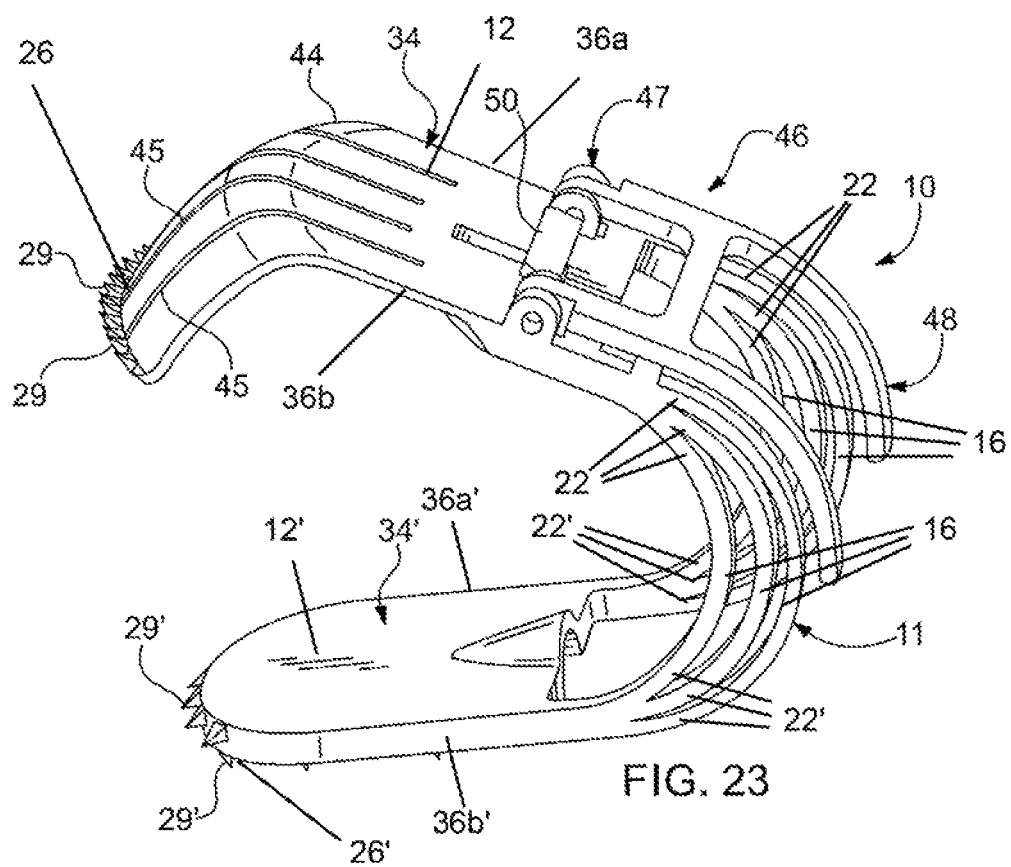
FIGS. 23-24 show perspective views of an exemplary embodiment of the device with a holding means that selectively locks the device in a closed state.
Figure 24:
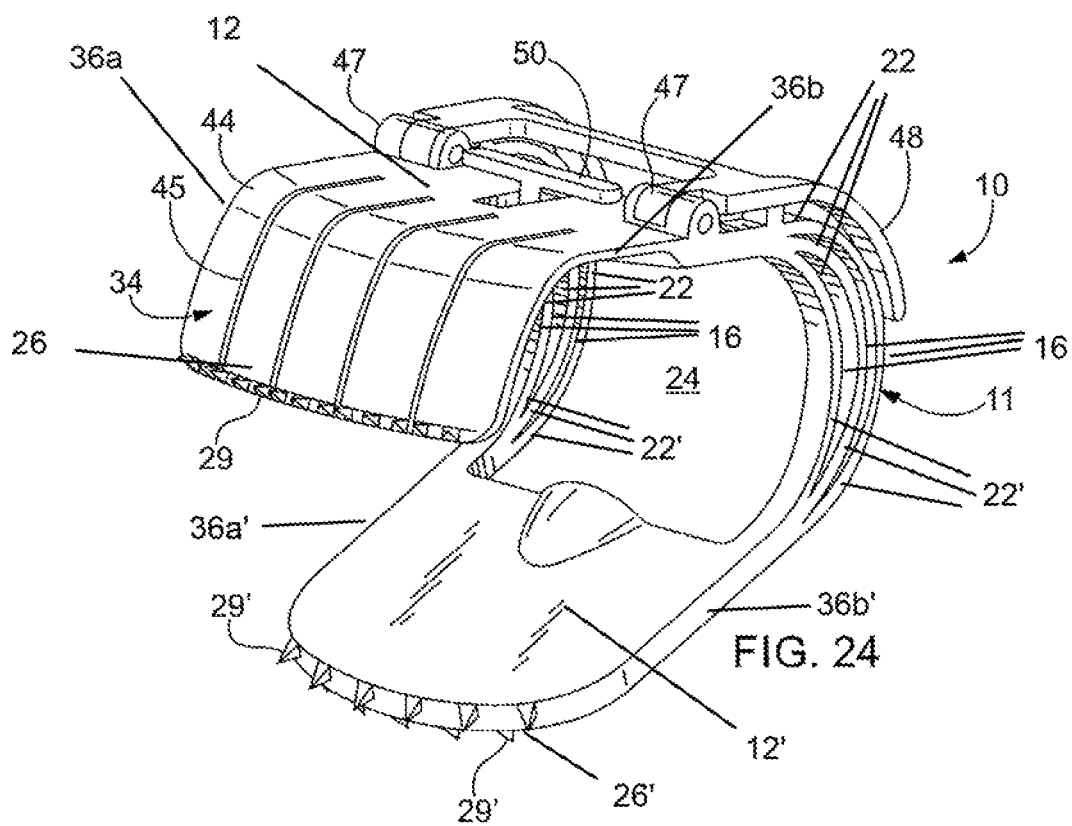

Referring to FIGS. 23-24, the device can further include a holding means 46 that selectively locks the device 10 in a closed state, open state, or any other intermediary state. The holding means 46 can be located on the first member 12 and/or first member plate 34. In some embodiments, the device 10 can include a ratcheting mechanism 47 located on at least one of the first side section 36*a* and the second side section 36*b*. The holding means 46 may further be configured to transition the device 10 from the open state to the closed state in addition to locking the device 10 in a state. For example, the holding means 46 can be configured with a ratcheting mechanism 47 with a ratcheting arm 48 and a release 50. As the ratcheting arm 48 is actuated, the ratcheting mechanism 47 (e.g., ratchet wheel) can draw at least one first arm 22 toward the first member plate 34 by engaging teeth of a surface of the first arm 22. This can cause the device 10 to transition from the open state to the closed state. In some embodiments, the ratcheting mechanism 46 can be cam-shaped. A user can use ratcheting mechanism 47 to lock the device 10 in a desired closed state for insertion. Actuating the release 50 can cause the ratchet mechanism 47 to disengage from the teeth of the first arm(s) 22, and thus allow the device 10 to transition from the closed state to the open state.

Figure 25:
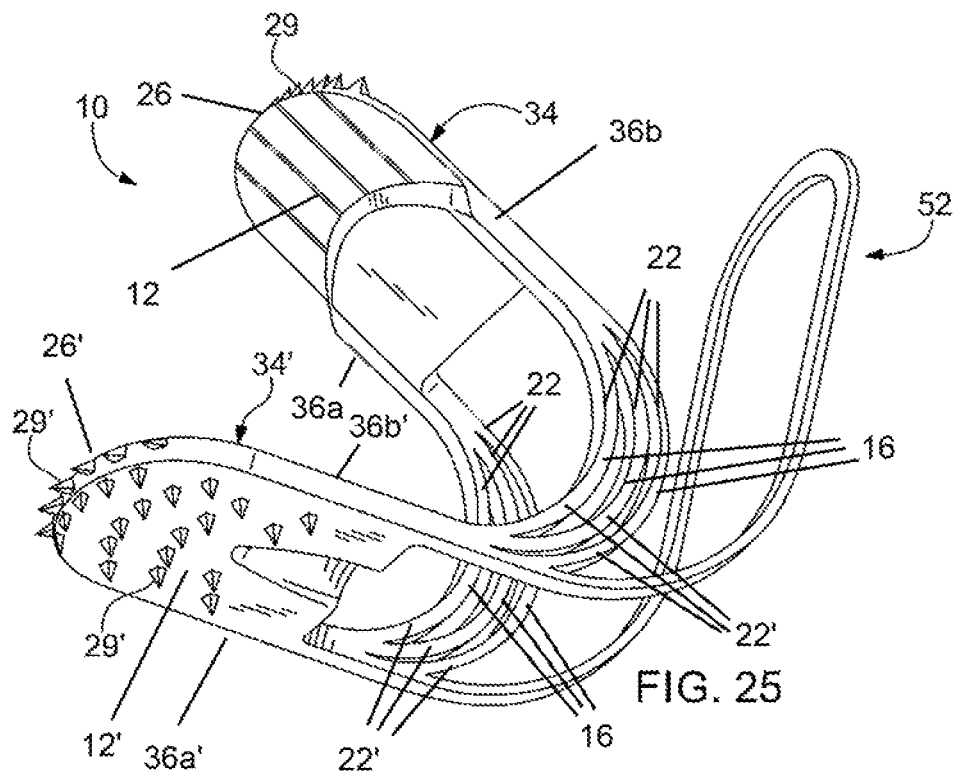
FIGS. 25-26 show perspective views of an exemplary embodiment of the device with a tenting apparatus.
Figure 26:
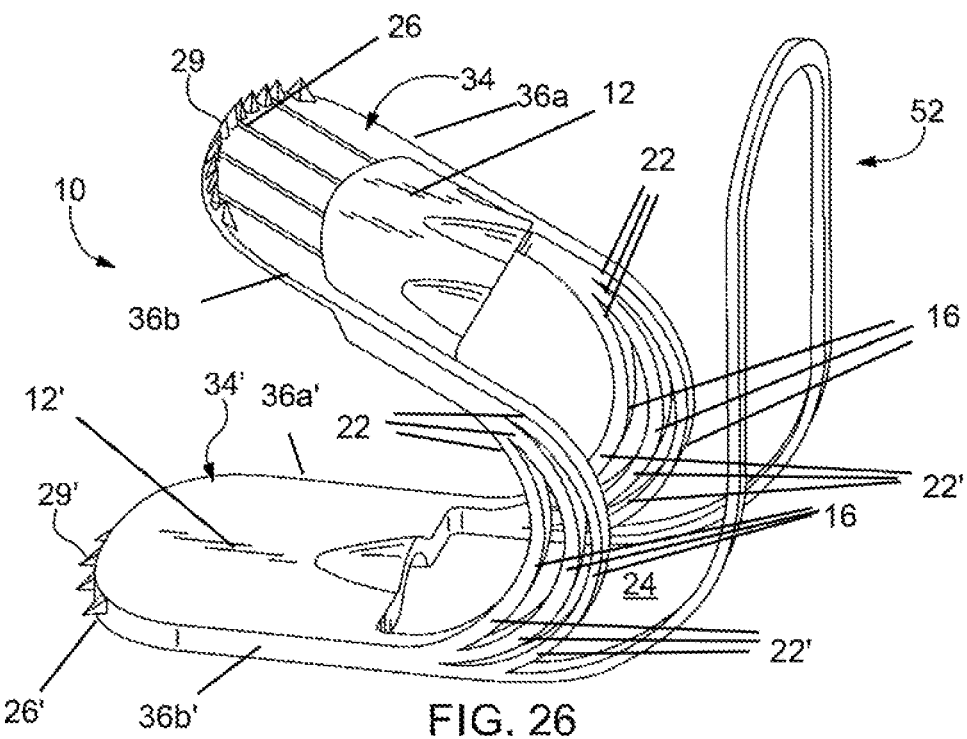

Referring to FIGS. 25-26, the device can further include a tenting apparatus 52. The tenting apparatus 52 can include an element extending from at least one second arm 22' and angled upward to be approximately perpendicular with a geometric plane of the second member 14. For example, the tenting apparatus 52 can extend from each second arm 22', and angle upwards to be approximately perpendicular to the second member 12' where it forms a U-shaped element. The tenting apparatus 52 can provide added propping support for the skin flap by allowing the skin flap to rest upon a top of the tenting apparatus 52, as well as the first member 12. For example, a device 10 with a tenting apparatus 52 may be used for surgeries that include larger subcutaneous pockets, and thus larger skin flaps. In some embodiments, the tenting apparatus 52 can be an open structure so as to facilitate access to the opening 24. While the tenting apparatus 52 is envisioned to be rigid enough to adequately prop up and support a skin flap, the tenting apparatus 52 can exhibit some resiliency so as to facilitate some deflection.

Figure 27:
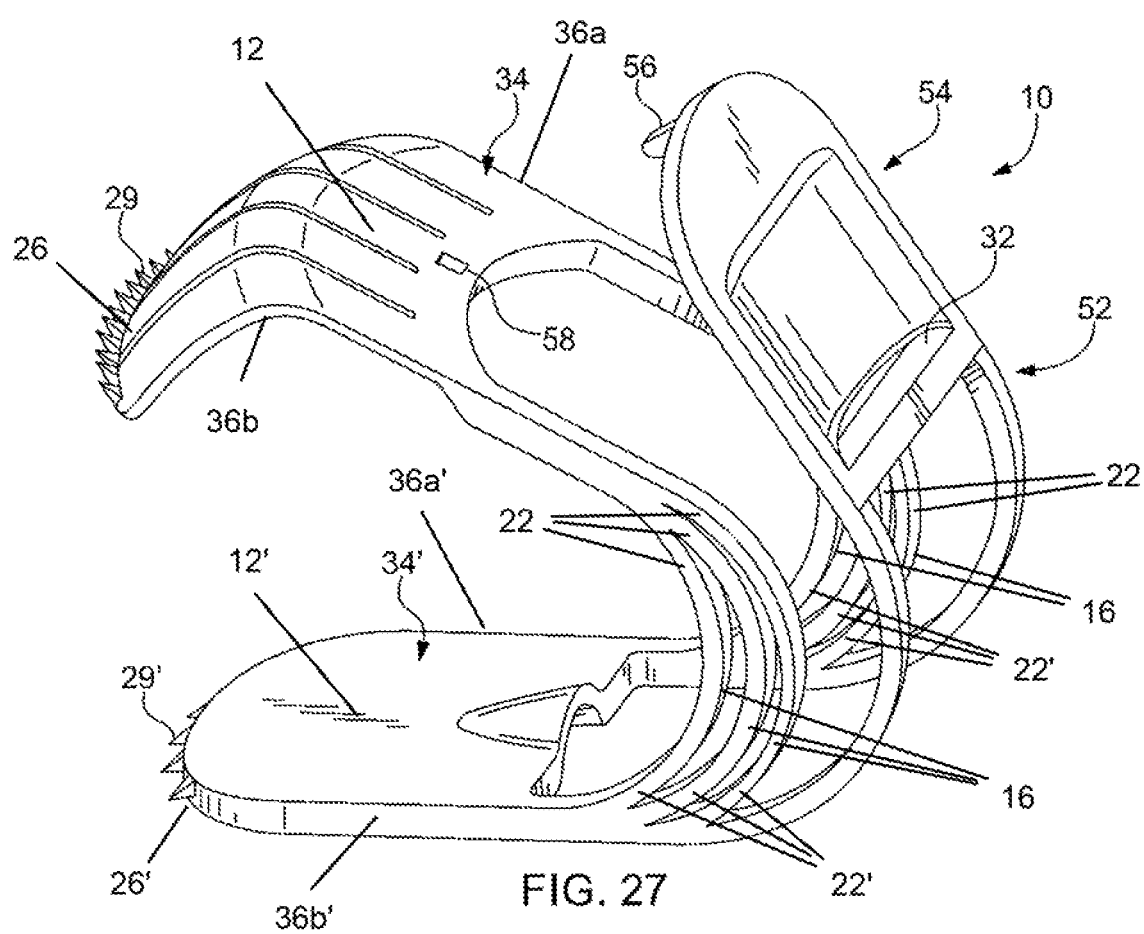
FIGS. 27-28 show perspective views of an exemplary embodiment of the device with a tenting plate element and a latching mechanism in uses with the tenting apparatus.
Figure 28:
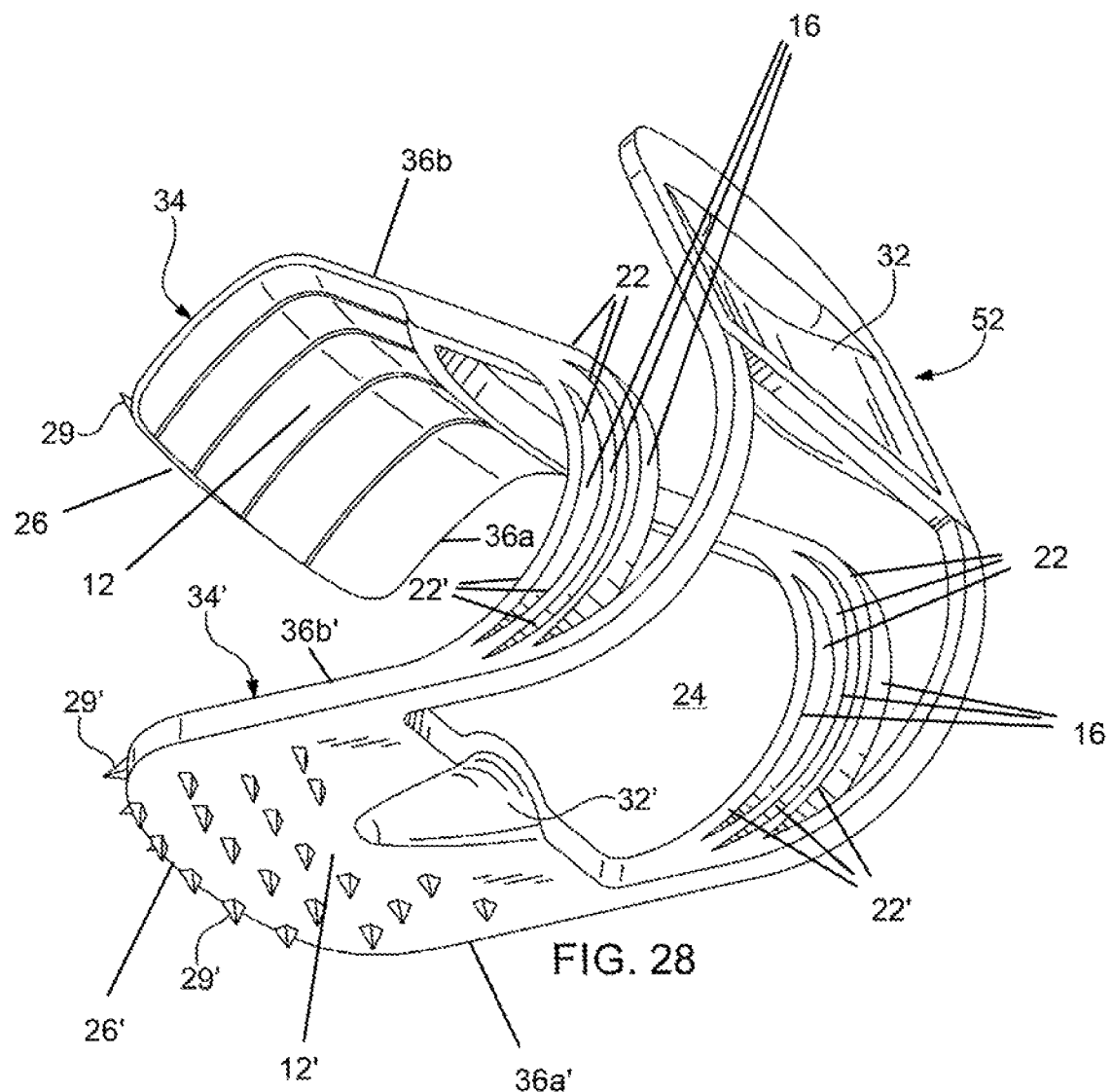

Referring to FIGS. 27-28, the device 10 can further include a tenting plate element 54 within a portion of the tenting apparatus 52. For example, the tenting plate element 54 can be placed at a top portion of the tenting apparatus 52. The tenting apparatus 52 can be configured to exhibit some resiliency so as to enable movement of the tenting apparatus 52. In some embodiments, the tenting apparatus 52 can be moved from an approximate perpendicular angle relative to the second member 12' to abut against the first member 12 and/or first member plate 34. For example, the tenting apparatus 52 can be rotatingly attached to the device 10 at the second arm(s) 22'. As another example, the attachment of the tenting apparatus 52 at the second arms 22' can be such that the tenting apparatus 52 is deflectable about an axis of rotation at the interface between the tenting apparatus 52 and the second arm(s) 22'. In further embodiments, the tenting apparatus 52 can include a latch mechanism 56 to temporarily hold the tenting apparatus 52 against the first member 12 and/or first member plate 34. The latching mechanism 56 can be a protrusion extending from a surface of the tenting apparatus 52 that may form an interference fit with a latching aperture 58 formed into the first member 12 and/or first member plate 34. Other latching mechanisms can be used, such as a magnetic clasp, a rotatable latch, etc. The device 10 further include a finger retainer 32 formed with the tenting plate element 54 to assist a user in manipulation of the tenting apparatus 52. For example, a user may insert a finger within the finger retainer 32 to pull on and/or push on the tenting apparatus 52 to cause it to move within the range of motion described above and/or to cause the tenting apparatus 52 to engage or disengage the first member 12 and/or first member plate 34 via the latching mechanism 56.

Figure 29:
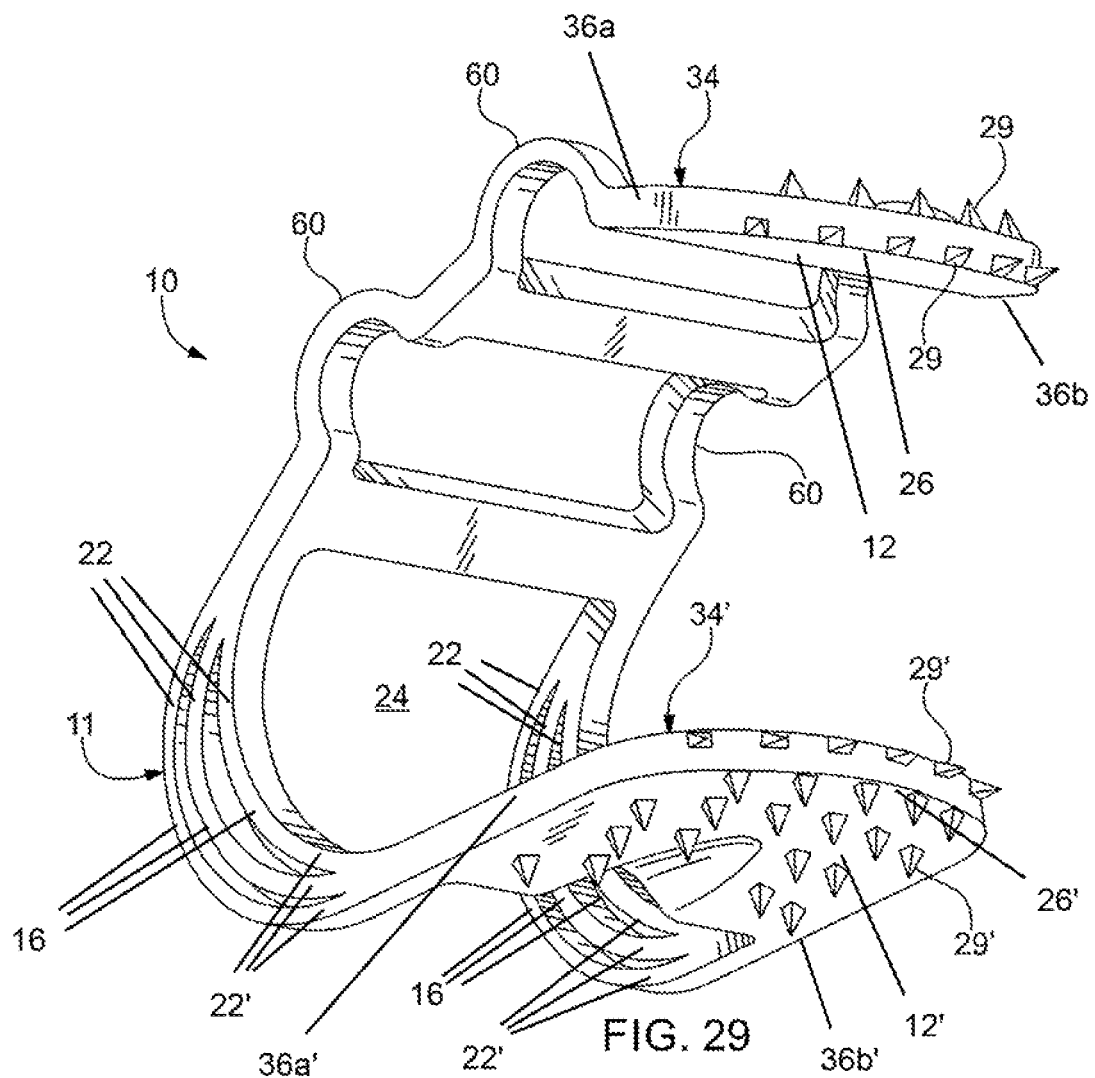
FIGS. 29-30 show perspective views of an exemplary embodiment of the device with at least one finger joint.
Figure 30:
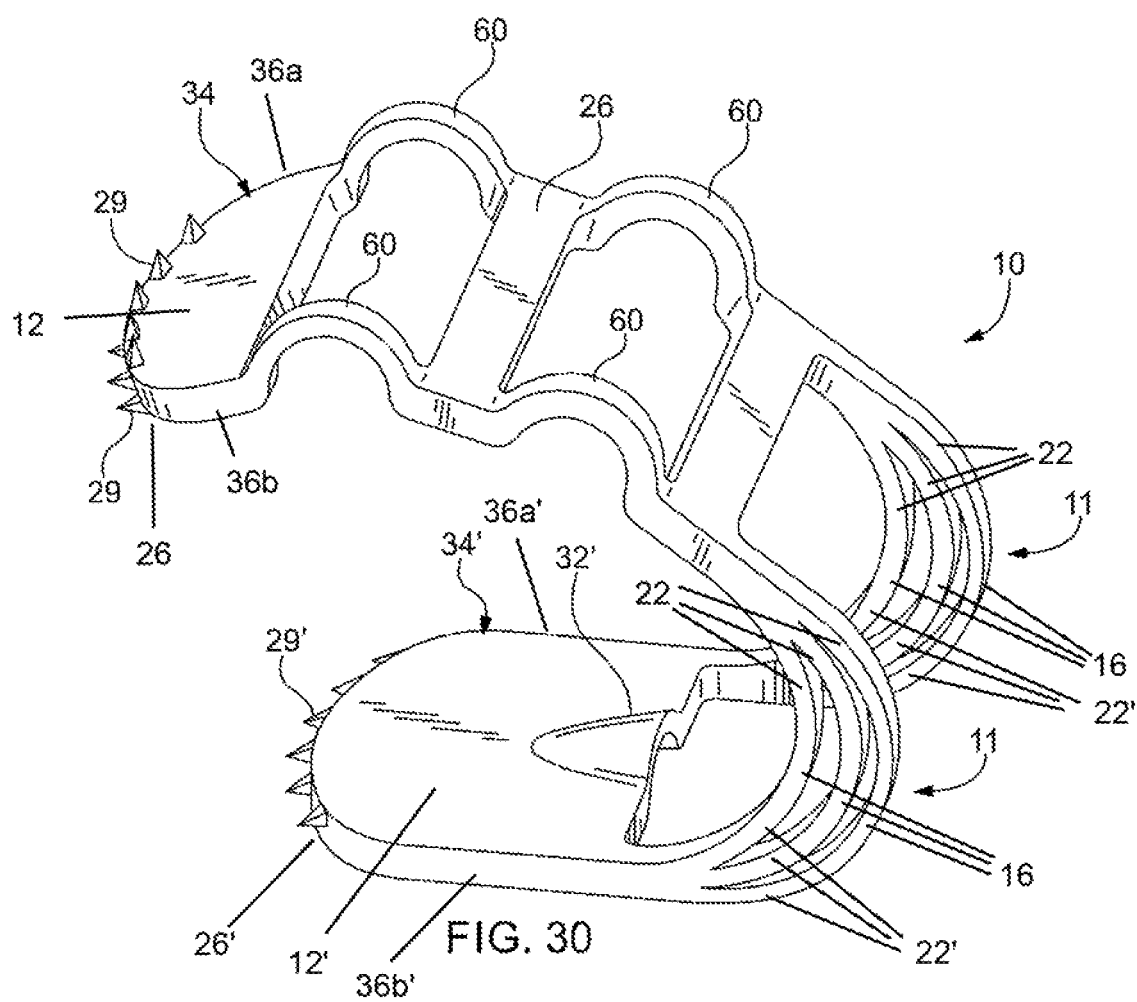

Referring to FIGS. 29-30, the device 10 can further include at least one finger joint 60 formed into at least one of the first side section 36a and the second side section 36b in the first member 12 and/or second member 12'. Further, the device 10 can include at least one finger joint 60 formed into at least a portion of the first member plate 34 and/or second member plate 34'. Any one of the finger joints 60 can be a semi-circular shaped formation, arch shaped formation, etc. A finger joint 60 can facilitate local distraction forces, applied on the uppermost tissue by a first member plate 34, to be applied forward and upward, in relation to the second member plate 34'. This may allow for better tension and/or counter-tension distraction of the tissue plane. For example, a user can insert a finger or other object within a finger joint 60 and cause the first member 12 to further move away from the second member 12'. A user can do this while the device 10 is within the incision and during and/or after the transitioning of the device 10 from the closed state to the propped state. This may be particularly advantageous if the device 10 is used on the breast skin from the breast tissue, for example.

Figure 31:
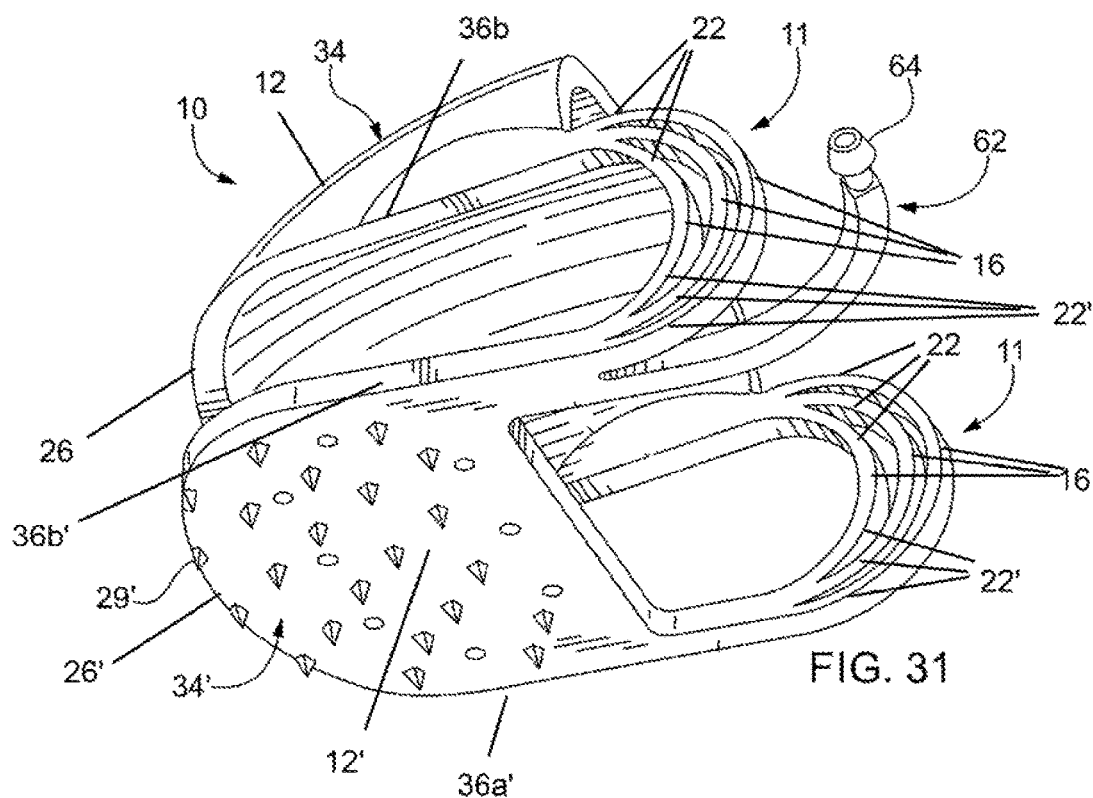
FIGS. 31-32 show perspective views of an exemplary embodiment of the device with a vacuum conduit.
Figure 32:
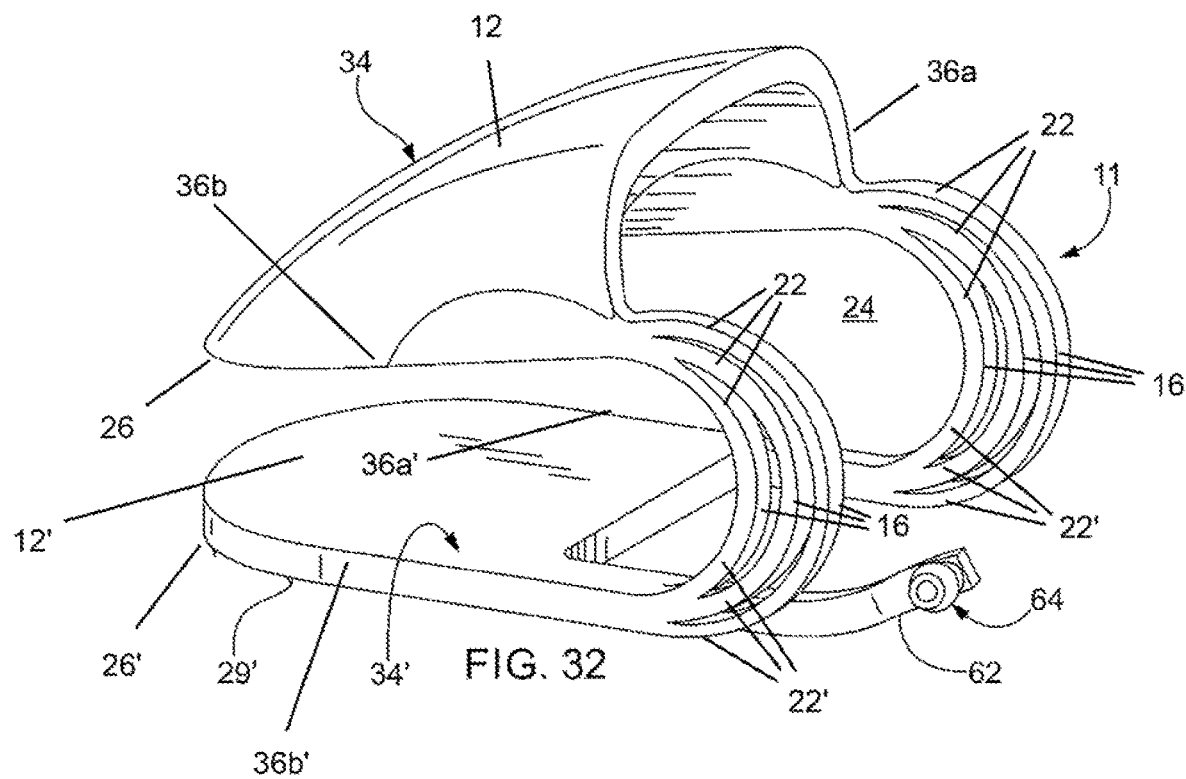

Referring to FIGS. 31-32, the device 10 can further include a vacuum conduit 62 extending from at least one of the second arm(s) 22', the second member 12', and/or the second member plate 34'. The vacuum conduit 62 can include a nipple 64 to facilitate a quick-disconnect connection to a vacuum source (e.g., a pump or plunger). A distal end to the vacuum conduit 62 may include an opening located at an in inner-facing surface 30,38' and/or outer-facing surface 28',40' of the second member 12' and/or second member plate 34'. The vacuum conduit 62 can exhibit a straight shape, curved shape, or other shape. For example, the vacuum conduit 62 can exhibit a curved shape so as to not obstruct view and/or access to the opening 24. In further embodiments, the vacuum conduit 62 can be bent to a desired shape and/or position. For example, at least a portion of the vacuum conduit 62 can be fabricated from malleable or formable material so as to allow a user to manually bent and form the conduit into a desired position. Further, as can be seen in the figures, the first member plate 34 can have a dome shape. In other embodiments, the device 10 can further include a dome element (not shown) positioned over the first member plate 34.

Figure 33:
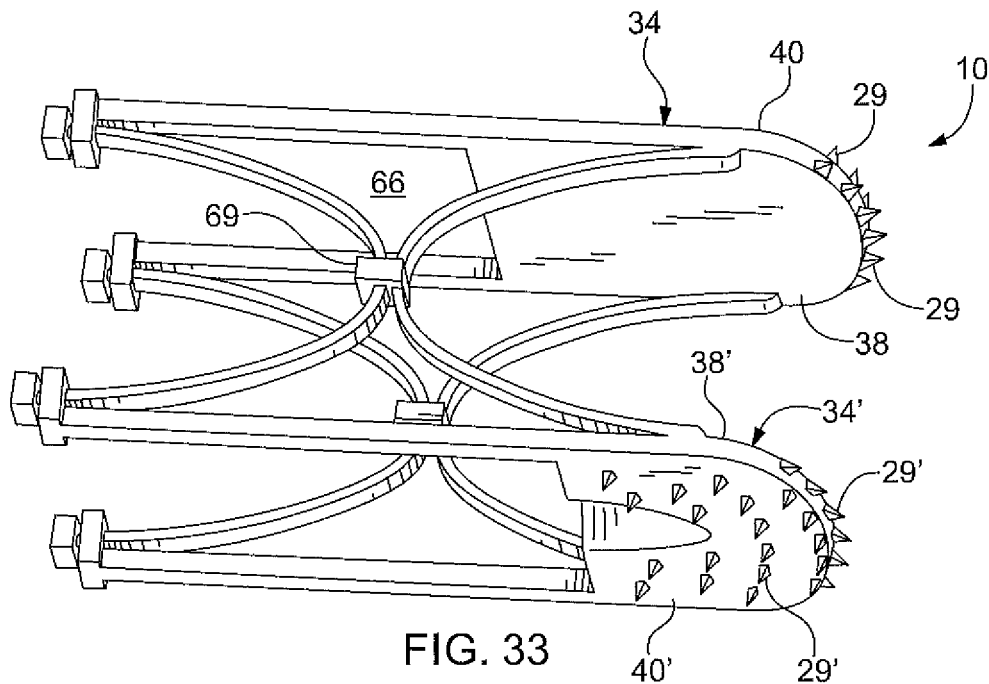
FIGS. 33-34 show perspective views of an exemplary embodiment of the device with a hinging unit structured as at least one leaf-spring element.
Figure 34:
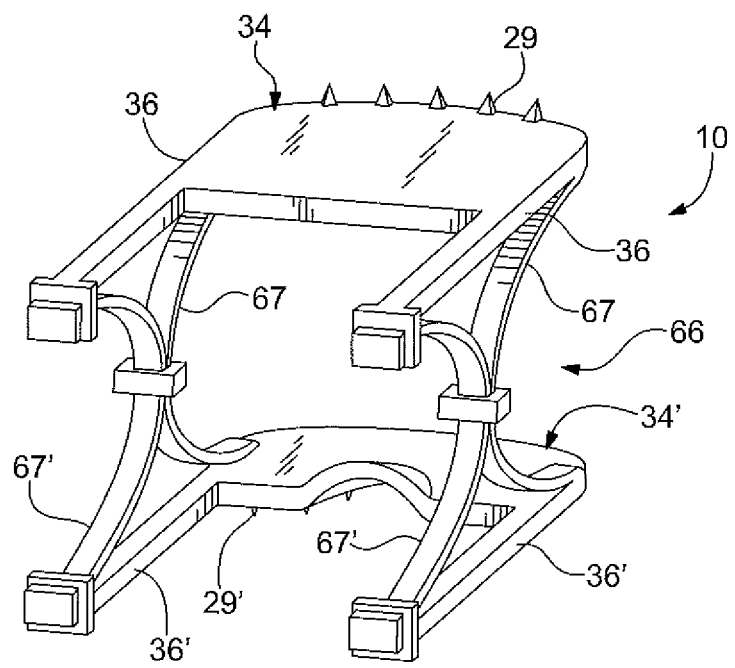

Referring to FIGS. 33-34, the hinging unit 11 can include at least one leaf-spring element 66. For example, the device 10 may include a first set of leaf-spring elements 66 positioned along the first side sections 36a, 36a' and a second set of the leaf-spring elements 66 positioned along the second side sections 36b, 36b'. Each set may include a U-shaped resilient member 67 coupled to another U-shaped resilient member 67'. For example, the first set of leaf-spring elements 66 can include a U-shaped resilient member coupled to another U-shaped resilient member by a coupler at an apex of each U-shaped member. The second set of leaf-spring elements 66 can include a U-shaped resilient member coupled to another U-shaped resilient member by a coupler at an apex of each U-shaped member. The first set of leaf-spring elements 66 may run parallel with, and even be aligned with, the first side sections 36a, 36a'. The second set of leaf-spring elements 66 may run parallel with, and even be aligned with, the second side sections 36b, 36b'. The hinging unit 11 structured as at least one leaf-spring element 66 can facilitate transitioning the device 10 to and from an open state and a closed state by motioning the first member 12 relative to the second member 14 in a longitudinal manner as opposed to a rotational manner. For example, a user may motion the first member 12 towards the second member 12' by compressing the first and second sets of leaf-spring elements 66. With the device 10 held in the compressed position (i.e., the closed state), the device 10 can be inserted into an incision or between two objects of the body. The first and second members 12, 12' can then be allowed to move away from each other in a longitudinal manner, splaying the tissue or objects of the body apart by a user removing the force applied to compress the device 10 in its closed state.

In at least one embodiment, the device 10 can include a first member 12 having a distal end and a proximal. The device can further include a second member 12' having a distal end and a proximal. The hinging unit 11 can include at least one leaf-spring element 66 having a first U-shaped member, where the first U-shaped member may have a first end and a second end. The first U-shaped member can be attached to a first side 36a of the first member 12 and a first side 36a' of the second member 12'. The first end of the first U-shaped member may extend from a proximal end of the first member 12 and the second end of the first U-shaped member may extend from the proximal end of the second member 12'. The hinging unit 11 can further include a second U-shaped member, where the second U-shaped member may have a first end and a second end. The second U-shaped member can be attached to the first side 36a of the first member 12 and the first side 36a' of the second member 12'. The first end of the second U-shaped member may extend from the distal end of the first member 12 and the second end of the second U-shaped member may extend from the distal end of the second member 12'. The hinging unit 11 can further include a third U-shaped member, where the third U-shaped member may have a first end and a second end. The third U-shaped member can be attached to a second side 36b of the first member 12 and a second side 36b' of the second member 12'. The first end of the third U-shaped member may extend from the proximal end of the first member 12 and the second end of the third U-shaped member may extend from the proximal end of the second member 12'. The hinging unit 11 can further include a fourth U-shaped member, where the fourth U-shaped member may have a first end and a second end. The fourth U-shaped member may have a first end and a second end. The forth U-shaped member may be attached to the second side 36b of the first member 12 and the second side 36b' of the second member 12'. The first end of the fourth U-shaped member may extend from the distal end of the first member 12 and the second end of the fourth U-shaped member may extend from the distal end of the second member 12. Each of the first, second, third, and fourth U-shaped member can include an apex. The first U-shaped member apex can be coupled to the second U-shaped member apex. The third U-shaped member apex is can be coupled to the fourth U-shaped member apex. The first member 12 can then be moveable relative to the second member 12' so that the first, second, third, and fourth U-shaped members are configured to provide a biasing force to move the first and second members 12, 12' away from each other to position the device 10 in an open state.

Figure 35:
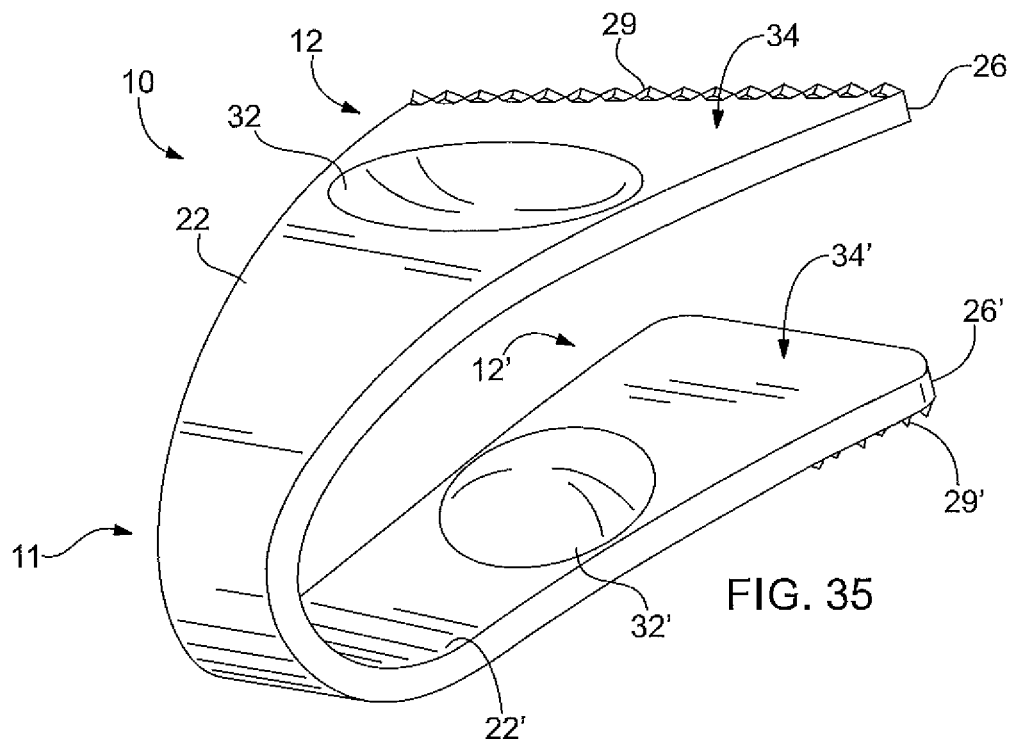
FIGS. 35-36 show perspective views of an exemplary embodiment of the device with a first arm extending from a wedge-shaped first member and a second arm extending from a wedge-shaped second member, where the first arm and the second arm connect at a single junction.
Figure 36:
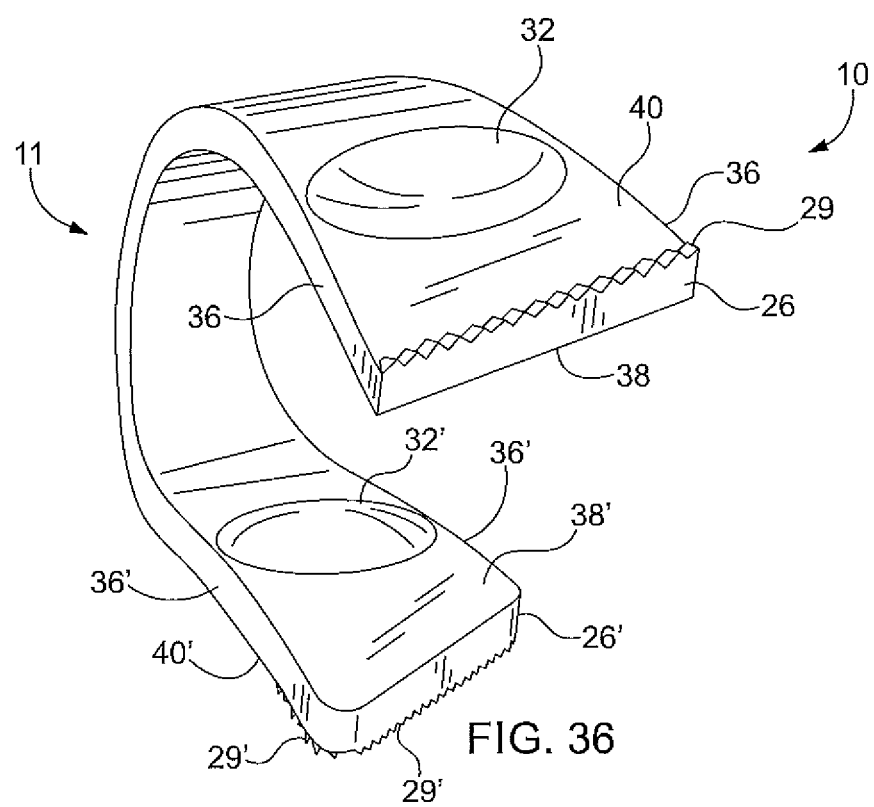
Figure 37:
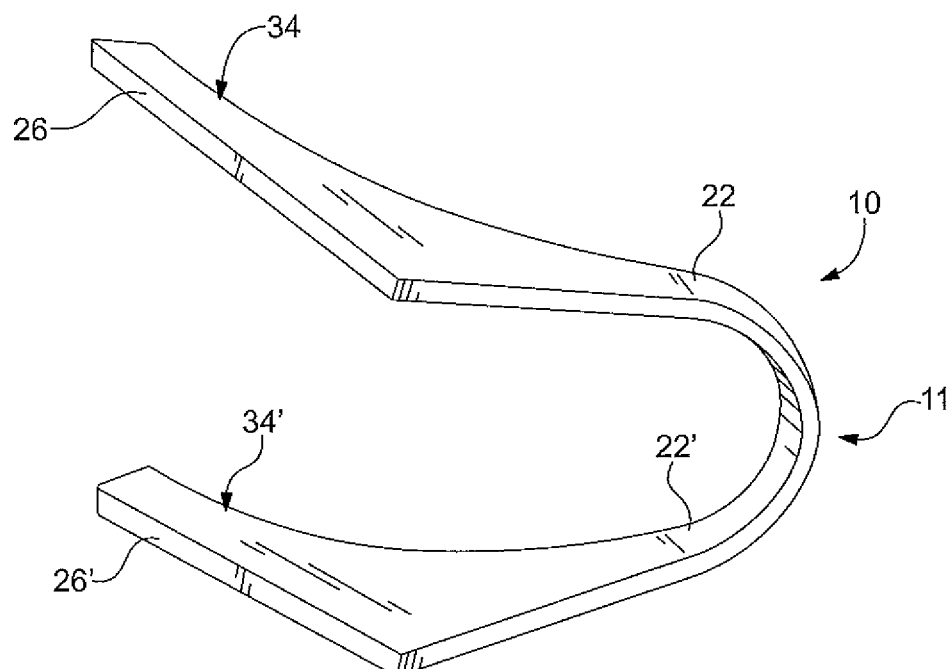
FIGS. 37-38 show perspective views of an exemplary embodiment of the device with each of the first and second members as an elongated element that extends laterally to one side of the device so as to form an L-shape.
Figure 38:
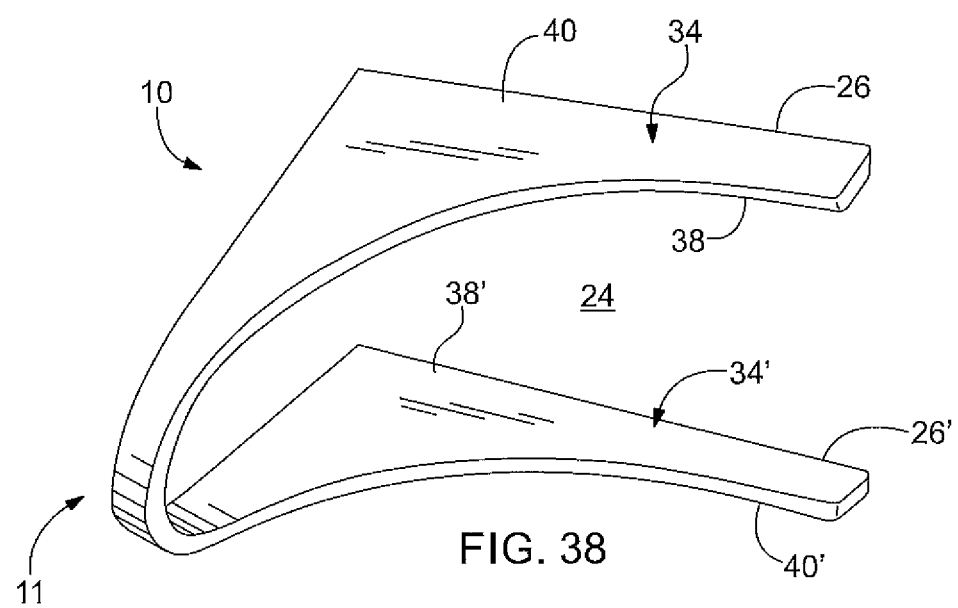
Figure 39:
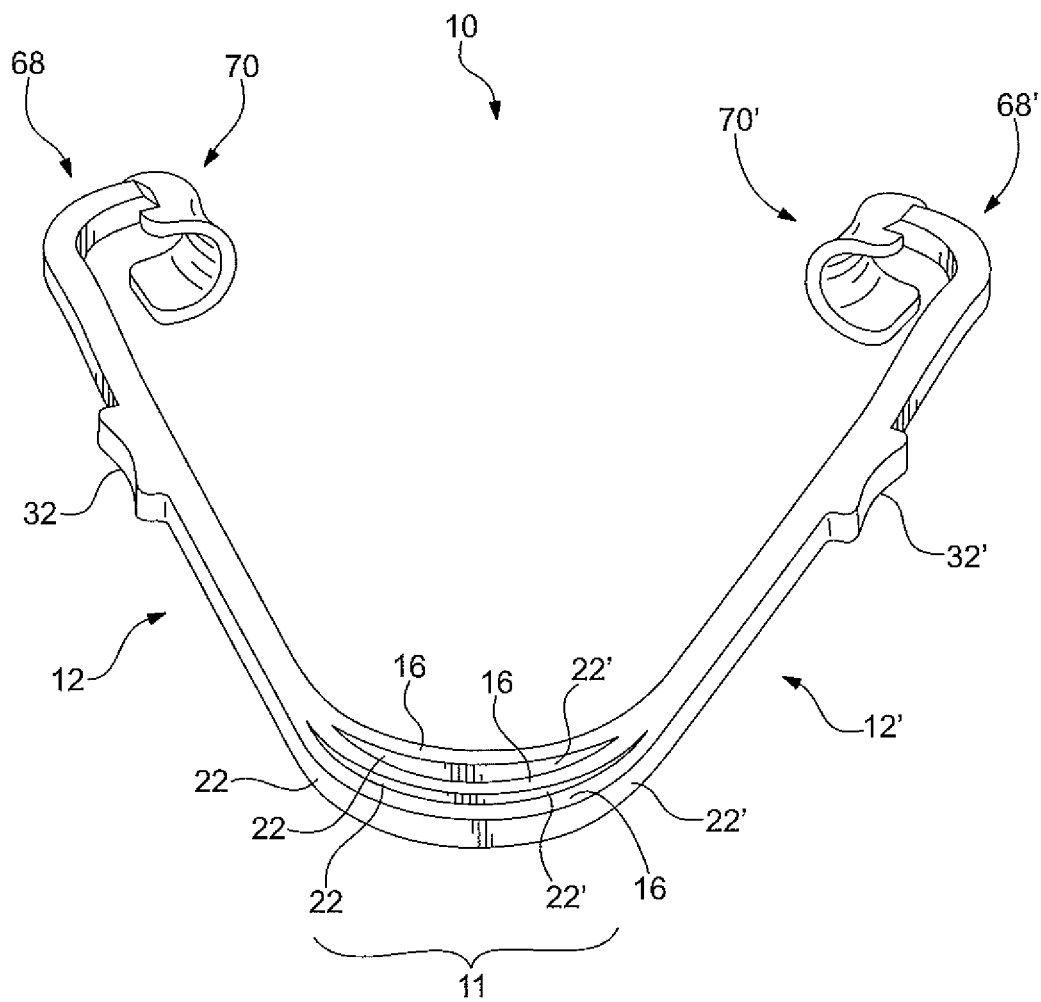
FIGS. 39-44 show perspective views of an exemplary embodiment of the device in which any one or both of the first member and the second member can be structured as a cantilever-type element.
Figure 40:
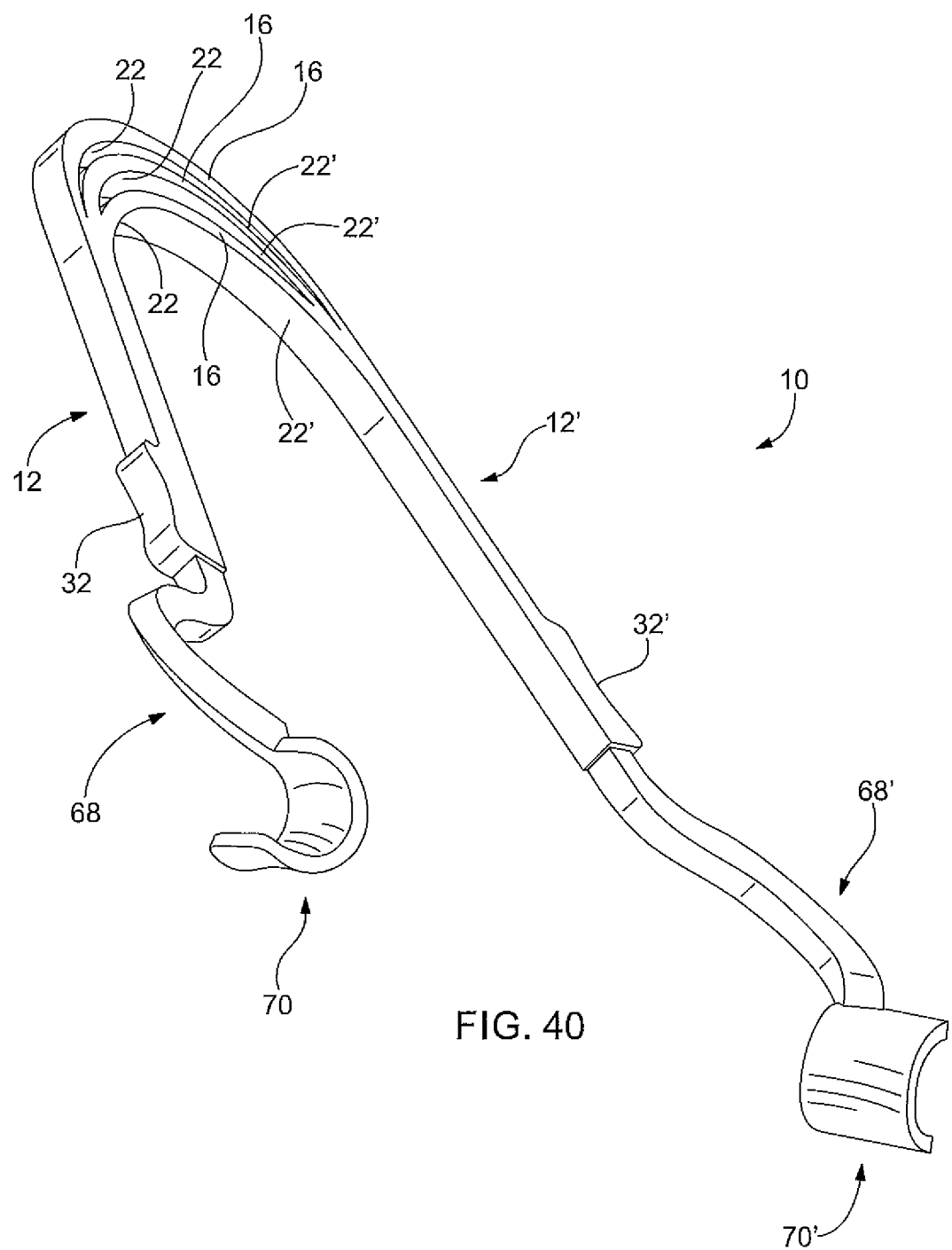
Figure 41:
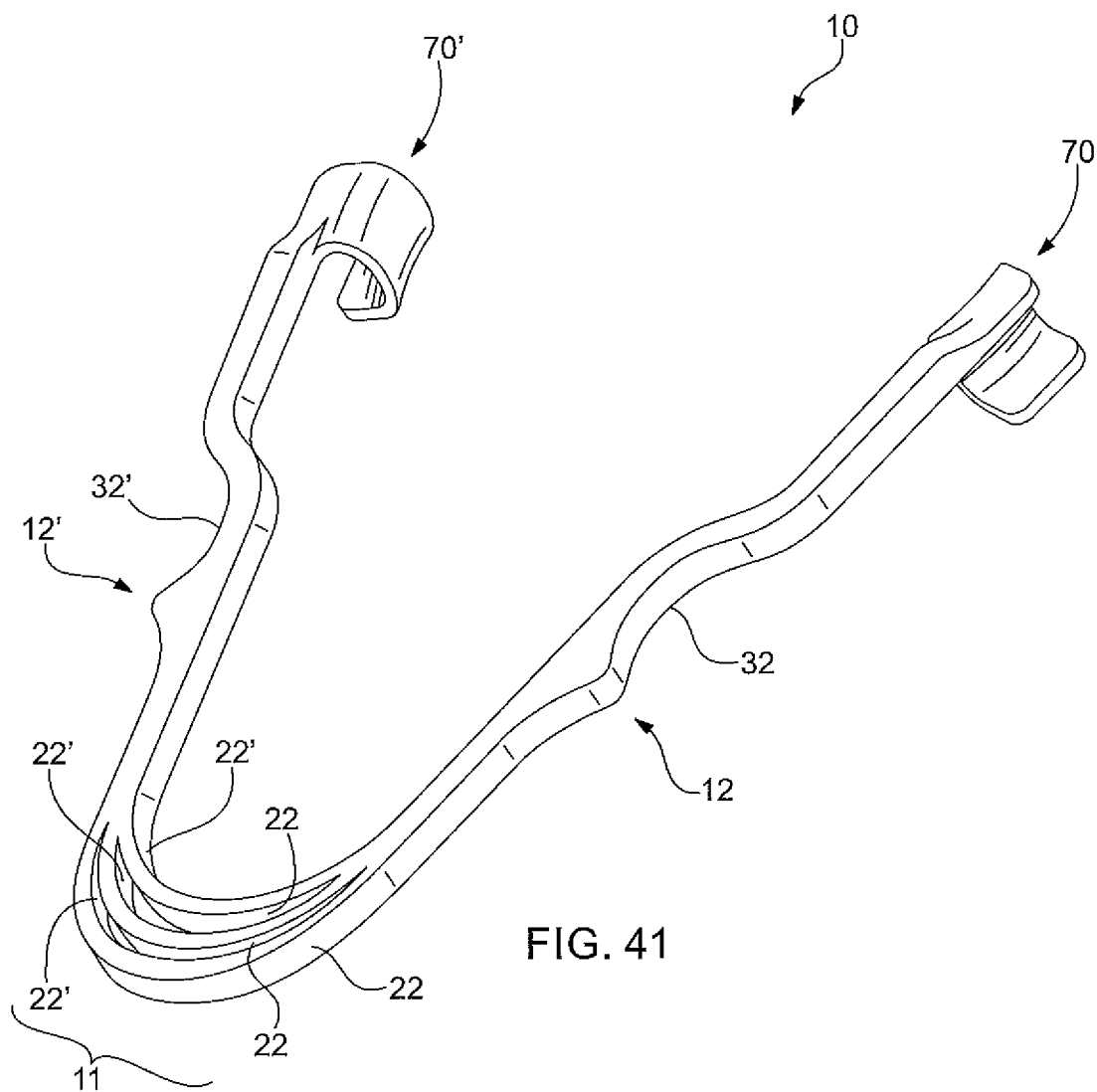
Figure 42:
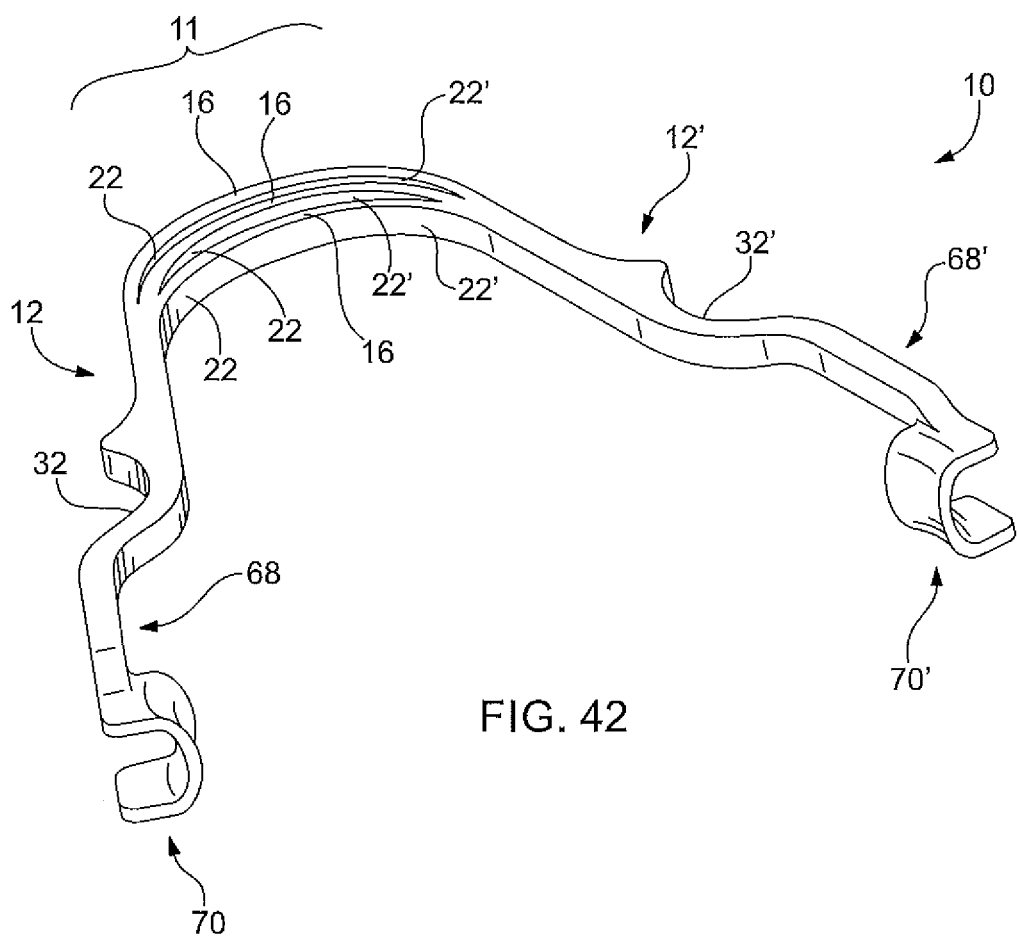

Referring to FIGS. 35-36, the hinging unit 11 can include a first arm 22 extending from a wedge-shaped first member 12 and a second arm 22' extending from a wedge-shaped second member 12', where the first arm 22 and the second arm 22' connect at a single junction 16. The first and second arms 22, 22' can be narrower than the first and second members 12, 12', where the device 10 is most narrow at its junction 16. The device 10 can include a first member plate 34 and a second member plate 34', as described earlier. The device 10 may further include at least one finger retainer 32, 32' formed as a circular depression within at least one of the first member plate 34 and the second member plate 34', as described above. Any portion of the cross beams 26, 26' and/or plates 34, 34' can include a gripping structure 29, 29', as described above. Further, any one of the cross-beams 26, 26' can exhibit different angles. For example, FIG. 36 shows cross beam 26 being substantially perpendicular with the first and second side sections 36a-b of the first member 12, whereas cross beam 26' is at an offset angle with respect to the first and second side sections 36a'-b' of the second member 12'. Further, at least one of the first and second members 12, 12' can exhibit various other shapes. For example, FIGS. 37-38 show each of the first and second members 12, 14 as an elongated element that extends laterally to one side of the device 10 so as to form an L-shape.

In at least one embodiment, the device 10 can include a first member 12 having a proximal end and a distal end. The first member 12 can further have a first member arm 22 extending from the first member proximal end. The device 10 can further include a second member 12' having a proximal end and a distal end. The second member 12' can have a second member arm 22' extending from the second member proximal end. A distal end of the first member arm 22 may be connected to a distal end of the second member arm 22' at a junction 16. At least one of the first member 12 and the second member 12' may include teeth formed on a surface thereof for contacting tissue. At least one of the first member 12 and the second member 12' can further include at least one recess 32, 32' or receiving at least one finger.

Figure 43:
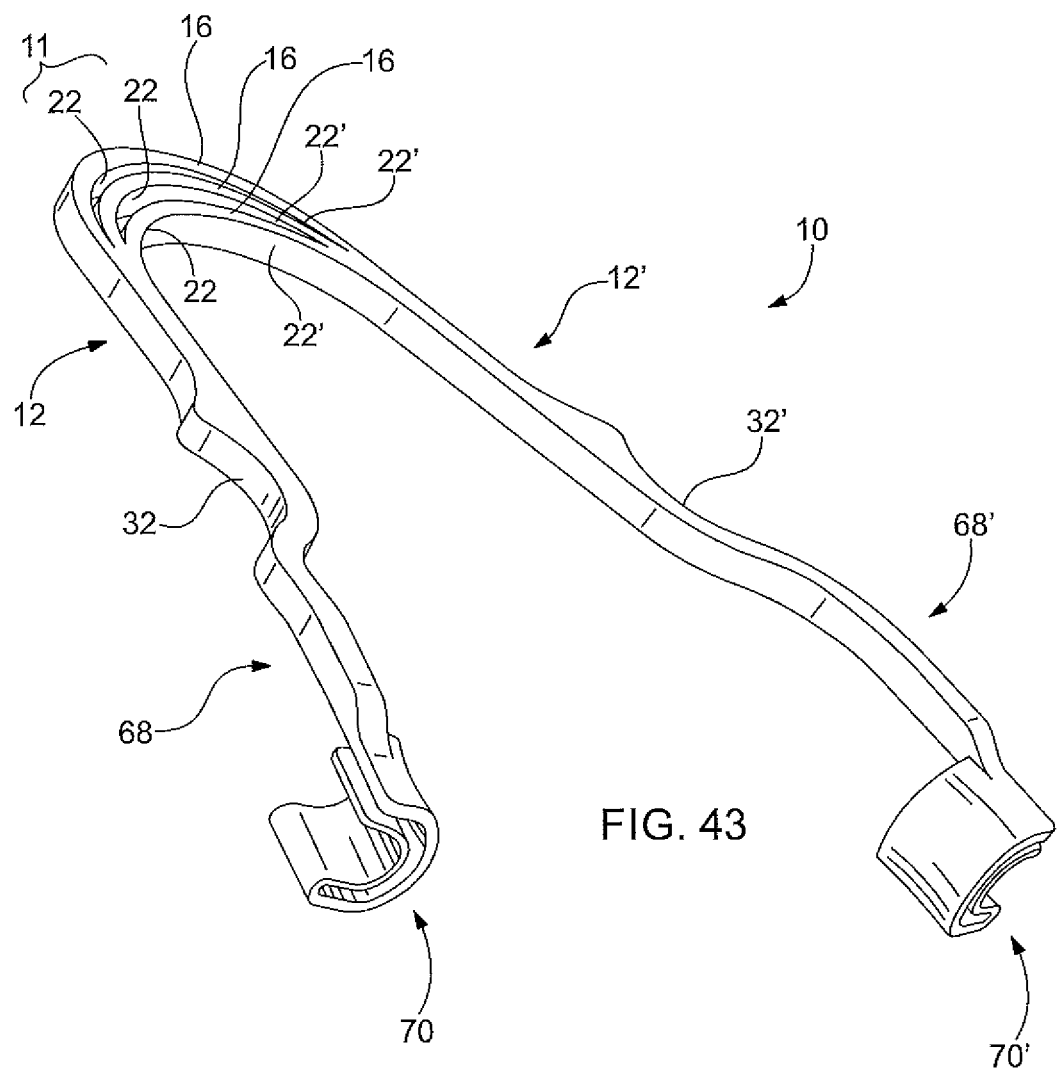
Figure 44:
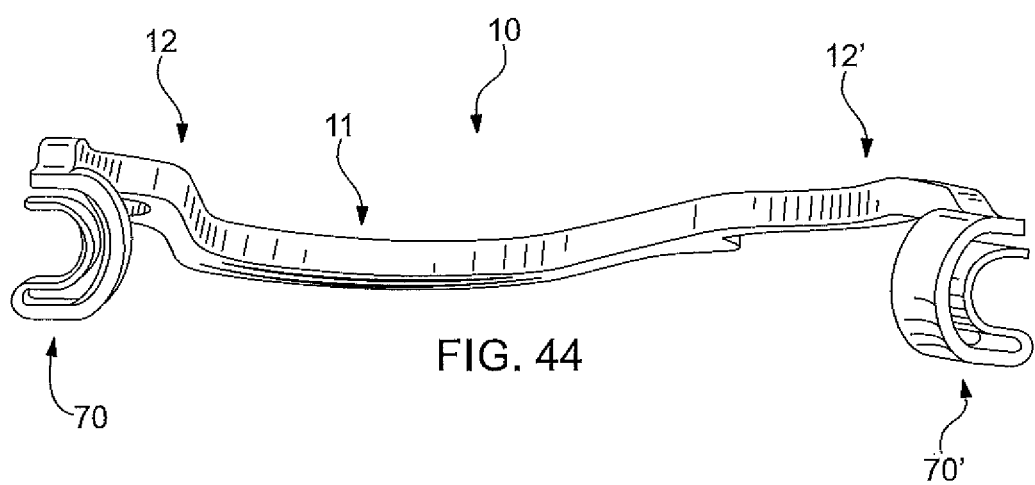

Referring to FIGS. 39-44, the device 10 can include any one of the first member 12 and second member 12' structured as a cantilever-type element. For example, the first member 12 can be a cantilever-type element extending from an arm 22 of the first member 12, which leads to a junction 16. Similarly, the second member 12' can be a cantilever-type element extending from an arm 22' of the second member 12', which leads to a junction 16. The overall structure of the device 10 can be a V-shape with the vertex of the V forming the junction 16 or hinging unit 11. In further embodiments, the junction(s) 16 can form a hinging unit 11, as described above. In some embodiments, the hinging unit 11 can include a plurality of first and second arms 22, 22', as described above. The first member 12 can further include a distal end 68 that is straight, J-shaped, S-shaped, etc. Similarly, the second member 12' can include a distal end 68' that is straight, J-shaped, S-shaped, etc. In addition, the first member 12 and/or the second member 12' can include a C-shaped clamp 70, 70' extending from its distal end 68, 68'. The C-shaped clamp 70 of the first member 12 can be facing inward (toward the second member 12'), outward (away from the second member 12'), or facing any other direction. Similarly, the C-shaped clamp 70, of the second member 12' can be facing inward (toward the first member 12), outward (away from the first member 12), or facing any other direction. The C-shaped clamp(s) 70, 70' can be used to secure a portion of the body (bone, ligament, vein, artery, muscle, etc.) therein. This configuration of the device 10 may be particularly useful when performing neck surgeries. For example, the device 10 can be transitioned into the closed state, wherein the scalene muscle may be secured within the C-shaped clamp 70 of the first member 12 and the levator scapulae muscle may be secured within the C-shaped clamp 70' of the second member 12'. The device 10 can then be allowed to transition toward the open state to splay the two muscles apart. Further, the device 10 can include at least one finger retainer 32, 32' formed on at least one arm 22, 22'. The finger retainer 32, 32' can be a protrusion extending from an arm 22, 22' a rectangular protrusion extending from an arm 22, 22' with a concave top surface, a curvilinear formation formed into an arm 22, 22'. For example, a user can place a thumb on a finger retainer 32' of the arm 22' of the second member 12' and a finger on a finger retainer 32 of the arm 22 of the first member 12 to transition the device 10 to and from the closed state and open state, as well as maneuver the device 10 into and out of position within the neck or other portion of the body. As shown in FIGS. 43-44, some embodiments can include a double-walled C-shaped clamp 70, 70'.

In at least one embodiment, a first member 12 can have at least one arm 22 having a proximal end and a distal end. The first member 12 can include an elongated structure with a C-shaped clamp 70 at its distal end. The at least one arm 22 may extend from the proximal end of first member 12 to its the distal end at which it may be attached or affixed to a distal end of at least one arm 22' extending form a second member 12'. The second member 12' can include an elongated structure with a C-shaped clamp 70' at its distal end. The at least one arm 22' may extend from the proximal end of the second member 12' to its distal end. The proximal end of the at least one arm 22 of the first member 12 can be connected to the proximal end of the at least one arm 22' of the second member 12' via at least one junction 16. The at least one junction 16 may facilitate at least one of statically, resiliently, and pivotally connecting the first and second members 12, 12' so that the first member 12 can be moveable relative to the second member 12' about the at least one junction 16. The first and second members 12, 12' may be moveable toward each other into a closed state and also be movable away from each other via motion about the at least one junction via a biasing force to an open state. The at least one junction 16 may be configured to provide the biasing force to move the first and second members 12, 12' away from each other to position the device 10 in its open state. In some embodiments, the at least one arm 22 extending from the first member 12 can include a first arm, a second arm, and a third arm. Each of these arms may extend from the first member. The at least one arm 22' extending from the second member 12' can include a first arm, a second arm, and a third arm. The first arm 22' extending from the second member 12' can be attached to the first arm 22 extending from the first member such that the arms are joined at their distal ends to form a first junction 16. The second arm 22 may extend from the first member 12 and the second arm 12 may extend from the second member 12' to join to each other at their distal ends to form a second junction 16. The third arm 22 can extend from the first member 12 to its distal end, which can be joined to the distal end of third arm 22 extending from the second member 12' at a third junction 16. The first junction 16 may be being physically separated from the second junction and may be physically separated from the first junction 16 and the second junction may be physically separated from the first junction 16. The distal ends of the first arms 22 and 22' can be spaced apart from the distal ends of the second arms 22 and 22 at the first and second junctions 16 and the distal ends of the second arms can be spaced apart from the distal ends of the third arms at the third junction 16 such that the second arms 22 and 22' and second junction 16 are located between the first and third junctions 16 and first and third arms 22, 22'. The first member 12 and second member 12' can be moveable about the junctions 16 between open and closed positions. The C-shaped clamps attached to those members can be moveable away from each other as the first and second members 12, 12' are moved away from each other to the open position. When moved to the closed position, the C-shaped clamps can be moved closer to each other at the same time the first and second members are moved toward each other as the device is moved from its open state to its closed state.

Figure 45:
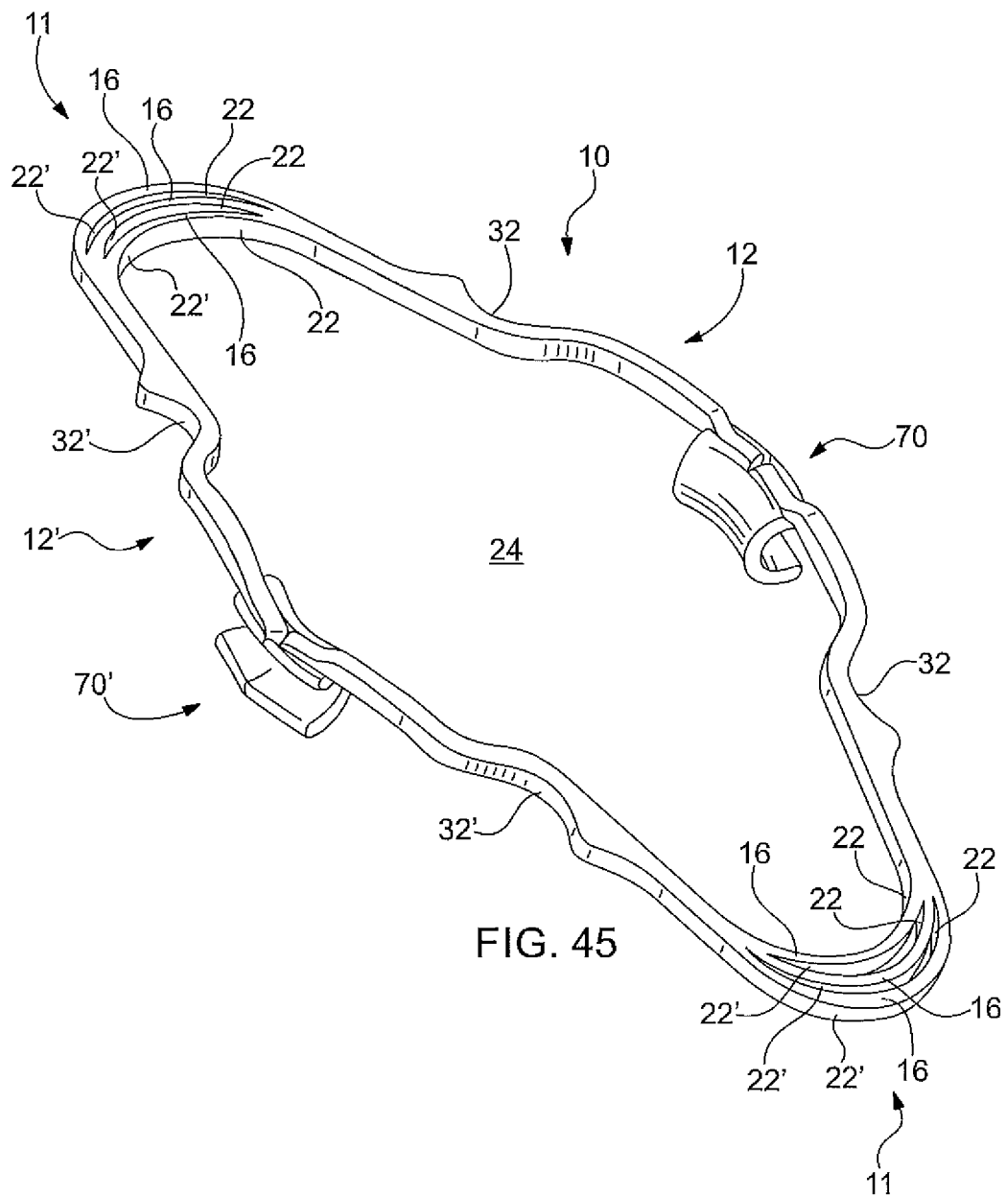
FIG. 45-47 show perspective view of an exemplary embodiment of the device in which any one or both of the first member and the second member can be structured as a cantilever-type element and each member includes arms extending from distal ends thereof to form an annular structure defining a central opening.
Figure 46:
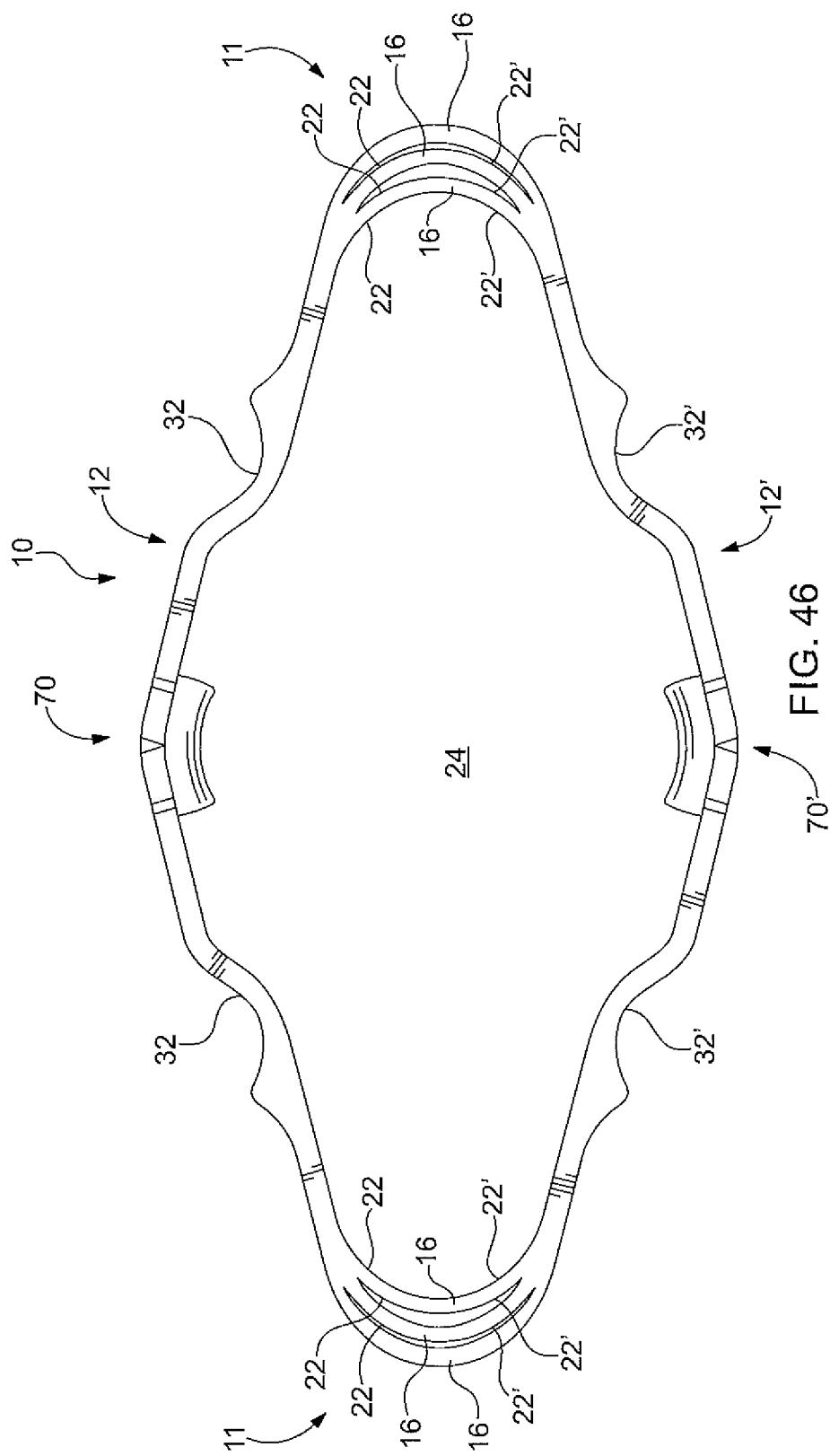
Figure 47:
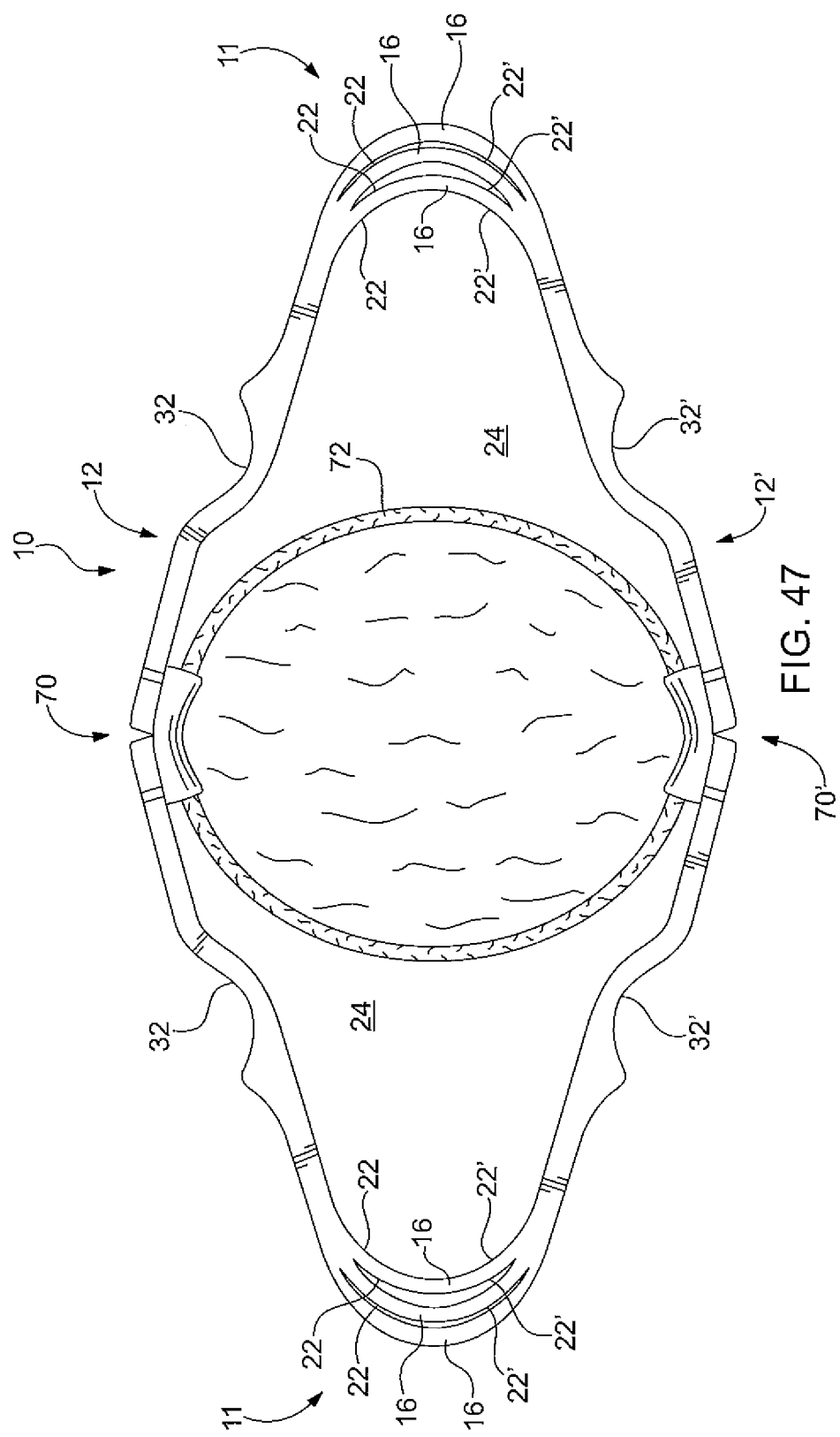

Referring to FIGS. 45-47, device 10 can include hinging units at both ends or sides of the retracting portion of the device. Such a distribution of hinging units can allow for a symmetrical retraction about an incision, for example, an, an abdominal surgery for a pediatric patient where a traditional, stainless steel instrument would be too powerful, too heavy and too cumbersome for a surgeon to use.

Referring to FIG. 47, the device 10, as shown in FIGS. 45 and 46, can utilize a sealing element that seals the opening in the tissue from the outside world. For instance, such a sealing element can be used in a laparoscopic manner where insufflation of the inner space is needed for visualization and surgical access. The device 10 may include a flexible or soft element at or near the proximal aspect that, when deployed as a balloon or compliant ring, would place outward tension circumferentially at the edges of the skin incision and having a membrane or means of bridging the incision opening the thus creating a seal between the surgical space inside of the patient and the environment outside of the patient. The surgical space may then be filled with pressurized gas or fluid to assist in retraction and exposure. The membrane or seal may have perforations or openings to allow passage and manipulation of other elements of the device or to allow introduction of other surgical instruments via the opening 24 defined by the device 10 and the opening defined by the sealing element held or retained by the device 10.

The device 10 can include a first member 12 and a second member 12', where each may be structured as a cantilever-type element composed of a resilient material such as a polymeric material or an elastomeric material formed via molding or 3D printing. Each member 12, 12' may include a C-shaped clamp 70, 70' formed thereon or attached thereto. In some embodiments, the first member 12 can be a cantilever-type element having a C-shaped clamp 70 formed into or disposed onto a portion of the first member 12 between first and second ends of the member. The C-shaped clamp 70 may be at a central portion of the first member 12 or at an intermediate portion between the first and second ends. At least one finger retainer 32 can be formed or defined adjacent the first end and at least one finger retainer 32 can be formed or defined adjacent the second end of the first member 12. For example, the first member 12 can include a cantilever-type element having a first end and a second end with a first finger retainer 32 located at or near the first end, a second finger retainer 32 located at or near the second end, and a C-shaped clamp 70 located between the first and second finger retainers 32. Similarly, the second member 12' can be a cantilever-type element having a C-shaped clamp 70' formed into or disposed onto a portion of the second member 12'. The C-shaped clamp 70' may be at a central portion of the second member 12'. The cantilever-type element of the second member 12' can include at least one finger retainer 32' at or adjacent its first end and at least one finger retainer 32' at or near its second end. The second member 12' can be formed to mirror the shape and size of the first member to provide a symmetric device or may have a different configuration. In some embodiments, the second member 12' can be formed via molding or 3D printing at the same time as the first member 12 as the device 10 is formed as a single unitary structure via the molding or 3D printing. The second member 12' can include a cantilever-type element with a first finger retainer 32' located at or near the first end, a second finger retainer 32' located at or near the second end, and a C-shaped clamp 70' located between the first and second finger retainers 32'. The first end of the first member 12 can be connected to the first end of the second member 12' via a first resilient and/or flexible hinging unit 11. The second end of the first member 12 can be connected to the second end of the second member 12' via a second resilient and/or flexible hinging unit 11.

The first end of the first member 12 can be connected to the first end of the second member 12' via the first hinging unit 11, and the second end of the first member 12 can be connected to the second end of the second member 12' via the second hinging unit 11 so that the device 10 may form an annular structure defining a central opening 24. The area of the opening 24 can increase from a first size when in the device is compressed into its closed state to a second size that is larger than the first size when the device 10 is enlarged into the open state. The hinging units 11 can be configured to bias the device into its open state so that the device requires a force from a user to be applied to compress the device into its closed state. For example, the first and second members 12, 12' may be moveable toward each other into a closed state and also be movable away from each other via motion about the first and second hinging units 11 due to the biasing force provided via the hinging units 11 (e.g. resilient property of the composition of the material of the hinging units 11 and structure of the hinging units, etc.) causing a transition from a closed state to an open state.

The first hinging unit 11 can include at least one arm 22 extending from the first side of the first member 12 that connects with at least one arm 22' extending from the first side or first end of the second member 22'. A second hinging unit 11 can include at least one arm 22 extending from the second side or second end of the first member 12 that connects with at least one arm 22' extending from the second side or second end of the second member 22'. The at least one arm 22 extending from the first side or first end of the first member 12 can connect with the at least one arm 22' extending from the first side or first end of the second member 22' at a junction 16, which may be a portion of the first hinging unit 11. The at least one arm 22 extending from the second side or second end of the first member 12 can connect with the at least one arm 22' extending from the second side or second end of the second member 22' at a junction 16, which may be a portion of the second hinging unit 11.

The at least one arm 22 extending from the first side of the first member 12 can be configured to include a first arm, a second arm, and a third arm, where the first arm can be adjacent the second arm, and the second arm can be adjacent the third arm such that the second arm is between the first and third arms. The at least one arm 22' extending from the first side of the second member 12' can include a first arm, a second arm, and a third arm, where the first arm can be adjacent the second arm and the second arm can be adjacent the third arm such that the second arm is between the first and third arms. The first arm 22 can connect with the first arm 22' at a first junction 16. The second arm 22 can connect with the second arm 22' at a second junction 16. The third arm 22 can connect with the third arm 22' at a third junction 16. The second junction can be between the first and third junctions and be spaced apart from those junctions by gaps. The gaps may be the same size or the gap between the first and second junctions may differ in size from the gap between the second and third junctions. These gaps can be defined to have a particular type of shape to help provide a desired amount of biasing force. The shapes can be arcuate in shape, curved in shape or have another type of shape configured to help facilitate a desired level of biasing force for the first hinging unit.

The at least one arm 22 extending from the second side or second end of the first member 12 can include a fourth arm, a fifth arm, and a sixth arm, where the fourth arm can be adjacent the fifth arm, and the fifth arm can be adjacent the sixth arm such that the fifth arm is between the fourth and sixth arms. The at least one arm 22' extending from the second side of the second member 12 can include a fourth arm, a fifth arm, and a sixth arm, where the fourth arm can be adjacent the fifth arm and the fifth arm can be adjacent the sixth arm such that the fifth arm is between the fourth and sixth arms. The fourth arm 22 can connect with the fourth arm 22' at a fourth junction 16. The fifth arm 22 can connect with the fifth arm 22' at a fifth junction 16. The sixth arm 22 can connect with the sixth arm 22' at a sixth junction 16. The fifth junction can be between the fourth and sixth junctions and be spaced apart from those junctions by gaps. The gaps may be the same size or the gap between the fourth and fifth junctions may differ in size from the gap between the fifth and sixth junctions. The fifth junction can be positioned in alignment with the second junction, the fourth junction may be positioned to be in alignment with the first junction and the sixth junction may be positioned in alignment with the third junction. These gaps can be defined to have a particular type of shape to help provide a desired amount of biasing force. The shapes can be arcuate in shape, curved in shape or have another type of shape configured to help facilitate a desired level of biasing force for the first hinging unit.

The first and fourth junctions may correspond to each other on opposite sides or ends of the device, the fifth and second junctions may correspond to each other on opposite sides or ends of the device 10 and the third and sixth junctions may correspond to each other on opposite sides or ends of the device 10. For instance, the shape and size and alignment of the gap between the first and second junctions may mirror the shape and size and alignment of the gap between the fourth and fifth junctions. The shape and size and alignment of the gap between the third and second junctions may mirror the shape and size and alignment of the gap between the sixth and fifth junctions.

The device 10 of FIGS. 45-47 and 56 may be used to hold a seal 72 in place or be used in conjunction with a seal 72 at a site of an incision. For example, the seal 72 can be retained within at least one C-shaped clamp 70, 70, as shown in FIG. 47. The seal 72 can be a torus shaped member or annular shaped member (e.g. an O-ring or other type of annular gasket or annular shaped seal member or an inflatable seal such as an annular shaped balloon that may be enlarged via an air flow or fluid flow) that can be held in place so that the seal 72 is held within the opening 24 of the device 10. The seal 72 can be composed of a resilient or flexible material so that the seal may flex, stretch or bend to other sizes via motion of the device 10 between its closed and open states.

Figure 56:
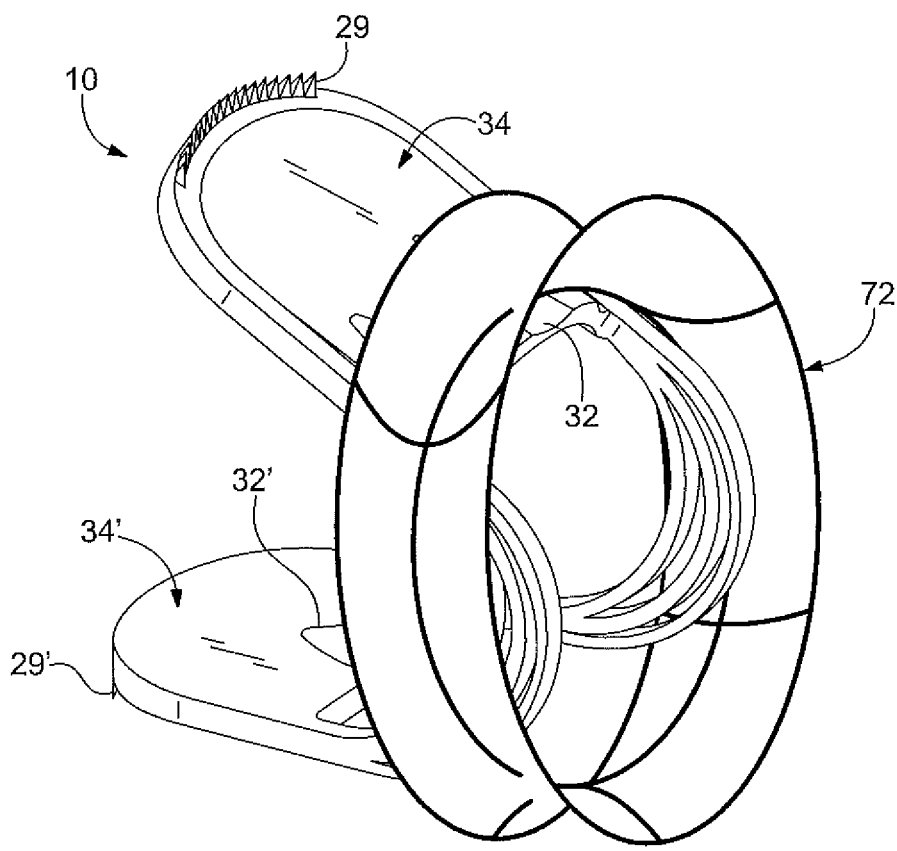
FIG. 56 is a perspective view of an exemplary embodiment of the device used in conjunction with a seal and a membrane positioned inside the seal.

In addition to the seal, a membrane can be utilized as shown in FIG. 56. The membrane can be positioned between the seal 72 and the device 10. The membrane may provide a means of bridging an incision opening to create a seal between the surgical space inside of a patient and the environment outside of the patient. The surgical space can be filled with pressurized gas or other fluid to assist in retraction and exposure of the tissues within the surgical space. The membrane or seal may define perforations or openings to allow passage and manipulation of elements of the device 10 or to allow for the introduction of surgical instruments.

The device 10 can be configured to releaseably retain or hold the seal 72 in a same, or substantially same, geometric plane defined by the members 12, 12' and/or arms 22, 22' of the device 10. For instance, the C-shaped clamps 70, 70' can be out of said geometric plane so that the seal 72 can be held out of said geometric plane but still parallel with, or substantially parallel with, said geometric plane. In use, the device 10 can provide traction and counter-traction for an incision, and further generate a seal by holding the seal such that the seal is in contact with and/or engagement with the tissue along an outer or inner perimeter of the seal 72. For example, the seal can be secured in place via the C-shaped clamps 70, 70', as shown in FIG. 47 for retaining a portion of a body to seal a particular site of an incision made within a tissue pocket or within a leading dissection edge via the seal surrounding the body part (e.g. intestine, organ, artery, vein, etc.) adjacent or within an incision site adjacent that the device is helping to prop open by providing continuous traction and counter traction to splayed apart tissue layers (e.g. skin and underlying tissue adjacent the body part being sealed via the seal 72). The seal can also be configured to be inflated or otherwise manipulated to be brought into engagement with tissue to seal a periphery of an incision site while the seal is attached or held by the device 10.

During a surgical procedure, the device 10 can be forced into a closed state by moving the first member 12 towards the second member 12' to compress the device 10. The compression of the device 10 into its closed state can result in the device having an elongated oval-type shape as compared to when the device is in the open state, which may be less elongated and have a more ring or circular type shape. An incision can be made to cut back a first tissue and expose a second tissue that is underlying the first tissue. The device 10 can then be placed onto or into the incision in its closed state. After insertion, the surgeon can allow the biasing force of the device to automatically transition the device from its closed state to the open state, thereby helping to further expose the second tissue and provide continuous traction and counter-traction as the device 10 moves toward its open state and further dissection or other surgical work is performed. The seal 72 can be attached to the device 10 prior to the device 10 being inserted into an incision of tissue pocket or may be attached to the device 10 after it is inserted into the incision or tissue pocket and after that device has moved from its closed state to a position between its closed state and open state (e.g. at an intermediate state or at its fully open state). The seal 72 and/or device 10 can be manipulated within an incision or tissue pocket during the surgical procedure to have the seal 72 contact tissue or a portion of a body within a tissue pocket or incision to seal a cut, dissection, or other type of aperture or incision formed in a body part being worked on during a surgical procedure. It is contemplated that the device 10 of this configuration may be beneficial for surgical procedures where it is desired for the first tissue to be retracted in a radial manner. This can include abdominal surgery, for example.

In some embodiments, the distal end portions of the first, second, and third arms that define the first, second, and third junctions 16 can be arcuate in shape or curved to help facilitate a biasing force the resiliently biases the first and second members 12, 12' away from each other toward the open position of the device 10. The arms and members and other elements of the device 10 can be composed of a translucent material or an opaque material that is resilient such as a polymeric or elastomeric material.

In further embodiments, the device 10 can include a retractor adjustment mechanism (not shown) to adjust the biasing force exhibited by the device 10. For example, a rigid or semi-rigid sleeve can be slidingly disposed over the hinging unit 11. The sleeve can be configured to slide over the junction 16 portion(s) and further onto the any of the arms 22, 22'. The sleeve can adjust the magnitude of the biasing force as it is slid over the junction(s) 16 of the hinging unit 11. For example, if the device 10 may exhibit a greater biasing force when the sleeve is slid directly over the junction(s) 16 as opposed to being slid over the an arm 22, 22'. Other retractor adjustment means can be used. For example, a tensioning mechanism can be provided to adjust the spring rate of a spring within the pivoting mechanism 20. In some embodiments, it may be desired to use a substantially constant restoring force (biasing force) throughout the working range (i.e., from the closed state to the open state or propped state) of the device 10. Thus, an adjustment can be made to ensure that a constant biasing force is exhibited as the device 10 transitions to and from the closed state and open state or propped state.

In some embodiments, the device 10 can include a coupling to couple one device 10 to another device 10 so as to use at least two devices 10 in tandem. For example, a first device 10 can include a snap-fit configuration on a lateral side (e.g., on at least one of the first and second side sections 36a-b, 36a'-b' of the first member 12 and/or second member 12') to allow snapping one device 10 together with another device 10. Other coupling means can include an aperture to enable coupling of at least two devices 10 via a pin (e.g., a cotter pin for example). Further embodiments can include elements for stabilization (e.g., brackets clamps, clip, suture, staples, screws, wires), a surface element container feature that provides fixation, an automatically extending articulated element, a feature that changes along with deployment or removal (e.g., extends with expansion and retracts with compression), blades that spread laterally to form a spherical shape, slots or openings to allow more visualization, a light-source to help visualize (e.g., similar to a speculum or vaginal light), a video camera or Charged Coupled Device (CCD), an inflatable annulus on an end of the device 10, suction holes to which suction is provided in order to help hold the device in place, irrigation, etc.

By adding the suction passages (holes), as an integral part of the device 10, the size efficiency of the retractor may be optimized, as a separate suction device may no longer be required for electrocautery smoke and excess fluid removal. For example, connection of a vacuum source to the vacuum conduct 62 can facilitate withdrawal of debris (e.g., smoke, excess fluid, etc.) via the suction passages and the vacuum conduit 62 and into the vacuum source. The succession passages can be formed within any portion of the device 10 and can be in fluid communication with the vacuum conduit 62.

The device 10 can further include a power source in electrical connection with an illumination source. For example, the device 10 may include an LED illumination source with a replaceable and/or rechargeable battery connected to an electrical switch. This can assist a surgeon in view the area of operation, which can include viewing the area within the incision. The material composition of the entirety of the device or at least portions of the device can be also be configured to facilitate illumination. For instance, the device can have portions or be entirely configured so that the device is non-reflective so that light that may be emitted through the device or by the device is not reflected back toward a surgeon to distract the surgeon or form a glare that may impede surgical work. The reflectivity of the device 10 can be configured so that it can be effectively focused on a particular region of interest. Alternatively, portions or an entirety of the device can be configured to be reflective to provide a general brightness to a particular region within or by the device 10. In some embodiments, it is contemplated that interior surfaces of the device may be configured to be non-reflective and the exterior portions may be reflective or vice versa to facilitate desired illumination objectives. In yet other embodiments, the entirety of the device 10 can be composed of a material that is non-reflective so that a light passed by the device is able to be finely focused as desired by a surgeon without having the device detract from the illumination objectives for application of the light. The reflectiveness and/or non-reflectiveness of different portions of the device can be defined by coatings, textures, material composition, and color of those sections or portions of the device.

The retractor can create an airtight or watertight seal on an incision (for a laparoscopic approach). For instance, tissue contacting surfaces of the device can be configured to form an airtight seal and/or watertight seal on tissue to which those surfaces contact when placed into an incision or tissue pocket. In some embodiments, one or more conduits can be defined in the first and second members 12, 12' or other portions of the device to provide a vacuum for providing such a seal. In other embodiments, the composition of the device and/or adhesives of the device or applied on the device may help facilitate such a seal.

In addition, the device 10 and/or any of the kits can include built-in or added tissue retraction services. These can include, but are not limited to, other components to assist with clamping and/or detraction of additional areas of localized tissue that may be needed during specific surgeries. Additionally, other soft tissue components may be included to assist with additional fixation and/or elevation during the course of the procedure. These can include small add-on clamps that interface with the device 10 for example. The device 10 can be further loaded into a delivery apparatus to facilitate the device's 10 insertion and removal. For example, the device 10 can be compressed into a smaller initial form and mounted onto a delivery apparatus such as a long handle or other gripping apparatus, for example, to facilitate the introduction of the device 10 through a surgical portal that is smaller than the expanded (device 10 in a non-closed state) device 10. Other embodiments may include a handle, or gripping device, that could facilitate/extend the surgeon's reach.

Figure 48:
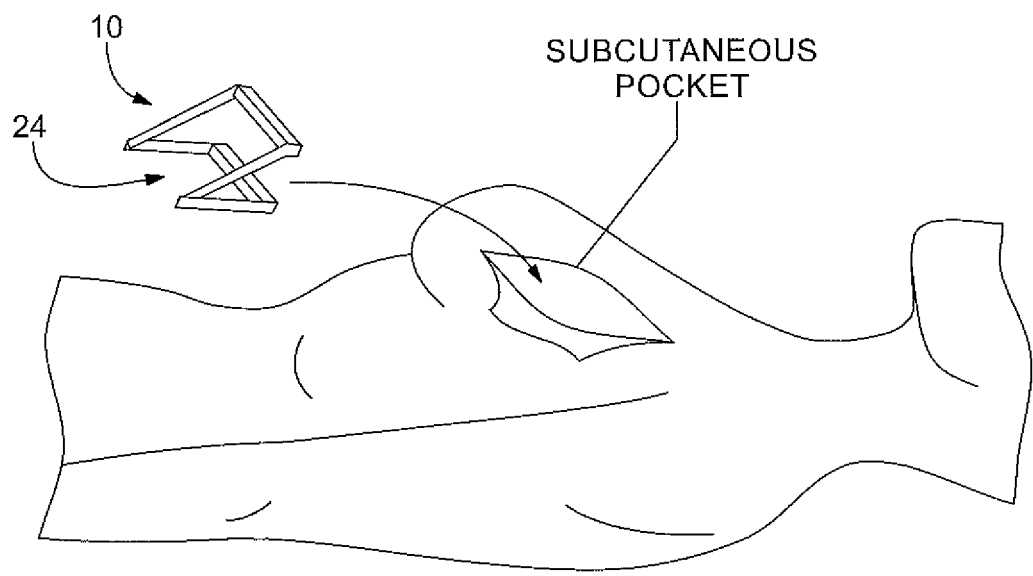
FIG. 48 illustrates an exemplary incision forming a subcutaneous pocket for a surgery, in which at least one embodiment of the device may be inserted.
Figure 49A:
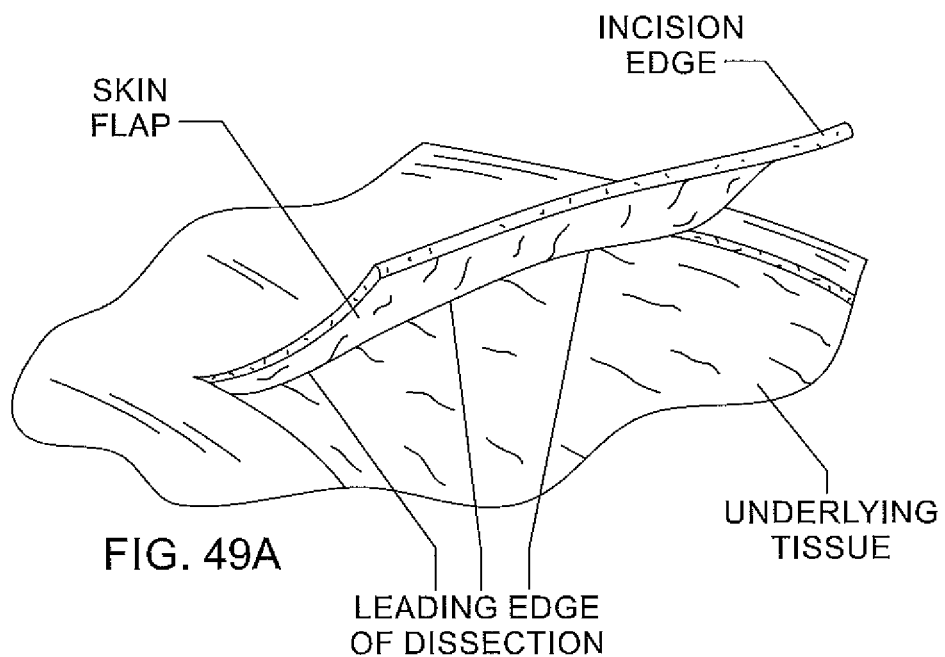
FIG. 49A is a fragmented view of a subcutaneous pocket, showing the leading dissection edge of the subcutaneous pocket formed via a skin flap.
Figure 49B:
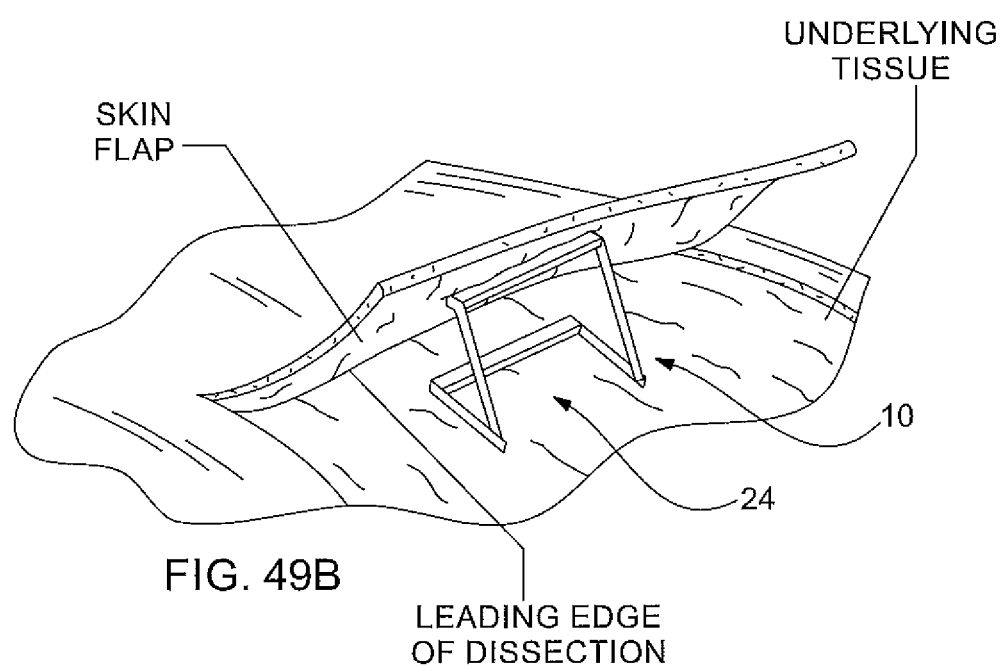
FIG. 49B is a view similar to FIG. 49A illustrating an embodiment of the device positioned within the subcutaneous pocket.

Referring now to FIGS. 48-49B, embodiments of the device 10 may be used for retraction by applying traction and counter-traction to the skin and underlying tissue when placed there-between. The device 10 may be collapsed into a low profile (e.g., closed state or closed position) by forcing the first and second members 12, 12' towards each other, thereby resiliently displacing the first and members 12, 12' and/or compressing the spring to enable insertion into the subcutaneous pocket (i.e., under the skin flap) through a small incision. The low profile of the closed state can obviate creating an incision larger than what may be necessary, further enabling a surgeon to create incisions optimal for cosmesis. Collapsing the device 10 into a closed state can also prevent inadvertent tearing or other injury to skin and/or tissue at the incision and/or operating site. Once positioned between the skin and underlying tissue, the biasing force from the resiliency and/or spring may cause the first and second members 12, 12' to attempt to displace into an open state or a propped state. Where the skin can be dissected, the skin may be retracted from the underlying tissue below the skin and propped up and away from the underlying tissue. Where the skin has yet to be dissected, the biasing force can provide traction and counter-traction so that when the skin/tissue interface has been sufficiently disbanded, the device 10 may retract the skin from the tissue to complete the dissection.

The device 10 can be configured so that the first member 12 and the second member 12' may be displaceable/deflectable within a range from approximately 0° degrees (e.g., when the first and second members 12, 12' abut each other) to approximately 180° degrees (e.g., when the first and second members 12, 12' lie in the same plane and subtend each other) relative to each other and with respect to the pivot axle at the junctions 16. The range of motion may be limited by the mechanical stops, for example. As another example, the closed state may occur when the relative displacement is approximately 0° degrees and the open state is approximately 45° degrees. As yet another example, the closed state may occur when the relative displacement is approximately 0° degrees and the propped state is approximately 60° degrees. One skilled in the art will appreciate, with the benefit of the present disclosure, that the closed state may be any minimal displacement/deflection angle dictated by the mechanical stop and the open or propped state may be any angle greater than the minimal displacement/deflection angle. Generally, the closed state is formed by acting upon the first and second members 12, 12' to collapse the device 10 to position the first and second members 12, 12' against each other, and the open or propped state is formed by allowing the device 10 to exhibit its wedge-like shape to position the first and second members 12, 12' at a distance away from each other.

The open and the closed states of the device 10 can enable placement of the device 10 within close proximity to the dissection plane so that retraction causes traction and counter-traction at the dissection plane. However, the device 10 may be placed anywhere within the subcutaneous pocket, even in close proximity to the incision edge, so that the biasing force props the skin flap up and into a salutary position conducive for conducting surgical procedures within the area of operation. Traction, counter-traction, and propping provided by the device 10 can enable medical professionals to perform surgical operations with assurance that the skin flap can be retracted and suspended away from the underlying tissue without overstretching, overextending, inadvertent slippage or release, and/or bruising, tearing, or other injury to the skin and/or tissue. Furthermore, hands-free traction, counter-traction, and propping by the device 10 may free up valuable time and resources (e.g., medical professional staff/skills can be better allocated for more technical and value added duties) in the operating room, in addition to avoiding un-ergonomic methods of manual splaying the skin/tissue.

Figure 50A:
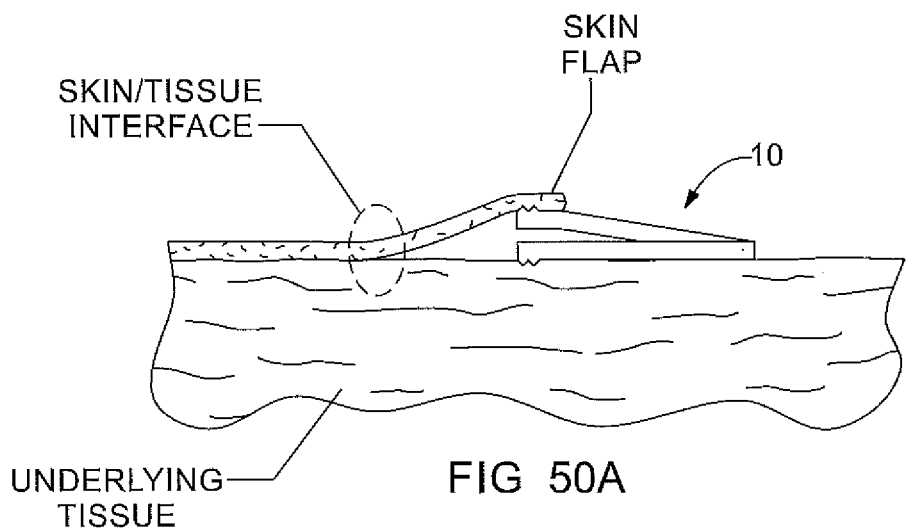
FIG. 50A depicts an embodiment of the device seated within a subcutaneous pocket with the cross-beams positioned adjacent the leading dissection edge for the generation of traction and counter-traction and for separation of the skin flap as an incision in the body is made.
Figure 50B:
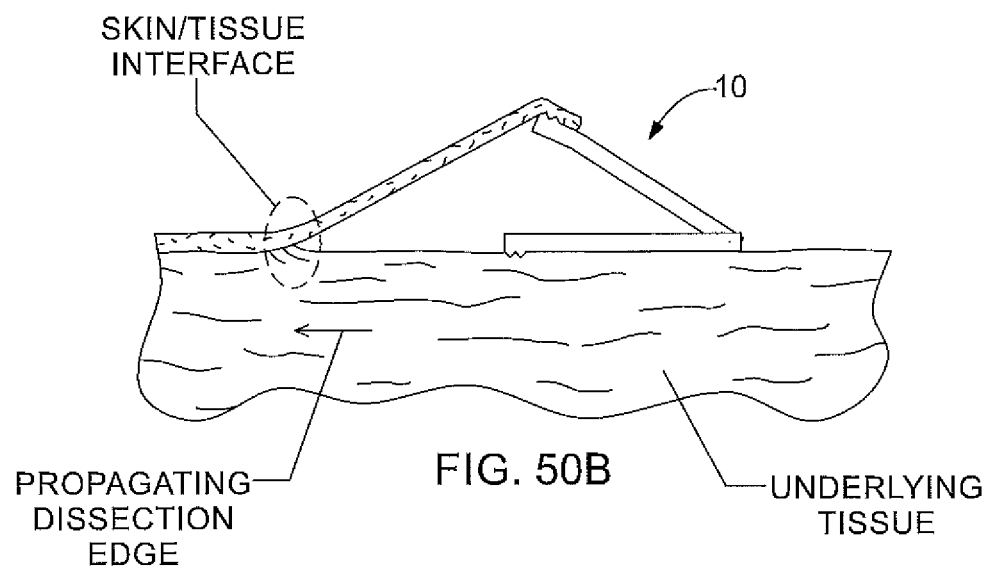
FIG. 50B depicts an embodiment of the device in FIG. 50A transitioning further into a propped state or further opened state as the dissection edge is propagated due to dissection procedures.

Referring now to FIGS. 50A and 50B, in use, the device 10 may be collapsed into a closed state and inserted through the incision such that the cross-beams 26, 26' or other distal ends of the first and second members 12, 12'spearhead the introduction of the device 10 into the subcutaneous pocket. Once inside the subcutaneous pocket, cross-beams 26, 26' or other distal end potions of the first and second members 12, 12' may be positioned adjacent the leading dissection edge (e.g., the point at which the skin is still attached to the underlying tissue). As dissection occurs (e.g., via electro-cautery, a scalpel, or other dissection technique), the biasing force of the deflected first and second members 12, 12' and/or spring may cause continuous traction and counter-traction at the leading dissection edge so that retraction of the skin from the tissue can be achieved via the biasing force of the device 10. Because the device 10 provides continuous traction and counter-traction, the skin can be continuously retracted as dissection separates the two layers along a patient's body, thereby "propagating" the dissection edge along the desired dissection path. As propagation of the dissection path ensues, the device can continue to transition from its closed state to its propped state, thereby propping the skin flap up and away from the tissue to generate a salutary operating cavity within which medical professionals can see and operate. As dissection occurs, the device 10 may be repositioned, removed, or additional devices 10 may be introduced at spaced apart locations to assist the medical professional with retraction and propping of the skin flap as the surgical operation continues.

Once in position within the subcutaneous pocket, the opening 24 may enable a surgeon to conduct dissection procedures while the device 10 is in place without impeding access to the leading edge of dissection. In other words, the opening 24 not only affords a surgeon a vantage view of the leading dissection edge, but it can also provide ingress/egress of tools and fingers via the inlet 24a and the mouth 24b being in communication with the intermediate structure of the opening 24 so that surgery can be performed unabated. The opening 24 and non-conductive nature of the material comprising the device 10 may also ensure that the device 10 does not cause operational interference with electrocautery or other dissection techniques. Furthermore, continuous retraction and propping of the skin as dissection occurs can prevent the skin flap from falling back toward the tissue and inadvertently suffering thermal injury or other injury from the dissection operation.

Figure 50C:
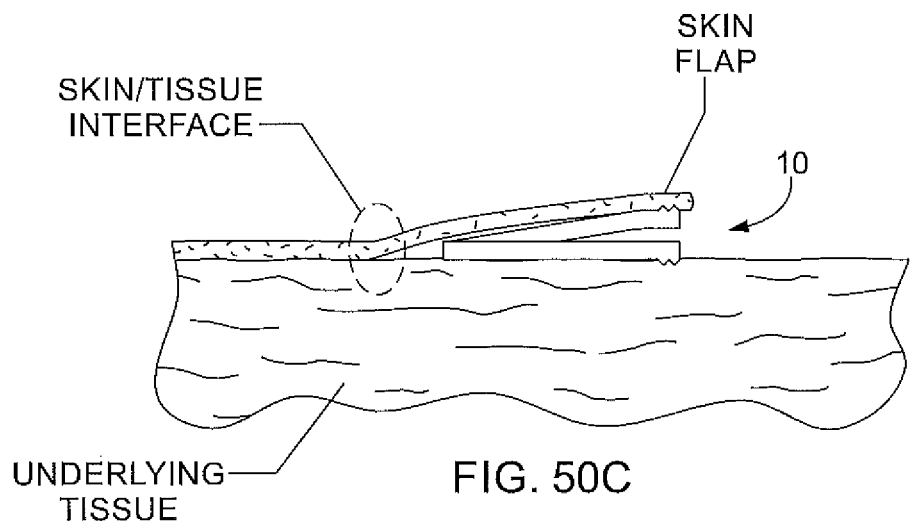
FIG. 50C depicts an embodiment of the device seated within a subcutaneous pocket with the resilient junctions or resilient hinge portions positioned adjacent the leading dissection edge for generation of traction and counter-traction for separation of the skin flap as an incision in the body is made.
Figure 50D:
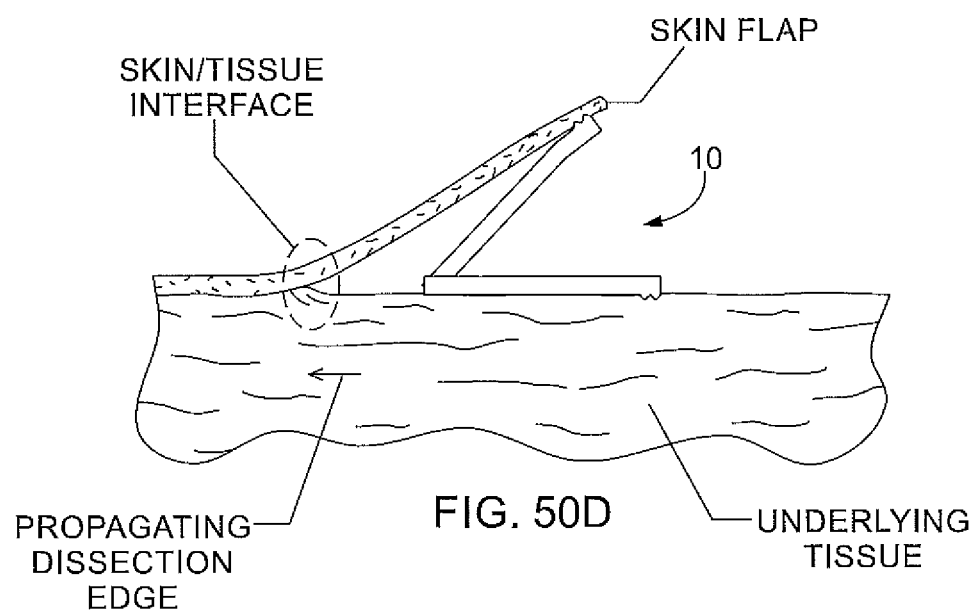
FIG. 50D depicts an embodiment of the device in FIG. 50C transitioning into a further propped state or further opened state as the dissection edge is propagated due to dissection procedures.

Referring now to FIGS. 50C and 50D, while using the device 10 may include positioning the device 10 such that the cross-beams 26, 26' are adjacent the leading edge of dissection, they need not be. For instance, the device 10 need not be inserted such that the cross-beams 26, 26' or other distal end portions opposite the junctions 16 spearhead the introduction through the incision. Rather, the device 10 may be inserted, orientated, and positioned in any manner that assists with traction, counter-traction, and/or propping of the skin flap. For example, the junctions 16 may be positioned to be adjacent to the leading edge of dissection. The device 10 may be collapsed into a closed state and inserted through the incision such that the hinging unit 11 or junction(s) 16 spearheads the introduction of the device 16 into the subcutaneous pocket. Once inside the subcutaneous pocket, junctions 16 may be positioned adjacent the leading dissection edge, and as dissection occurs, the biasing force of the deflected first and second members 12, 12' and/or spring may cause continuous traction and counter-traction at the leading dissection edge so that retraction of the skin from the tissue can be achieved via the biasing force of the device 10.

Furthermore, the device 10 need not be inserted fully within the subcutaneous pocket. For example, the cross-beams 26, 26' may be inserted to retract the skin and/or tissue while the hinging unit 11 or junctions 16 protrude from the incision and extend outside of the body. Placement of the device 10 fully or partially within the subcutaneous pocket may depend on the type of the body part surgery is being perform on or the shape and size of the skin flap. It is further contemplated to use the device without having to create a subcutaneous pocket. For instance, the device 10 can be used to splay the eyelids open, splay finger apart, etc. during surgery or during any other medical procedure.

It is contemplated for a single device 10 to be used for a surgical procedure, and for the device 10 to be repositioned, depending on the area of tension, while the surgical procedure is carried out. However, multiple devices 10 may be used during a surgical procedure. For instance, a first device 10 may be used to provide traction and counter-traction at the leading edge of dissection while a second device 10 may be used to prop the skin flap at a different location, such as at the incision edge for example. As another example, multiple devices 10 may be used to provide traction and counter-traction along a large dissection edge and/or multiple dissection edges.

For example, a method of retracting a first tissue from a second tissue can include creating an incision separating the first tissue from the second tissue to expose at least one of the first and second tissues and to form a tissue pocket. A first device 10 can then be collapsed to a closed state, afterwards inserting at least a portion of the first device 10 when in the closed state through the incision to position the first device 10 adjacent a leading dissection edge. The user can then allow a biasing force of the first device 10 to prop the first tissue up and away from the second tissue and apply traction and counter-traction after the first device 10 is inserted into the incision. A user may then further dissect the first tissue from the second tissue at the leading dissection edge along a dissection path after the first device 10 is positioned into the tissue pocket adjacent the leading dissection edge such that the first device 10 moves toward an open state via the biasing force during the further dissecting to apply traction and counter traction as the further dissecting is performed along the dissection path. A user may then collapse a second device 10 into a closed state to insert at least a portion of it when in the closed state into a tissue pocket formed adjacent the incision. A user can then allow a biasing force of the second device 10 to prop the first tissue up and away from the second tissue and apply traction and counter-traction after the second device 10 is inserted into the tissue pocket. A user may then collapse a third device 10 into a closed state to insert at least a portion of it when in the closed state into a tissue pocket formed adjacent the incision and/or other portion of the incision. A user can then allow a biasing force of the third device 10 to prop the first tissue up and away from the second tissue and apply traction and counter-traction after the third device 10 is inserted into the tissue pocket or incision.

Figure 55:
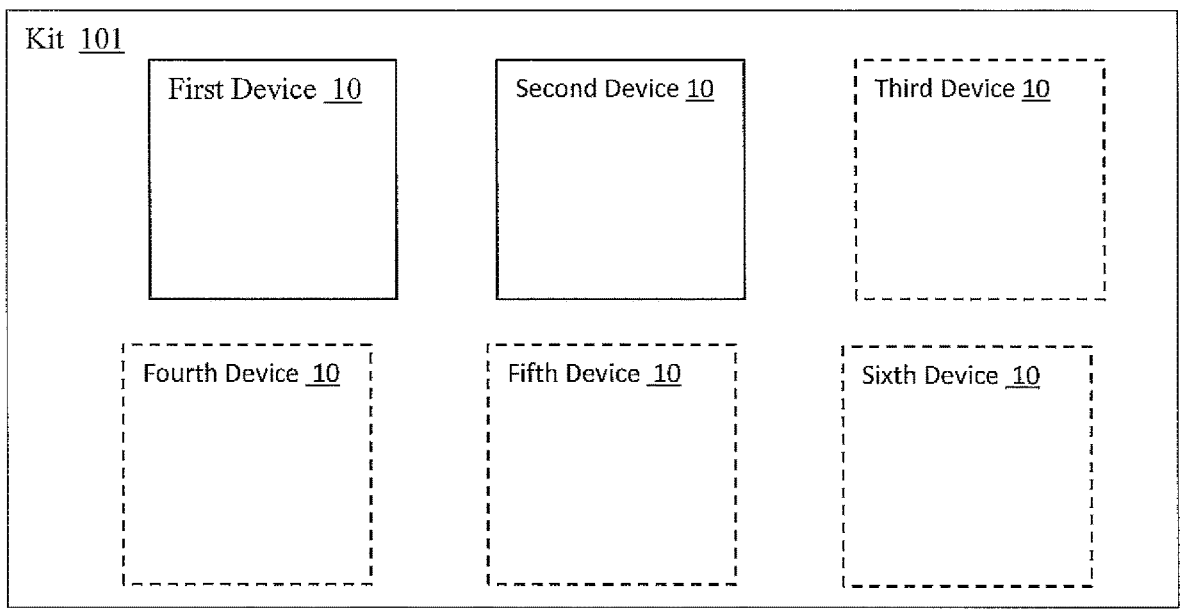
FIG. 55 is a block diagram illustrating an exemplary embodiment of a kit of devices that can be utilized in one or more types of surgical procedures. Each of the devices of the kit may have different indicia to indicate different properties and/or uses of the devices. Each of the devices of the kit may also, or alternatively, have different structures.

As may be appreciated from FIG. 55, the first device 10 and the second device 10 may be components of a kit 101. The configuration of the first device may be a configuration of any device 10 disclosed herein or illustrated herein. The configuration of the second device 10 can be the same as the first device 10 or may be a different configuration of any device 10 disclosed or illustrated herein for use in a surgical procedure in which the first device may also be used. The kit can also include third, fourth, fifth, and/or sixth devices (shown in broken line). The configuration of each of these devices may be a configuration of any device 10 disclosed or illustrated herein. The configurations may be the same as the first device or second device or may differ for use in another aspect of the same surgical procedure the first and second devices 10 may be utilized in The kit 101 can be configured in a number of different arrangements. For instance, the kit can be configured to provide two or more of the same device for use in a surgical procedural to facilitate use of multiples versions of the same device during the procedure or so that backup devices may be available in case a device is soiled or defective. As another example, the kit may include two or more devices that have diverse characteristics (e.g. size, shape, resilience, biasing force, tooth aggressiveness, direction of a biasing force vector, etc.) to allow a surgeon to select the device that is most appropriate for a particular surgery (e.g. incision size, tissue characteristics, etc.) and the size and configuration of a particular patient's body. For instance, a kit can include multiple devices 10 that have different sizes, biasing forces, surface textures, and other properties. As yet another example, a kit can include different sets of different devices. For instance, first and second devices of the kit 101 can be configured as the same device and third and fourth devices of the kit may be configured as different devices and fifth and sixth devices of the kit can be configured as yet other types of devices to provide different functions or uses in a surgical procedure. Some of the devices may provide tenting to hold a dissection path open, while others are configured to help hold an incision site open while yet others are configured to apply retraction at an incision site or provide propping in or adjacent a tissue pocket.

Devices of the kit 101 can include indicia to indicate at least one property of each device. The indicia can indicate at least one property of the first device is different from at least one property of another device within the kit. The indicia could be symbols, letters, numbers a defined set of surface contours defining indicia (e.g. bumps, ridges, brail, etc.) or may be a combination of such indicia. The indicia could include text or symbols to identify a size property, resilience force, element surface grip, or other property. The size ranges could range from very small (VS) to small (S) to medium (M), to large (L) to extra-large (XL). The resilience force could represent a particular range or a number that corresponds to a particular range (e.g. a range of 1-10 can correspond to weak to very strong or a small force to a large force or 1-10 could represent a spectrum for surface grip from smooth to rough, to toothed to aggressively toothed). For instance, indicia could be labeled as A-1-1 for one device in the kit and a second device could be labeled L-10-10 in the kit to identify differing properties of those devices of the kit.

The indicia can be located on the device where it may be easily seen. For instance, the indicia may be located on an inner facing surface of an upper member or an inner facing surface of a lower member so that it is not covered by a user's fingers when the device is in use and may be easily seen or felt by the user.

The indicia can also include color such as color segments or colored label attached to a device to indicate at least one property. The indicia may also be a coloration of an entirety of a device. For instance, the first device 10 may have a first color and the second device 10 may have a second color. The third device 10 of the kit 101 can have a third color. The first color can be different from the second color, and the third color can be different from first color and also different from the second color. The first color may indicate at least one property of the first device. The second color may indicate at least one property of the second device 10. The third color may indicate at least one property of the third device 10. The first, second, and third colors may indicate that one or more properties of the first, second, and third devices 10 differs from each other. For instance, each color may indicate a different biasing force that biases that device to the open position. The first color could indicate a strongest biasing force, the third color could indicate the weakest biasing force, and the second color could indicate an intermediate biasing force. The colors that may be utilized can include any color such as red, orange, yellow, green, blue, violet, black and/or white. There may of course be other colors and other devices within a kit. The colors of each device may be due to a coating applied to the exterior surface of the device or a pigment or coloring agent included in a material that the device is molded from (e.g. a pigment included in polymeric or elastomeric material that is utilized for molding the device via injection molding). Other properties could also be indicated by the different colors (e.g. suitability for a particular type of procedure, suitability for use against particular types of tissue, etc.). The kit 101 may also include other devices such as fourth, fifth, and sixth devices that have the same color as the first device or second device or third device that correspond with those devices having the same configuration as the device of the same color. One or more of these devices in kit 101 may have a different color (e.g. fourth color, fifth color, etc.) and different configuration from these devices that correspond to the at least one property of the color of that device. It is also contemplated that the devices may have different colors to indicate one or more properties of the device and may also include a label having indicia or be formed having the indicia defined thereon to identify other properties of the device.

As another example, a method of retracting a first tissue from a second tissue can include creating an incision separating the first tissue from the second tissue to expose at least one of the first and second tissues and to form a tissue pocket. A first device 10 can then be collapsed to a closed state, afterwards inserting at least a portion of the first device 10 when in the closed state through the incision to position the first device 10 adjacent a leading dissection edge. The user can then allow a biasing force of the first device 10 to prop the first tissue up and away from the second tissue and apply traction and counter-traction after the first device 10 is inserted into the incision. A user may then further dissect the first tissue from the second tissue at the leading dissection edge along a dissection path after the first device 10 is positioned into the tissue pocket adjacent the leading dissection edge such that the first device 10 moves toward an open state via the biasing force during the further dissecting to apply traction and counter traction as the further dissecting is performed along the dissection path. A user may then collapse a second device 10 into a closed state, afterwards inserting at least a portion of the second device 10 into the incision at a location that is spaced apart from the first device 10 when the second device 10 is in the closed state of the second device 10. A user can then allow a biasing force of the second device 10 to prop the first tissue up and away from the second tissue and apply traction and counter-traction after the second device is inserted into the incision. Further dissection along a dissection path may occur as the first and second devices move to their open positions after being inserted into the incision. Of course, additional devices may also be similarly positioned as dissection or other surgical procedure efforts continue to provide continuous traction and counter traction in a similar manner.

Although embodiments of the device 10 may obviate manual retraction, it does not preclude it. The opening 24 may enable insertion of fingers there-through for manual retraction via splaying the skin/tissue if the situation dictates. Furthermore, medical professionals may splay the first and second members 12, 12' of the device 10 without having to breach the opening 24 plane and/or without making contact with the skin/tissue. Moreover, the ease with which the device 10 may be repositionable and removable may enable manual retraction of the skin/tissue without having to insert fingers through the opening 24 and/or splay the first and second members 12, 12'. In other words, a medical professional may employ manual retraction techniques at one portion of the subcutaneous pocket while the device 10 is used to prop the skin flap up at another portion of the subcutaneous pocket.

Figure 51A:
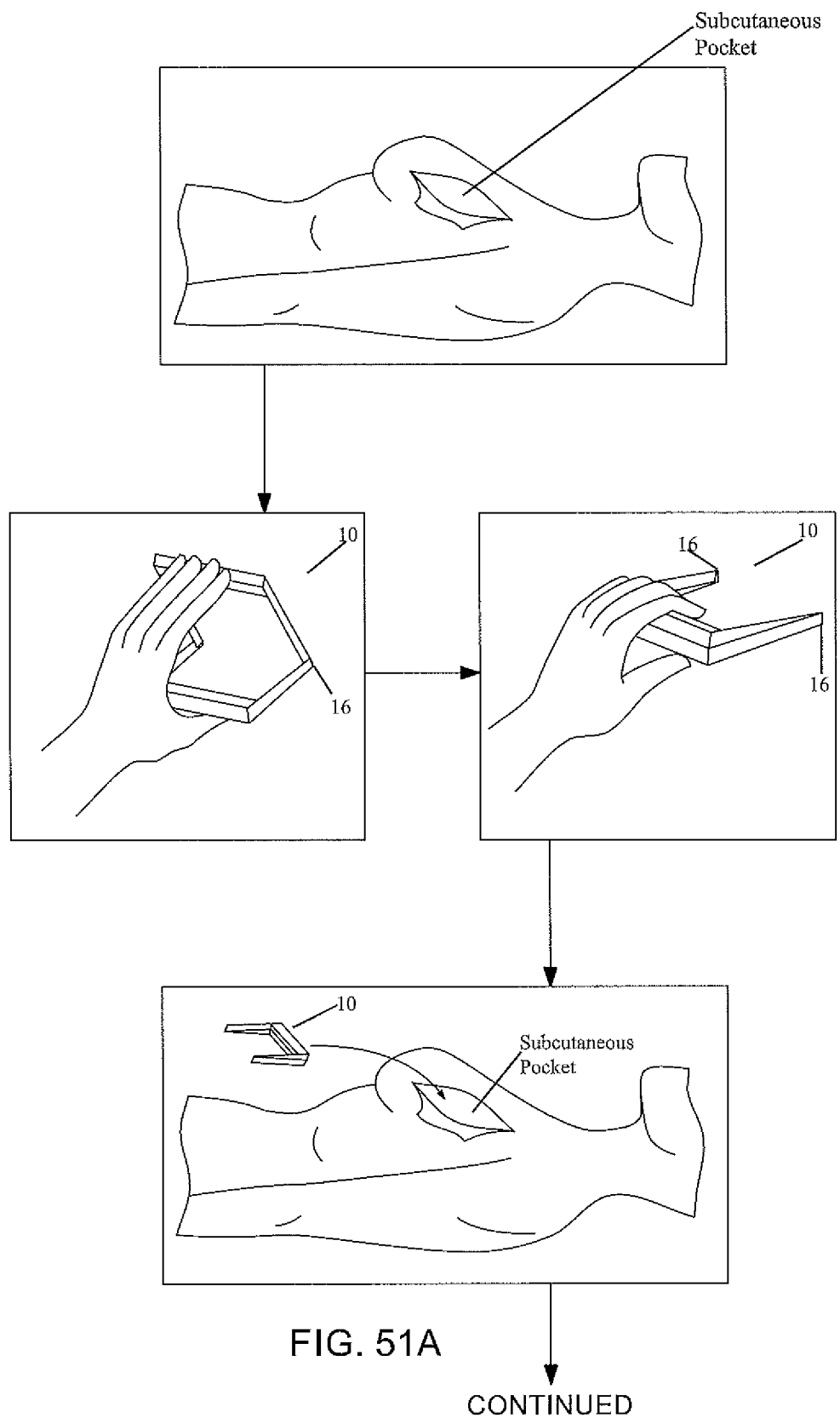
FIGS. 51A-51B illustrate an exemplary method of using an embodiment of the device.
Figure 51B:
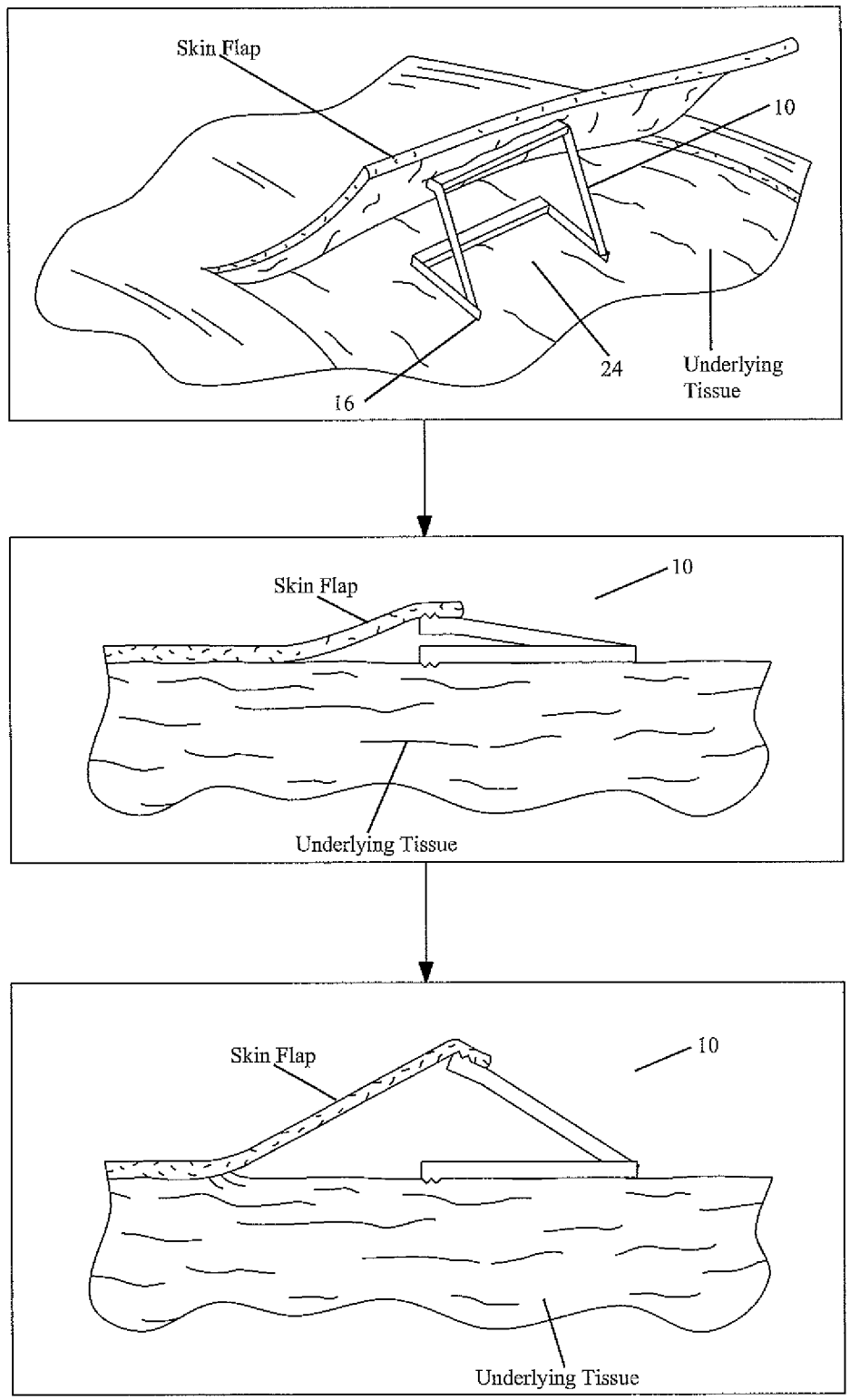

Referring now to FIGS. 51A-51B, an exemplary method of using the device is illustrated. As can be seen from FIGS. 451A-51B, embodiments of the device 10 may be employed by creating an incision in skin of a body to expose underlying tissue. A subcutaneous pocket may be created within a skin flap/tissue interface, where the incision defines the subcutaneous pocket and at least a portion of the skin flap/tissue interface is a leading dissection edge. The device 10 may then be grasped and/or collapsed. The device 10 may then be inserted in the closed position through the incision and into the subcutaneous pocket. The device 10 may be positioned to lie adjacent the leading dissection edge. A biasing force of the device 10 can prop the skin up and away from the tissue and apply traction and counter-traction adjacent the leading dissection edge. The skin may be further dissected from the tissue at the leading dissection edge after the device 10 is positioned so that the device 10 can provide continuous traction and counter-traction at the leading dissection edge as the leading dissection edge is propagated along a desired dissection path. As the leading dissection edge is further propagated, the device 10 may further prop open to retract and prop the skin flap to support the skin flap in a suspended position.

In further embodiments, it is contemplated that the device 10 can be used during oncological procedures with the device 10 positioned within a formed subcutaneous pocket. Creating the incision may include forming an incision that is sized and positioned for optimal cosmesis. Positioning of the device 10 may include placing the cross-beams 26, 26' adjacent the leading dissection edge. Dissecting the skin from the tissue may include electrocautery or other dissection techniques, and it may further include viewing the leading dissection edge through the opening 24 and performing dissection through the opening 24.

Referring to FIGS. 52 and 53, flow charts describing exemplary methods of using an embodiment of the device 10 are illustrated. Referring to FIG. 52, an incision can be made for a mastectomy procedure or other surgical procedure using a scalpel or other incision instrument. A skin retractor, such as a face lift retractor, can be used to start the dissection plane on the tissue plane directly posterior to the subcutaneous tissue of the mastectomy skin flap. Once the dissection plane is started and carried out to about 7 cm in length and about 4-5 cm in depth, the device 10 may be inserted into the incision. With the device 10 in a closed position, the device 10 can be placed into the operating cavity, allowing it to open after being positioned adjacent the leading dissection edge. The device 10 can be positioned so that the cross-beams 26, 26' retract the mastectomy skin flap anteriorly while simultaneously retracting the breast tissue posteriorly, which may allow for improved visualization of the dissection plane. The dissection can be performed through the opening 24 of the device 10. The device 10 may continue to open as the dissection is carried out until it reaches a point of maximal opening. The device 10 can be reposition to a new location depending on area of tension or a second device 10 may be inserted at this new location. After dissection is performed to the chest wall, the device 10 can be removed. The breast may then be is dissected from the pectoralis muscle. The device 10 can then be used in conjunction with forming an incision for mastectomy of a patient's second breast if a bilateral mastectomy is performed by repeating the steps above.

Referring to FIG. 53, an incision can be made for a surgical procedure using a scalpel or other incision instrument. A skin retractor, such as a face lift retractor, can be used to start the dissection plane on the first tissue plane directly posterior to the first tissue. Once the dissection plane is started and carried out, the device 10 may be inserted into the incision. With the device 10 in a closed position, the device 10 can be placed into the operating cavity, allowing it to open after being positioned adjacent the leading dissection edge. The device 10 can be positioned so that the cross-beams 26, 26' retract the first tissue anteriorly while simultaneously retracting the underlying second tissue posteriorly, which may allow for improved visualization of the dissection plane. The dissection can be performed through the opening 24 of the device 10. The device 10 may continue to open as the dissection is carried out until it reaches a point of maximal opening. In other words, as the further dissection occurs after the device 10 is inserted into the incision, the device 10 may move to the fully open state. This can allow a surgeon to perform the operation with continuity because the device 10 may be configure to continuously open (or transition from the closed state to the open state) as dissection occurs to release the first tissue from the second tissue and lift the first tissue up and away from the second tissue. As the device 10 transitions from the closed state to the open state as further dissection occurs, the device 10 can also prop the first tissue up and away from the second tissue to enable the surgeon to view and access the area of operation. The automatic application of continuous traction and counter traction provided by the device 10 can occur with only the biasing force provided by the device 10 (e.g., the hinging unit 11, junctions 16, etc.). A surgeon's hands can be free for other aspects of the procedure.

The device 10 can be reposition to a new location depending on area of tension or a second device 10 may be inserted at this new location. After dissection is performed to the body, the device 10 can be removed.

It is contemplated that numerous modifications and variations of the described examples and embodiments are possible. For example, the length of the dissection and depth of the dissection disclosed in FIG. 52 can be varied to any suitable depth or length and/or to account for numerous other criteria, such as breast size, body composition, surgical preference, and other factors.

While exemplary embodiments may describe and illustrate the device 10 and methods of use for propping and retracting skin from underlying tissue, one skilled in the art will appreciate, with the benefit of the present disclosure that the device 10 and methods of use can be used for propping and retracting one type of tissue from another type of tissue. For example, the device 10 and methods of use can be used to prop and retract muscle tissue, nerve tissue, epithelial tissue, bone tissue, visceral tissue, organ tissue, glandular tissue, and/or connective tissue from each other. Thus, the device 10 and methods of use can be used to prop and retract a first tissue from a second tissue. The first tissue may include, but is not limited to muscle tissue, nerve tissue, epithelial tissue, bone tissue, visceral tissue, organ tissue, glandular tissue, and/or connective tissue. The second tissue may include, but is not limited to, muscle tissue, nerve tissue, epithelial tissue, bone tissue, visceral tissue, organ tissue, glandular tissue, and/or connective tissue. The second tissue may be the same type of tissue as the first type of tissue or may be a different type of tissue as that of the first type of tissue.

Thus, a method of retracting a first tissue from a second tissue can include creating an incision separating a first tissue from a second tissue to expose at least one of the first and second tissue and to form a tissue pocket. The device 10 can then be collapsing into a closed state. The device 10 can then be inserted through the incision and into the formed tissue pocket to position the device adjacent a leading dissection edge, allowing a biasing force of the device 10 to prop the first tissue up and away from the second tissue and apply traction and counter-traction. Dissecting the first tissue from the second tissue can then be performed at the leading dissection edge along a dissection path after the device is positioned into the tissue pocket adjacent the leading dissection edge. The first tissue may be a different type of tissue than the second type of tissue or the first type of tissue may be the same type of tissue as the second tissue.

Therefore, while certain exemplary embodiments of devices and methods of making and using the same have been discussed and illustrated herein, it is to be distinctly understood that the invention is not limited thereto but may be otherwise variously embodied and practiced within the scope of the following claims.

We claim:

1. A retractor and prop device, comprising:
a first member;
a second member;
wherein:
the first and second members are moveable relative to each other about at least one junction, each junction of the at least one junction is configured to at least one of statically, resiliently, and pivotally connect the first member and the second member together such that the first member is movable relative to the second member via motion about the at least one junction;
each junction of the at least one junction is configured to provide a biasing force to move the first member and the second member away from each other to position the device in an open state; and
the first member is movable relative to the second member about the at least one junction from the open state to a closed state;
a first arm, a second arm, and a third arm extending from adjacent a first side of the first member to adjacent a first side of the second member, the second arm being located between the first and third arms: and
a fourth arm, a fifth arm, and a sixth arm extending from adjacent a second side of the first member to adjacent a second side of the second member, the second side of the first member being opposite the first side of the first member, the second side of the second member being opposite the first side of the second member, the fifth arm being located between the fourth and sixth arms, the first arm being aligned with the fourth arm, the second arm being aligned with the fifth arm, and the third arm being aligned with the sixth arm;
wherein an intermediate portion of the first arm defines a first junction, an intermediate portion of the second arm defines a second junction, an intermediate portion of the third arm defines a third junction, an intermediate portion of the fourth arm defines a fourth junction, an intermediate portion of the fifth arm defines a fifth junction, and an intermediate portion of the sixth arm defines a sixth junction;
the second junction being located between the first and third junctions;
the fifth junction being located between the fourth and sixth junctions;
the fifth junction being aligned with the second junction, the first junction being aligned with the fourth junction, and the third junction being aligned with the sixth junction; and
the first member being movable relative to the second member between the open state and the closed state about the first junction, the second junction, the third junction, the fourth junction, the fifth junction, and the sixth junction.

2. The device of claim 1, wherein one of:
(i) at least a portion of the first member is abuttable with at least a portion of the second member when the device is in the closed state; and
(ii) the first and second members are closer to each other when the device is in the closed state as compared to when the device is in the open state.

3. The device of claim 1, wherein:
the first side of the first member and the second side of the first member are conjoined by at least one of a first cross member and a first plate; and
the first side of the second member and the second side of the second member are conjoined by at least one of a second cross member and a second plate.

4. The device of claim 1, wherein at least one of the first member and the second member has at least one row of teeth, each row of the at least one row having a plurality of teeth.

5. The device of claim 4, wherein the at least one row of teeth comprises a plurality of rows of teeth.

6. The device of claim 1, wherein at least one of the first member and the second member defines at least one recess for receiving at least one finger.

* * * * *